(12) United States Patent
Álvarez Builla Gómez et al.

(10) Patent No.: US 8,835,466 B2
(45) Date of Patent: *Sep. 16, 2014

(54) SYNTHESIS AND USES OF PYROGLUTAMIC ACID DERIVATIVES

(75) Inventors: Julio Álvarez Builla Gómez, Madrid (ES); José Luis Novella Robisco, Madrid (ES); Ma Paz Matía Martín, Madrid (ES); Sonia Serna Pereda, Bilbao (ES)

(73) Assignee: Prodimed, S.A., Madrid (ES)

( * ) Notice: Subject to any disclaimer, the term of this patent is extended or adjusted under 35 U.S.C. 154(b) by 674 days.

This patent is subject to a terminal disclaimer.

(21) Appl. No.: 12/297,571

(22) PCT Filed: Apr. 20, 2007

(86) PCT No.: PCT/EP2007/053900
§ 371 (c)(1),
(2), (4) Date: Oct. 17, 2008

(87) PCT Pub. No.: WO2007/122199
PCT Pub. Date: Nov. 1, 2007

(65) Prior Publication Data
US 2009/0163555 A1   Jun. 25, 2009

(30) Foreign Application Priority Data

Apr. 20, 2006 (EP) .................................. 06380090

(51) Int. Cl.
*A61K 31/4439* (2006.01)
*C07D 401/06* (2006.01)
*C07K 5/078* (2006.01)
*C07D 487/10* (2006.01)
*A61K 38/00* (2006.01)

(52) U.S. Cl.
CPC ......... *C07K 5/06173* (2013.01); *A61K 31/4439* (2013.01); *C07D 401/06* (2013.01); *A61K 38/00* (2013.01); *C07D 487/10* (2013.01)
USPC ........................................ 514/343; 546/278.4

(58) Field of Classification Search
CPC ........................ C07D 401/06; A61K 31/4439
USPC ........................................ 514/343; 546/278.4
See application file for complete search history.

(56) References Cited

U.S. PATENT DOCUMENTS 7,671,206 B2 * 3/2010 Gomez et al. ................. 546/208

FOREIGN PATENT DOCUMENTS

EP        0768308 A1    4/1997
WO     2004039314 A2    5/2004

OTHER PUBLICATIONS

Graham, B.S., "Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM. pp. I-20-38, 2000.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Luo et al. Cell 2009, 136, 823-837.*
Berge et al. J. Pharm. Sci. 1997, 66, pp. 1-19.*
Bluhm et al. Tetrahedron Letters 1998, 39, 3623-3626.*
Pattenden et al. Tetrahedron Letters 2002, 43, 2459-2461.*
Ahmadian, M., et al., Enantioselective route to key intermediates in the synthesis of carbocyclic phosphoribosyltransferase state analogues, Tetrahedron, 2001, pp. 9899-9909, vol. 57, Elsevier Science Ltd.
Cuadrado, S.P., et al., Immunomodulation in Established Murine Tumors: Response and Survival Rate Enhancement by Blood Leukocyte-Augmenting Substance 236 (Cl-), a Novel Synthetic Compound, Clinical Cancer Research, Nov. 15, 2003, pp. 5776-5785, vol. 9.
Hedley, S.J., et al., Development of a [3+3] Cycloaddition Strategy toward Functionalized Piperidines, Journal of Organic Chemistry, 2003, pp. 4286-4292, vol. 68, American Chemical Society.
Kantam, M.L., et al., Microencapsulated Cu(acac)2: a recoverable and reusable polymer-supported copper catalyst for aziridination of olefins, Tetrahedron Letters, 2003, pp. 9029-9032, vol. 44, Elsevier Ltd.
Moody, C.M., et al., Stereospecific synthesis of naturally-occuring 4-alkylideneglutamic acids, 4-alkylglutamates and 4-alkylprolines, Journal of the Chemical Society, Perkin Transactions I, 1997, pp. 3519-3530, vol. 23, Royal Society of Chemistry.

(Continued)

*Primary Examiner* — Joseph Kosack
*Assistant Examiner* — Matthew Coughlin
(74) *Attorney, Agent, or Firm* — Tristan A. Fuierer; Andrew D. Gerschutz; Moore & Van Allen, PLLC

(57) ABSTRACT

Novel pyroglutamic acid derivatives (I), wherein $R_1$ is —OH, —ORa, wherein Ra is alkyl, cycloalkyl, alkenyl, cycloalkenyl, aryl, aralkyl or heterocyclyl; $R_2$, $R_3$ and $R_4$ are independently H, a nitrogen protecting group which hydrolyzes under acidic conditions or phtalamide; X is a pharmaceutically acceptable anion; and Y is a N-containing group; either in the form of their isolated optically active stereoisomers or in the form of mixtures thereof, are useful compounds for enhancing an immuneresponse in a subject and/or for treating tumors, bacterial, fungal or viral infections, or autoimmune diseases.

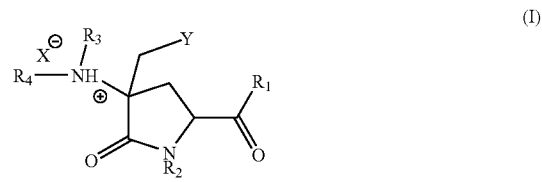

(I)

5 Claims, 4 Drawing Sheets

(56) References Cited

OTHER PUBLICATIONS

Ezquerra, J., et al., Stereoselective Double Alkylation of Ethyl N-Boc-pyroglutamate, Journal of Organic Chemistry, 1994, pp. 4327-4331, vol. 59, American Chemical Society.

Ezquerra, J., et al., Synthesis of Enantiomerically Pure 4-Substituted Glutamic Acids and Prolines: General Aldol Reaction of Pyroglutamate Lactam Lithium Enolate Mediated by Et2O-BF3, Journal of Organic Chemistry, 1995, pp. 2925-2930, vol. 60, American Chemical Society.

Ezquerra, J., et al., Stereoselective Reactions of Lithium Enolates Derived from N-BOC Protected Pyroglutamic Esters, Tetrahedron, 1993, pp. 8665-8678, vol. 49, Pergamon Press Ltd., Great Britain.

Ezquerra, J., et al., Efficient Synthesis of 4-Methylene-L-Glutamic Acid and its Cyclopropyl Analogue, Tetrahedron: Asymmetry, 1994, pp. 921-926, vol. 5, Elsevier Science Ltd., Great Britain.

Herdeis, C., et al., A stereoselective synthesis of 3-substituted (S)-pyroglutamic and glutamic acids via OBO ester derivatives, Tetrahedron, 2003, pp. 217-229, vol. 59, Elsevier Science Ltd.

Pedregal, C., et al., Highly Chemoselective Reduction of N-Boc Protected Lactams, Tetrahedron Letters, 1994, pp. 2053-2056, vol. 35, No. 13, Elsevier Science Ltd., Great Britain.

* cited by examiner

SYNTHESIS AND USES OF PYROGLUTAMIC ACID DERIVATIVES

CROSS-REFERENCE TO RELATED APPLICATIONS

This application is filed under the provisions of 35 U.S.C. §371 and claims the priority of International Patent Application No. PCT/EP2007/053900 filed on 20 Apr. 2007 entitled "Synthesis and Uses of Pyroglutamic Acid Derivatives" in the name of Julio Álvarez Builla Gómez, et al., which claims priority of European Patent Application No. 06380090.8 filed on 20 Apr. 2006, both of which are hereby incorporated by reference herein in their entirety.

FIELD OF THE INVENTION

The present invention refers to a new synthesis of pyroglutamic acid derivatives, their isolated optically active stereoisomers and mixtures thereof and their uses, and to new intermediates towards the synthesis of the same. The present invention also refers to the therapeutic use of said pyroglutamic acid derivatives, their optically active stereoisomers and mixtures thereof.

BACKGROUND OF THE INVENTION

European patent EP 0768308 B1 discloses mixtures of stereoisomers of pyroglutamic acid derivatives having the following general formula

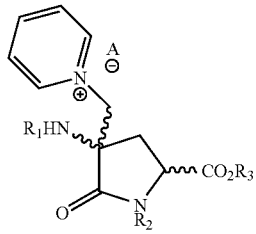

wherein $R_1$, $R_2$ and $R_3$ may be hydrogen or —C(=O)Me and A may be Cl—, $CH_3COO$— or HO— to stimulate immune biological response. The process disclosed therein for the synthesis of said compounds comprises reacting L-serine with a molar excess of acetic anhydride and pyridine under heat. Therefore, as disclosed in said document, the different stereoisomers have never been isolated and the in vivo and in vitro assays disclosed therein are performed with the mixtures of the four possible optically active stereoisomers all together. No indication regarding pure or enriched mixtures of the individual stereoisomers is disclosed. Further, no indication regarding the isolation of the different optically active stereoisomers from the mixture disclosed is given.

It is known to the skilled person that the different optically active stereoisomers of a compound may have different, or even opposite, effects. For example, a compound may have therapeutic effects while its enantiomer may be toxic. Examples of such situations are well known to the skilled person. Dextromethorphan is a decongestant, while levomethorphan is a potent narcotic.

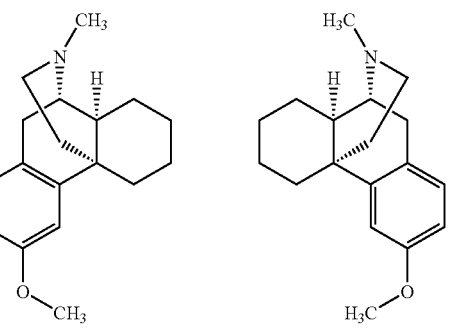

Dextromethorphan      Levomethorphan

It is also known the different in vivo behaviour of the enantiomers of Perhexiline.

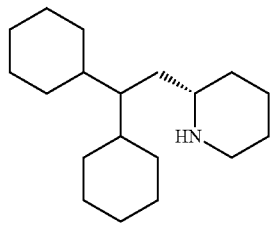

S-Perhexiline

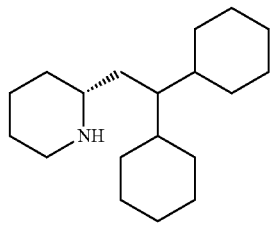

R-Perhexiline

They are both modulators of cardiac rhythm, but one of the enantiomers is methanolised more slowly and accumulates in the body, situation which caused a number of deaths during 80's.

Probably the most tragic and well known example is thalidomide, which was administered as a racemic mixture to pregnant women in order to treat mourning sickness.

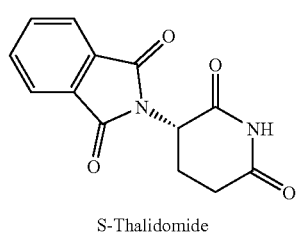

S-Thalidomide

-continued

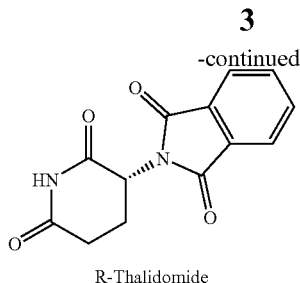

R-Thalidomide

While R-thalidomide was effective, the teratogenic effects of S-thalidomide where later discovered.

Therefore, in the search for new compounds with beneficial therapeutic effects it is usually necessary to perform assays with the enantiomerically pure stereoisomers in an attempt to select the most active enantiomers and/or to discard the eventual toxic ones. Thus, there is a need to provide isolated stereoisomers of pyroglutamic acid derivatives.

SUMMARY OF THE INVENTION

The present invention provides a process for obtaining pyroglutamic acid derivatives, their optically active stereoisomers and mixtures thereof. The process involves the use of an optically active stereoisomer of a precursor of a pyroglutamic acid derivative which can be easily separated and subsequently transformed in order to yield the desired optically active stereoisomer.

In particular, the inventors have envisaged a synthesis in which the different intermediates are isolated, if desired, with the desired stereochemistry. These intermediate products may be further transformed in order to provide the desired pyroglutamic acid derivative either in the form of the desired substantially pure stereoisomer or in the form of a mixture of stereoisomers. The inventors start from an enantiomerically pure compound of formula IV, generating then diastereomeric intermediates and final products which can be easily separated and purified. Using the compound of formula IV with the desired stereochemistry it is possible to obtain intermediates in the form of substantially pure stereoisomers or in the form of a mixture of stereoisomers. Said compound of formula IV may be synthesized using enantiomerically pure glutamic acid.

Therefore, according to an aspect, the present invention is directed to a process to obtain a substantially pure stereoisomer of a compound of formula I, or mixtures thereof, which comprises reacting a compound of formula IV with a compound of formula V in order to obtain a substantially pure stereoisomer of a compound of formula III or mixtures thereof; transforming said substantially pure stereoisomer of a compound of formula III or mixtures thereof into a substantially pure stereoisomer of a compound of formula II or mixtures thereof; and, finally, reacting said substantially pure stereoisomer of a compound of formula II or mixtures thereof with a compound of formula HX to render the desired pyroglutamic acid derivative of formula I as a substantially pure stereoisomer or mixtures thereof.

A further aspect of the present invention relates to a substantially pure stereoisomer of a compound of formula I (i.e., Ia, Ib, Ic or Id). Some compositions comprising mixtures of the substantially pure stereoisomers of a compound of formula Ia, Ib, Ic and/or Id constitute a further aspect of the present invention, such as a composition comprising the stereoisomers of formula Ia, Ib, Ic and/or Id with the proviso that said composition does not simultaneously contain mixtures of all four stereoisomers of the following compounds:

(i) 1-(3-amino-5-carboxy-2-oxopyrrolidin-3-ylmethyl)pyridinium chloride hydrochloride, or
(ii) 1-(1-acetyl-3-amino-5-carboxy-2-oxopyrrolidin-3-ylmethyl)pyridinium chloride hydrochloride.

A further aspect of the present invention relates to a substantially pure stereoisomer of a compound of formula III or mixtures thereof. The process to obtain the said compound constitutes an additional aspect of the present invention.

A further aspect of the present invention relates to a process to obtain a substantially pure stereoisomer of a compound of formula II, or a substantially pure stereoisomer of said compound of formula I. A substantially pure stereoisomer of a compound of formula II (i.e., IIa, IIb, IIc or IId) constitutes an additional aspect of the present invention. Some compositions comprising mixtures of the substantially pure stereoisomers of a formula IIa, IIb, IIc and/or IId also constitute a further aspect of the present invention.

A further aspect of the present invention relates to some pharmaceutical compositions comprising a compound selected from the group of compounds of formula Ia, Ib, Ic, Id and mixtures thereof, and a pharmaceutically acceptable excipient.

A further aspect of the present invention relates to the use of a compound selected from the group of compounds of formula Ia, Ib, Ic, Id and some mixtures thereof, in the manufacture of a composition for preventing or treating tumors.

DETAILED DESCRIPTION OF THE INVENTION

Definitions

Figure 1:
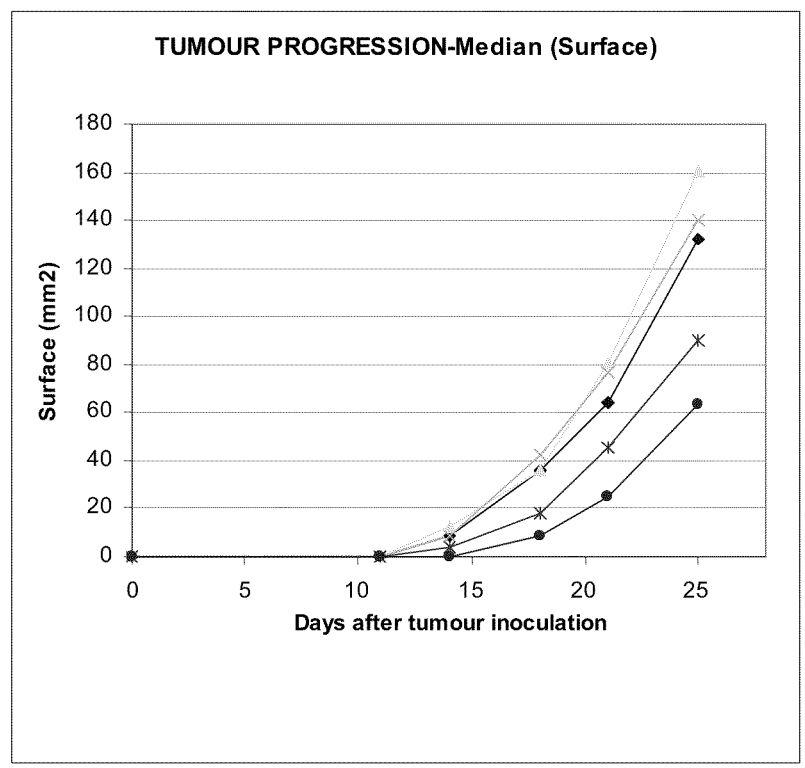
FIG. 1 is a graph showing the inhibitory effect of the isomers (1-4) assayed on Renca tumour cell growth compared to placebo (P.S.) [Example 6], expressed as the mean of tumour surfaces.

In order to facilitate the comprehension of the present invention, the meanings of some terms and expressions as used in the context of the invention are included herein.

"Alkyl" refers to a straight or branched hydrocarbon chain radical consisting of carbon and hydrogen atoms, containing no unsaturation, having 1-12, preferably one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as halo, hydroxy, alkoxy, O-propyl, O-benzyl, O-benzoate, carboxy, cyano, carbonyl, acyl, alkoxycarbonyl, amino, imino, nitro, mercapto and alkylthio.

"Alkenyl" refers to a straight or branched hydrocarbon chain radical consisting of carbon and hydrogen atoms, containing at least one unsaturation, having 1-12, preferably one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as halo, hydroxy, alkoxy, O-propyl, O-benzyl, O-benzoate, carboxy, cyano, carbonyl, acyl, alkoxycarbonyl, amino, imino, nitro, mercapto and alkylthio.

"Alkoxy" refers to a radical of the formula —O-alkyl, where alkyl has been previously defined, e.g., methoxy, ethoxy, propoxy, etc.

"Aryl" refers to an aromatic hydrocarbon radical such as phenyl, naphthyl or anthracyl. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

"Aryloxy" refers to a radical of formula —O-aryl, where aryl has been previously defined. Some examples of araloxy compopounds are —O-phenyl, —O-p-tolyl, —O-m-tolyl, —O-o-tolyl or —O-naphtyl.

"Amino" refers to a radical of the formula —NH$_2$, —NHRa, —NRaRb, wherein Ra and Rb are independently selected from substituted or unsubstituted alkyl, substituted or unsubstituted cycloalkyl, substituted or unsubstituted alkenyl, substituted or unsubstituted cycloalkenyl, substituted or unsubstituted aryl, substituted or unsubstituted aralkyl or substituted or unsubstituted heterocyclyl; or Ra and Rb together form a substituted or unsubstituted heterocycle, substituted or unsubstituted cycloalkyl or substituted or unsubstituted cycloalkenyl.

"Aralkyl" refers to an aryl group linked to an alkyl group such as benzyl and phenethyl.

"Carboxyester" refers to a —CO$_2$Ra, wherein Ra is selected from substituted or unsubstituted alkyl, substituted or unsubstituted cycloalkyl, substituted or unsubstituted alkenyl, substituted or unsubstituted cycloalkenyl, substituted or unsubstituted aryl, substituted or unsubstituted aralkyl or substituted or unsubstituted heterocyclyl.

"Cycloalkyl" refers to a saturated carbocyclic ring having from 3 to 8 carbon atoms.

"Cycloalkenyl" refers to a carbocyclic ring having from 3 to 8 carbon atoms and at least one unsaturation.

"Heterocyclyl" refers to a stable 3- to 15-membered ring which consists of carbon atoms and from one to five heteroatoms selected from the group consisting of nitrogen, oxygen, and sulphur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

"Heteroaryl" refers to a heterocyclic group wherein at least one of the rings is an aromatic ring.

"Protecting group" refers to a group that blocks an organic functional group and can be removed under controlled conditions. Protecting groups, their relative reactivities and conditions under which they remain inert are known to the skilled person. Reference is made to Greene and Wuts "Protective Groups in Organic Synthesis", John Wiley & Sons, Inc., New York, 1999.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a $C_1$-$C_6$ alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The term "pharmaceutically acceptable anion" makes reference to any anion which is capable of forming a pharmaceutically acceptable salt when in the presence of an appropriate counter cation. Examples of pharmaceutically acceptable anions, are Cl$^-$, Br$^-$, I$^-$, F$^-$, SO$_4^{2-}$, acetate, maleate, fumarate, citrate, oxalate, succinate, tartrate, malate, mandelate, methanesulphonate, p-toluenesulphonate, etc. Other examples of pharmaceutically acceptable anions may be apparent to the skilled person.

The term "pharmaceutically acceptable salts" refers to any pharmaceutically acceptable salt, which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, can be carried out by methods known in the art.

For instance, pharmaceutically acceptable salts of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

"Enantiomerically enriched" applied to a mixture of enantiomers refers to a mixture of enantiomers of a compound in which one of them is present in greater amounts than the other enantiomer. Therefore, enantiomerically enriched mixtures have an enantiomeric excess above 0% with regard to one of its enantiomers, preferably above 20%, preferably above 40%, preferably above 70%, more preferably above 80%, more preferably above 90% and more preferably above 95%.

An "enantiomerically pure" compound can be considered as a mixture of two enantiomers having enantiomeric excess above 95%, preferably above 98%, more preferably above 99%, more preferably above 99.5%.

A "substantially pure" compound in the present patent application makes references to a compound having purity above 95%, preferably above 98%, more preferably above 99%, more preferably above 99.5%.

An "stereoisomer" in the present patent application makes reference to compounds made up of the same atoms bonded by the same sequence of bonds but having different three-dimensional structures which are not interchangeable.

"Nitrogen containing nucleophile" refers to a molecule having at least one nitrogen with at least one free pair of electrons, said pair of electrons being capable of forming a bond with an electrophilic (electron deficient) moiety of another molecule or within the same molecule. Examples of nitrogen containing nucleophiles are primary, secondary or terciary amines, unsubstituted nitrogen atoms forming part of an heterocycle, even the nitrogen atom of an amide moiety may under certain circumstances act as a nucleophile.

EP 0768308 B1 Yields Mixtures of Stereoisomers of Piroglutamic Acid Derivatives

All attempts to separate the mixtures of stereoisomers disclosed in EP 0768308 B1, into the substantially pure compounds thereof failed. Following the inventors experimental section, 5% of the compound identified as BLAS-236(Cl) (1-(3-amino-5-carboxy-2-oxopyrrolidin-3-ylmethyl)pyridinium chloride hydrochloride) in the above cited European patent

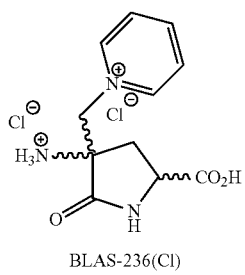

BLAS-236(Cl)

was obtained as a mixture of all four possible stereoisomers.

Also, its immediate precursor BLAS-320(Ac) (1-(1-acetyl-3-acetylamino-5-carboxy-2-oxopyrrolidin-3-ylmethyl)pyridinium acetate)

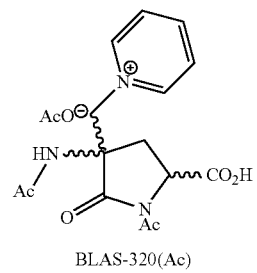

BLAS-320(Ac)

was synthesized using different procedures. The compound of formula BLAS-320(Ac) was obtained as a mixture of stereoisomers impossible to purify, mainly due to solubility problems (compound BLAS-320(Ac) was only soluble in water and methanol).

Furthermore, the substitution of counterion acetate by other anions in the compound of formula BLAS-320(Ac) was tried, but failed. Additionally, the transformation (or direct synthesis) and further purification of the compound of formula BLAS-320(Ac) into the ester derivatives thereof, was attempted. The black crude mixtures obtained were impossible to purify in all cases.

In view of the above facts, it was realized that the disclosure of EP 0768308 B1 was insufficient to obtain the desired substantially pure stereoisomers of the piroglutamic acid derivatives referred therein. Therefore, a totally different approach was developed.

Synthesis of the Substantially Pure Stereoisomers of a Compound of Formula I and Mixtures Thereof In an aspect, the invention relates to a process, hereinafter referred to as the process of the invention, for the synthesis of a substantially pure stereoisomer of a compound of formula I

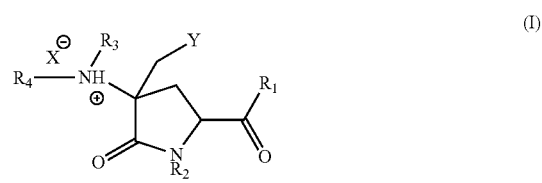

wherein $R_1$ is selected from —OH, —ORa, wherein Ra is selected from substituted or unsubstituted alkyl, substituted or unsubstituted cycloalkyl, substituted or unsubstituted alkenyl, substituted or unsubstituted cycloalkenyl, substituted or unsubstituted aryl, substituted or unsubstituted aralkyl or substituted or unsubstituted heterocyclyl;

$R_2$, $R_3$ and $R_4$ are independently selected from hydrogen, a nitrogen protecting group which hydrolyzes under acidic conditions or phtalamide;

X is a pharmaceutically acceptable anion; and

Y is an organic residue selected from (i) a N-containing group of formula VIa

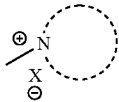

(VIa)

wherein
    the dotted line together with the nitrogen atom form a substituted or unsubstituted heteroaryl, and
    X is that previously defined; or (ii) a N-containing group of formula VIb

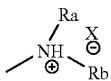

(VIb)

wherein
    X is that previously defined; and
    Ra and Rb are independently selected from substituted or unsubstituted alkyl, substituted or unsubstituted cycloalkyl, substituted or unsubstituted alkenyl, substituted or unsubstituted cycloalkenyl, substituted or unsubstituted aryl, substituted or unsubstituted aralkyl or substituted or unsubstituted heterocyclyl; or
    Ra and Rb together with the nitrogen atom to which they are attached form a substituted or unsubstituted heterocycle;

or mixtures thereof;

which comprises a) reacting an enantiomerically pure compound of formula IV

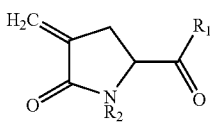

IV wherein $R_1$ and $R_2$ are those previously defined;

or mixtures thereof;

with a compound of formula V

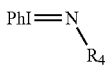

(V)

wherein $R_4$ is that previously defined;

to render a substantially pure stereoisomer of a compound of formula III,

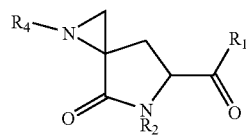

(III)

wherein $R_1$, $R_2$ and $R_4$ are those previously defined;

or mixtures thereof;

b) transforming said substantially pure stereoisomer of a compound of formula III or mixtures thereof into a substantially pure stereoisomer of a compound of formula II

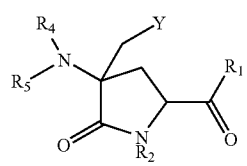

(II)

wherein
$R_1$, $R_2$ and $R_4$ are those previously defined;
$R_5$ is selected from a negative charge or $R_3$, wherein $R_3$ is that previously defined; and
Y is a N-containing organic residue selected from
    (i) when $R_5$ is a negative charge, Y is a N-containing organic residue of formula VIIa

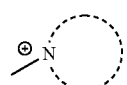

(VIIa)

wherein
    the dotted line together with the nitrogen atom form a substituted or unsubstituted heteroaryl; or
    (ii) when $R_5$ is $R_3$, Y is a N-containing organic residue selected from
    (ii.a) a N-containing group of formula VIIb

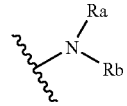

(VIIb)

wherein Ra and Rb are those previously defined; or
(ii.b) a N-containing organic residue of formula VIIc

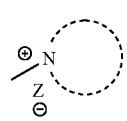

(VIIc)

wherein
    the dotted line together with the nitrogen atom form a substituted or unsubstituted heteroaryl; and
    Z is a pharmaceutically acceptable anion;

or mixtures thereof; and c) contacting said substantially pure stereoisomer of a compound of formula II or mixtures thereof with acid media comprising an acid of formula HX, wherein X is defined as above, to render said substantially pure stereoisomer of a compound of formula I or mixtures thereof.

The role of the nitrogen protecting groups which hydrolyze under acidic conditions ($R_2$, $R_3$ and/or $R_4$) is to protect the nitrogen functionality until step c) (transforming the compounds of formula II into the compounds of formula I by reacting said compound of formula II with a compound of formula HX). Any nitrogen protecting group which can protect the nitrogen atom until step c) is suitable for the present invention. Preferred nitrogen protecting groups which hydrolyze under acidic conditions are those which may be hydrolyzed during step c) at the same time the salt or disalt is formed to yield a compound of formula I. In this way, during step c) the nitrogen atoms of the molecule are deprotected and the salt or disalt is formed in a single synthetic step. However, according to the present invention, it is not essential that the salt or disalt are formed at the same time the nitrogen atoms are deprotected. Therefore, according to an embodiment of the invention, salt or disalt formation and deprotection of the nitrogen atoms may require more than one step.

According to a preferred embodiment, nitrogen protecting groups which hydrolyze under acidic conditions are selected from carbamates of formula —(O═)C—O—Ra, wherein Ra has the same meaning as above, preferably wherein Ra is benzyl, —C(CH$_3$)$_3$ or —CH$_2$CH$_3$; or a sulfonate of formula —(O═)S(═O)—Ra wherein Ra has the same meaning as above, preferably wherein Ra is —CH$_3$ or tosylate.

Other protecting groups which hydrolyze under acidic conditions are known to the skilled person; see reference books such as Greene and Wuts "Protective Groups in Organic Synthesis", John Wiley & Sons, Inc., New York, 1999.

When at least one of $R_2$, $R_3$ and $R_4$ is phtalamide, it is necessary to perform a further step prior to salt or disalt formation (prior to step c) comprising a reduction or reaction with hydrazine (for more details on how to remove an phtalamide group, see as Greene and Wuts "Protective Groups in Organic Synthesis", John Wiley & Sons, Inc., New York, 1999).

The starting compound of formula IV of the process of the invention may be in the form of an enantiomerically pure compound (i.e., R or S) or in the form of a mixture of enantiomers (R and S), optionally enriched in one of them. As used herein, the term "mixture of enantiomers" includes any mixture of two enantiomers, either in equimolar ratios or not, and, as such, includes not only racemic mixtures of said two enantiomers but also mixtures enriched in any of said enantiomers.

When the compound of formula IV is in the form of an enantiomerically pure compound, the above mentioned reaction may yield two products (steroisomers), one corresponding to the attack from the β-face and another one corresponding to the attack from the α-face. In this case, the reaction shows low stereoselectivity and a mixture of the two possible compounds (steroisomers) is obtained from each of the enantiomers of the compound of formula IV.

Thus, according to a particular embodiment, the compound of formula IV is in the form of an enantiomerically pure compound. If the S isomer of the compound of formula IV is used as starting material, the reaction yields, in general, a mixture of a compound of formula IIIa

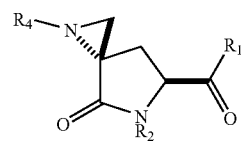

wherein $R_1$, $R_2$ and $R_4$ are those previously defined; and a compound of formula IIIb

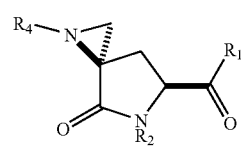

wherein $R_1$, $R_2$ and $R_4$ are those previously defined.

So, when the isomer of the compound of formula IV used is the S stereoisomer, the resulting compound of formula III obtained will be, generally, in the form of a mixture of its steroisomers of formula IIIa and IIIb. If desired, said compound of formula III, in the form of said mixture of steroisomers, may be isolated by conventional methods (e.g., silica, recrystallization, etc.) in order to obtain a mixture of IIIa and IIIb, either in an equimolar proportion or not. Alternatively, if desired, said mixture of steroisomers of formula IIIa and IIIb may be treated by conventional methods (e.g., recrystallization, chromatography, etc.) in order to separate each steroisomer and to obtain the stereoisomers of formula IIIa and IIIb as enantiomerically pure compounds.

Also, if the R isomer of the compound of formula IV is used as starting material, the reaction yields, in general, a mixture of a compound of formula IIIc,

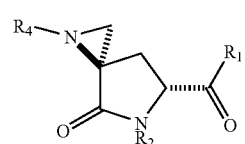

wherein $R_1$, $R_2$ and $R_4$ are those previously defined; and a compound of formula IIId

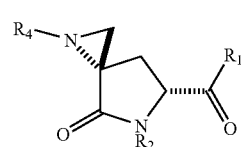

wherein $R_1$, $R_2$ and $R_4$ are those previously defined.

So, when the isomer of the compound of formula IV used is the R stereoisomer, the resulting compound of formula III obtained will be, generally, in the form of a mixture of its steroisomers of formula IIIc and IIId. As mentioned above, if desired, said compound of formula III, in the form of said mixture of steroisomers, may be isolated by conventional methods in order to obtain a mixture of IIIc and IIId, either in an equimolar proportion or not, or alternatively, said mixture of steroisomers may be treated by conventional methods in order to separate each steroisomer and to obtain the stereoisomers of formula IIIc and IIId as enantiomerically pure compounds.

Although this may seem to be a disadvantage, the inventors have found that the compounds of the mixture eventually obtained from the reaction of the compound of formula IV with the compound of formula V can be easily separated into the corresponding substantially pure stereoisomers of a compound of formula III, i.e., IIIa, IIIb, IIIc or IIId. This allows the synthesis of the substantially pure stereoisomers of a compound of formula I, which is an aspect of the present invention.

According to another particular embodiment, the compound of formula IV is in the form of a mixture of the two possible enantiomers (R or S), optionally, enantiomerically enriched with regard to one of said enantiomers. In such cases, the resulting compound of formula III is selected from a mixture of IIIa, IIIb, IIIc and IIId (in equimolar ratios or not); a mixture of IIIa and IIIc in an equimolar ratio or not; or a mixture of IIIb and IIId in an equimolar ratio or not.

The compound of formula IV can be obtained by processes known in the art. For example, one of the synthetic approaches used by the inventors is described in Scheme 1. The glutamic acid 1 (in this case, D-glutamic acid) may be transformed into a compound of formula 2 as described in Silverman, R. B.; Levy, M. A., *J. Org. Chem.* 1980, 45, 815. The second step is the protection of the amido nitrogen, using a known method (Flyn, D. L., et al., *J. Org. Chem.,* 1983, 48, 2424) to obtain a compound of formula 3. Then, the two next steps are: first, the substitution of the position 3- of the 2-pyrrolidone with a dimethylaminomethyl group, which gives 4 [which is really a mixture of two diastereomers, because the chiral centre in 3- is not controlled in the process] and the quaternisation with MeI, and elimination yields the compound of formula 5 (compound of formula IV wherein $R_1$ is -OEt and $R_2$ is BOC) which has already been described in Panday, S. K.; Griffart-Brunel, D.; Langlois, N.; *Tetrahedron Lett.,* 1994, 35, 6673. In this case, the compound of formula IV obtained has the R configuration. When the S configuration was desired, L-glutamic acid was used as starting material (as a general view, 5 has the same configuration as the starting glutamic acid).

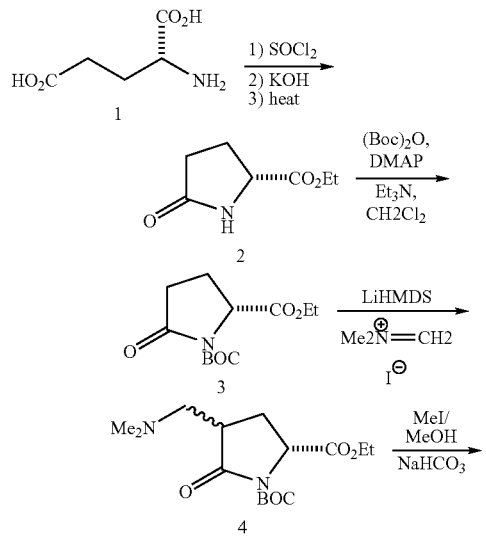

Scheme 1

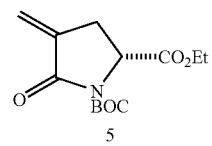

5

A first variant of the above mentioned method for the synthesis of compound 5 comprises the transformation of glutamic acid 1 (in this case, D-glutamic acid) into the pyroglutamic acid of formula 1' as described in Lennox, J. R.; Turner, S. C.; Rapoport, H. *J. Org. Chem.* 2001, 66, 7078-7083. Said pyroglutamic acid of formula 1' is then transformed into the compound of formula 2 described above by esterification in the presence of ethanol and $SOCl_2$ (see scheme 2).

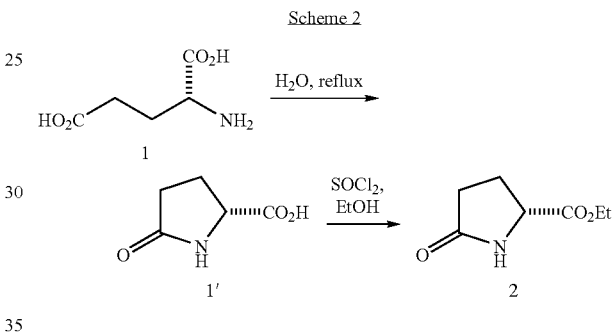

Scheme 2

A second variant of the above mentioned method for the synthesis of compound 5 comprises the transformation of the compound of formula 2 into the compound of formula 3 using DMAP as a base and acetonitrile (MeCN) as solvent.

A third variant of the above mentioned method for the synthesis of compound 5 comprises the transformation of the compound of formula 3 into a compound of formula 4' by reaction with $tBuOCH(NMe_2)_2$ (Bredereck's reagent). Said compound of formula 4' is transformed into the compound of formula 5 in a two step sequence. First, by reacting the compound of formula 4' with diluted HCl. Then, by reacting the resulting compound with aqueous HCHO (37%) in the presence of an inorganic base as described in WO 2004039314 (see scheme 3).

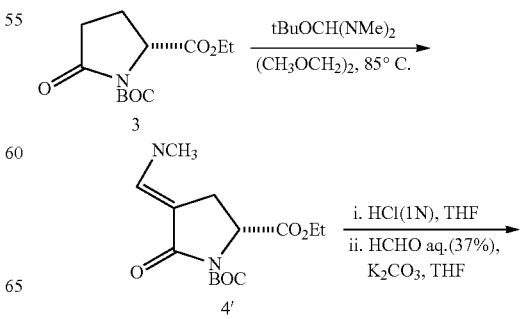

Scheme 3

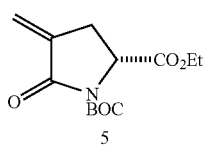

In order to achieve the formation of the aziridine ring there are a number of reagents known to the skilled person. However, the election of the reagent for the synthesis of spiro-aziridines from carbon-carbon double bonds is not easy. For example, the use of cloramine-T in the presence of HBr/$H_2O_2$ (L. J. Suman; B. S. Sharma; S. Bir. *Tetrahedron Letters* 2004, 45, 8731) did not yield the desired aziridine, but chlorinated derivatives of the following general formula

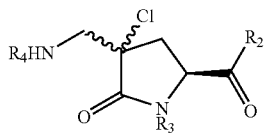

After a number of experiments, it was found that the most suitable reagent for the reaction was the benzyliodinane of formula V. According to a particular embodiment, $R_4$ is selected from —(O═)C—O—C($CH_3$)$_3$, —(O═)C—O—$CH_2CH_3$, —(O═)S(═O)-tosyl or phtalamide. In a preferred embodiment, the compound of formula V is N-tosyliminobenzyliodinane (Baron E.; O'Brien P.; Towers T. D. *Tetrahedron Lett.*, 2002, 43, 723), which may be synthesized following the method described in Gillepia, K., *Synthetic Comunn.* 2001, 123.

The reaction of the enantiomerically pure compound of formula IV, or mixtures thereof, with the compound of formula V to render a substantially pure stereoisomer of a compound of formula III, or mixtures thereof, can be carried out, if desired, in the presence of a catalyst, preferably a copper based catalyst, more preferably selected from Cu(ft)$_2$ or Cu(acac)$_2$, wherein "ft" is phtalocianine and "acac" is acetoacetate. For more details regarding catalysts and conditions, see Baron, E.; O'Brien, P.; Towers, T. D. *Tetrahedron Lett.*, 2002, 43, 723 and S. L. Jain, B. Sain, *Journal of molecular catalysis A: Chemical* 2003, 195, 283. This reaction is carried out typically in a suitable organic solvent at an appropriate temperature, preferably a temperature comprised between 0 and 100° C. Although practically any suitable organic solvent can be used in said reaction (e.g. acetonitrile, dimethyl formamide, etc.), in a particular embodiment, when the compound of formula IV is 4-methylene-5-oxopyrrolidine-1,2-dicarboxylic acid 1-tertbutyl ester 2-ethyl ester and the compound of formula V is N-tosyliminobenzyliodinane (PhI═NTs) [Examples 3.1 and 4.1], the organic solvent is acetonitrile and the reaction is carried out at a temperature comprised between 0° C. and room temperature (about 18° C.-24° C.).

Further, the substantially pure stereoisomers of the compound of formula III, or mixtures thereof, can be used for obtaining substantially pure stereoisomers of the pyroglutamic acid derivatives of formula I, or mixtures thereof, via the substantially pure stereoisomers of a compound of formula II or mixtures thereof.

Thus, a substantially pure stereoisomer of a compound of formula III or mixtures thereof, is further transformed into a substantially pure stereoisomer of a compound of formula II or mixtures thereof, by means of a strategy which depends on the nature of $R_5$ and Y, thus:

(A) in order to prepare a substantially pure stereoisomer of a compound of formula II or mixtures thereof wherein $R_5$ is a negative charge and Y is a N-containing organic residue of formula VIIa, the substantially pure stereoisomer of a compound of formula III or mixtures thereof, is reacted with a nitrogen containing nucleophile of formula VIIIa

VIIIa wherein
the dotted line together with the nitrogen atom form a substituted or unsubstituted heteroaryl, or (B) in order to prepare a substantially pure stereoisomer of a compound of formula II or mixtures thereof wherein $R_5$ is $R_3$ and Y is a N-containing organic residue of formula VIIb, the substantially pure stereoisomer of a compound of formula III or mixtures thereof, is reacted with a nitrogen containing nucleophile of formula VIIIb

VIIIb wherein Ra and Rb are those previously defined;
and, if desired, the resulting mixture is quenched with a compound of formula X $$R_3Z \qquad (X)$$

wherein $R_3$ and Z are those previously defined; or (C) in order to prepare a substantially pure stereoisomer of a compound of formula II or mixtures thereof wherein $R_5$ is $R_3$ and Y is a N-containing organic residue of formula VIIc the substantially pure stereoisomer of a compound of formula III or mixtures thereof, is reacted with a N-containing nucleophile of formula VIIIa, and the resulting mixture is quenched with said compound of formula X.

Briefly, as mentioned above, the synthesis of a substantially pure stereoisomer of a compound of formula II, or mixtures thereof, comprises reacting a substantially pure stereoisomer of a compound of formula III, or a mixture thereof, with
  a compound of formula VIIIa, or alternatively with,
  a compound of formula VIIIb, and, if desired, with a compound of formula X, or alternatively with,
  a compound of formula VIIIa and with a compound of formula X.

The starting compound of formula III may be in the form of a substantially pure stereoisomer [i.e., (3R,5R); (3S,5S); (3R,5S); or (3S,5R)] or in the form of a mixture of said substantially pure stereoisomers, e.g., as a mixture of diastereomers, etc., in the same or in different proportions. As used herein, the term "mixture of stereoisomers" includes any mixture of two or more stereoisomers of a compound, either in an equimolar ratio or not. In general, the stereochemistry of the starting material (compound of formula III) is maintained in the resultant product (compound of formula II).

Thus, according to a particular embodiment, the compound of formula III is in the form of an essentially pure stereoisomer thereof [i.e., (3R,5R); (3S,5S); (3R,5S); or (3S,5R)], in which case, an essentially pure compound of formula II which maintains the stereochemistry of the starting compound of formula III is obtained.

According to another particular embodiment, the compound of formula III is in the form of a mixture of said stereoisomers (i.e., a mixture of two or more stereoisomers selected from the compounds of formula IIIa, IIIb, IIIc and IIId), in an equimolar ratio or not. In this case, a mixture of stereoisomers of the compound of formula II is obtained maintaining the stereochemistry of the starting stereoisomers of formula III. The mixture of stereoisomers of formula II may be separated into its corresponding substantially pure stereoisomers following conventional methods such as silica gel chromatography or recrystallization.

In an embodiment, a substantially pure stereoisomer of a compound of formula III, or a mixture thereof, is reacted with a compound of formula VIIIa to yield a substantially pure stereoisomer of a compound of formula II, or mixtures thereof, wherein $R_5$ is a negative charge and Y is a N-containing organic residue of formula VIIIa [Option (A)].

In that case, in an embodiment, the nitrogen containing nucleophile VIIIa is a pyridine of formula IX

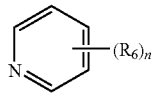

wherein,
n is 0, 1, 2, 3, 4 or 5; and
$R_6$ is selected from substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, halogen, substituted or unsubstituted carboxyester, substituted or unsubstituted amino and/or the pyridine forms one or more substituted or unsubstituted fused rings.

Further, according to a particular embodiment, said pyridine of formula IX is selected from pyridine and one of the following compounds

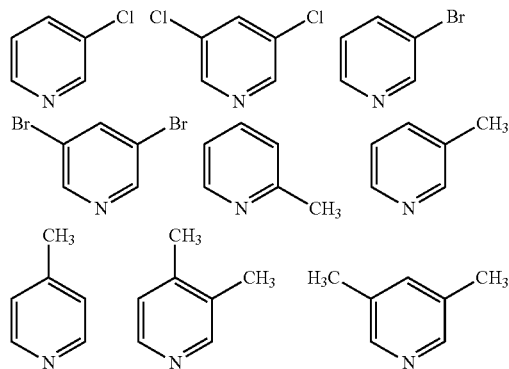

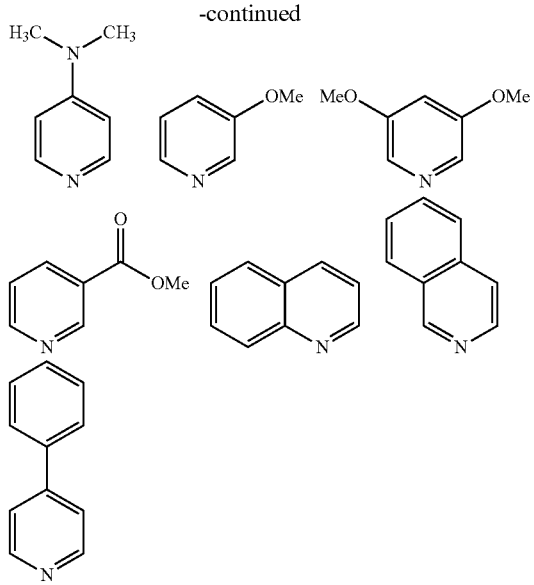

According to another particular embodiment, the nitrogen containing nucleophile VIIIa is a compound of formula

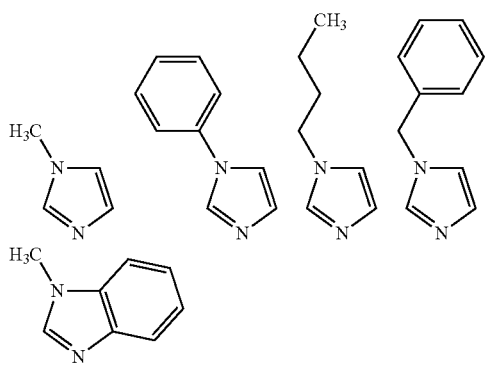

Generally, the reaction of the substantially pure stereoisomer of a compound of formula III, or a mixture thereof, with the compound of formula VIIIa is carried out under heating. In fact, the skilled person in the art knows that reactions such as the transformation of the compound of formula III into a compound of formula II, namely the ring opening of the aziridine ring in the presence of a nucleophile, usually require heat. Microwaves can be used, if desired. In a particular embodiment, heating is achieved by irradiating the reaction mixture under microwaves which easily allows to reach the desired temperature and maintaining the same for the desired period of time. According to an embodiment, the reaction is performed in the presence of a catalyst, such as montmorillonite, a porous acid catalyst (e.g. Examples 3.2.1, 3.2.2, 4.2.1 and 4.2.2).

In other embodiment, a substantially pure stereoisomer of a compound of formula III, or a mixture thereof, is reacted with a compound of formula VIIIb, and, optionally with a compound of formula X, to render a substantially pure stereoisomer of a compound of formula II, or mixtures thereof, wherein $R_5$ is $R_3$ and Y is a N-containing organic residue of formula VIIb [Option (B)].

In that case, in an embodiment, the nitrogen containing nucleophile VIIIb is a compound selected from the following compounds:

Under Option (B) there are essentially two possible types of conditions depending on the reactive species which attack the aziridine ring. On one hand, it is possible to generate the anion of a compound of formula VIIIb by contacting said compound of formula VIIIb with a strong base (i.e. Butyl lithium, etc.). Once the anion of the compound of formula VIIIb is formed, the compound of formula III may be added and the aziridine ring is attacked by the anion of the compound of formula VIIIb. The reaction may further continue by addition of the compound of formula X, for example, an alkylating compound such as methyl iodide ($R_3$=alkyl), etc. The conditions needed to form the anion of a compound of formula VIIIb are known to the skilled person in the art. Some of said species are even commercially available. Alternatively, it is possible to quench the reaction prior to the addition of a compound of formula X, in which case $R_3$ will be hydrogen in the resulting compound of formula II. On the other hand, it is possible to use directly the compound of formula VIIIb. These conditions usually require heat or microwaves and yield a compound of formula II wherein $R_3$ is hydrogen.

In still another embodiment, a substantially pure stereoisomer of a compound of formula III, or a mixture thereof, is reacted with a compound of formula VIIIa and with a compound of formula X, to render a substantially pure stereoisomer of a compound of formula II, or mixtures thereof, wherein $R_5$ is $R_3$ and Y is a N-containing organic residue of formula VIIc [Option (C)]. The compounds of formula VIIIa and X have been previously defined.

The skilled person in the art knows that reactions such as the transformation of the compound of formula III into a compound of formula II, namely the ring opening of the aziridine ring in the presence of a nucleophile, usually require heat. Microwaves can be used, if desired.

The compound of formula II has two chiral centres; therefore, it can be in the form of any of the essentially pure stereoisomers or mixtures thereof. In a particular embodiment, the compound of formula II is selected from the group consisting of:

a) a substantially pure compound of formula IIa,

IIa wherein $R_1$, $R_2$, $R_4$, $R_5$ and Y are those previously defined;
b) a substantially pure compound of formula IIb, IIb wherein $R_1$, $R_2$, $R_4$, $R_5$ and Y are those previously defined;
c) a substantially pure compound of formula IIc, IIc wherein $R_1$, $R_2$, $R_4$, $R_5$ and Y are those previously defined;
d) a substantially pure compound of formula IId, IId wherein $R_1$, $R_2$, $R_4$, $R_5$ and Y are those previously defined; and
e) any mixture of the above mentioned compounds of formula IIa, IIb, IIc and/or IId (in an equimolar ratio or not).

Preferred compounds of formula II, including their substantially pure stereoisomers, are mentioned below under the corresponding heading.

The resulting compounds of formula II may be isolated or directly used for the next step without further purification.

When a mixture of steroisomers of the compound of formula II is obtained, it is possible to isolate the desired stereoisomer by conventional methods known by the skilled person in the art.

Thus, according to the invention, a substantially pure stereoisomer of a compound of formula II, or mixtures thereof, immediate precursor of the substantially pure stereoisomer of the piroglutamic acid derivative of formula I, or mixtures thereof, with the desired stereochemistry, may be obtained by either purifying the resulting mixture of stereoisomers of the compound of formula III and then reactiong the isolated stereoisomers with the corresponding reagents, or, alternatively, by purifying the resulting mixture of the reaction between said compound of formula III and the nucleophile of formula VIIIa or VIIIb and X (if needed).

Thus, according to step c) of the process of the invention, a substantially pure stereoisomer of a compound of formula II, or mixtures thereof, is converted into the substantially pure stereoisomer of the pyroglutamic acid derivative of formula I, or mixtures thereof, by contacting said substantially pure stereoisomer of a compound of formula II, or mixtures thereof, with an acid media comprising an acid of formula HX, wherein X is defined as above.

The skilled person in the art is aware of the organic or inorganic acids of formula HX suitable to perform the reaction with the substantially pure stereoisomer of a compound of formula II or mixtures thereof. In a particular embodiment, said acid HX is an inorganic acid, such as HCl, HBr, etc. According to a preferred embodiment, HX is HBr.

Depending on the nature of the compounds of formula I and II, the reaction requires 1 or 2 equivalents of HX. The skilled person is aware of the conditions which are necessary to form the salt. According to an embodiment of the invention, the substantially pure stereoisomer of a compound of formula II, or mixtures thereof, is placed into contact with an excess of an acid of formula HX, wherein X is defined as above. According to a further embodiment, the substantially pure stereoisomer of a compound of formula II or mixtures thereof is dissolved in aqueous HBr and heated.

According to the above, it is possible to obtain a substantially pure stereoisomer of a compound of formula I or mixtures thereof, in a stepwise sequence from the substantially pure stereoisomer of a compound of formula III or mixtures thereof. However, it is also possible to obtain the substantially pure stereoisomer of a compound of formula I or mixtures thereof, from the compound of formula III following a one-pot strategy. It is, therefore, a further aspect of the invention, a one-pot process for the synthesis of a substantially pure stereoisomer of a compound of formula I or mixtures thereof, which comprises reacting a substantially pure stereoisomer of a compound of formula III or mixtures thereof, with a nitrogen containing nucleophile of formula VIIIa or VIIIb; and, subsequently, reacting the compound resulting from the previous step with an acid of formula HX.

The compound of formula I has two chiral centers; therefore, it can be in the form of any of the substantially pure stereoisomers thereof or in the form of a mixture thereof. Preferred compounds of formula I, including their essentially pure stereoisomers are mentioned below under the corresponding heading.

Compound of Formula I

The compounds of formula I have two chiral centers; therefore, they can be in the form of any of the essentially pure stereoisomers or of a mixture thereof. In a particular embodiment, the compound of formula I is selected from the group consisting of:

a) a substantially pure stereoisomer compound of formula Ia

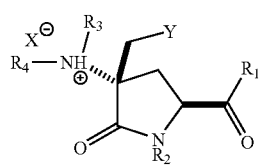

wherein $R_1$, $R_2$, $R_3$, $R_4$, X and Y are those previously defined;

b) a substantially pure stereoisomer compound of formula Ib,

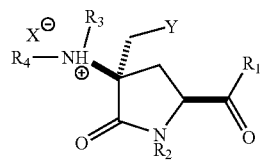

wherein $R_1$, $R_2$, $R_3$, $R_4$, X and Y are those previously defined;

c) a substantially pure stereoisomer compound of formula Ic

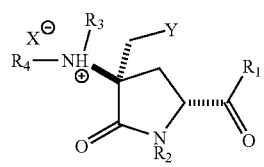

wherein $R_1$, $R_2$, $R_3$, $R_4$, X and Y are those previously defined;

d) a substantially pure stereoisomer compound of formula Id

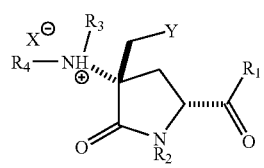

wherein $R_1$, $R_2$, $R_3$, $R_4$, X and Y are those previously defined; and e) any mixture of the above mentioned substantially pure compounds of formula Ia, Ib, Ic and/or Id, in an equimolar ratio or not, wherein said mixture does not contain simultaneously all four stereoisomers of the following compounds:
   (i) 1-(3-amino-5-carboxy-2-oxopyrrolidin-3-ylmethyl) pyridinium chloride hydrochloride, or
   (ii) 1-(1-acetyl-3-amino-5-carboxy-2-oxopyrrolidin-3-ylmethyl)pyridinium chloride hydrochloride.

Although some compounds of formula I, namely (i) 1-(3-amino-5-carboxy-2-oxopyrrolidin-3-ylmethyl)pyridinium chloride hydrochloride, and (ii) 1-(1-acetyl-3-amino-5-carboxy-2-oxopyrrolidin-3-ylmethyl)pyridinium chloride hydrochloride have been described as mixtures of all four possible stereoisomers thereof, no synthesis of their essentially pure stereoisomers has been achieved up to the date.

In a particular embodiment, in the compound of formula I, $R_1$ is —OH or —ORa, wherein Ra is that previously defined, preferably —OH.

In other particular embodiment, in the compound of formula I, $R_2$ is hydrogen, a nitrogen protecting group which hydrolyzes under acidic conditions or phtalamide, preferably hydrogen.

In other particular embodiment, in the compound of formula I, $R_3$ or $R_4$, independently, is hydrogen, a nitrogen protecting group which hydrolyzes under acidic conditions or phtalamide, preferably both of them are, simultaneously, hydrogen.

In other particular embodiment, in the compound of formula I, X is a pharmaceutically acceptable anion, preferably bromide or chloride.

In other particular embodiment, in the compound of formula I, $R_1$ is OH or ORa, preferably OH; $R_2$ is hydrogen, a nitrogen protecting group which hydrolyzes under acidic conditions or phtalamide, preferably hydrogen; $R_3$ or $R_4$, independently, are hydrogen, a nitrogen protecting group which hydrolyzes under acidic conditions or phtalamide, preferably $R_3$ or $R_4$ are, simultaneously, hydrogen; and/or X is a pharmaceutically acceptable anion, preferably bromide or chloride.

In other particular embodiment, in the compound of formula I, Y is an organic residue selected from

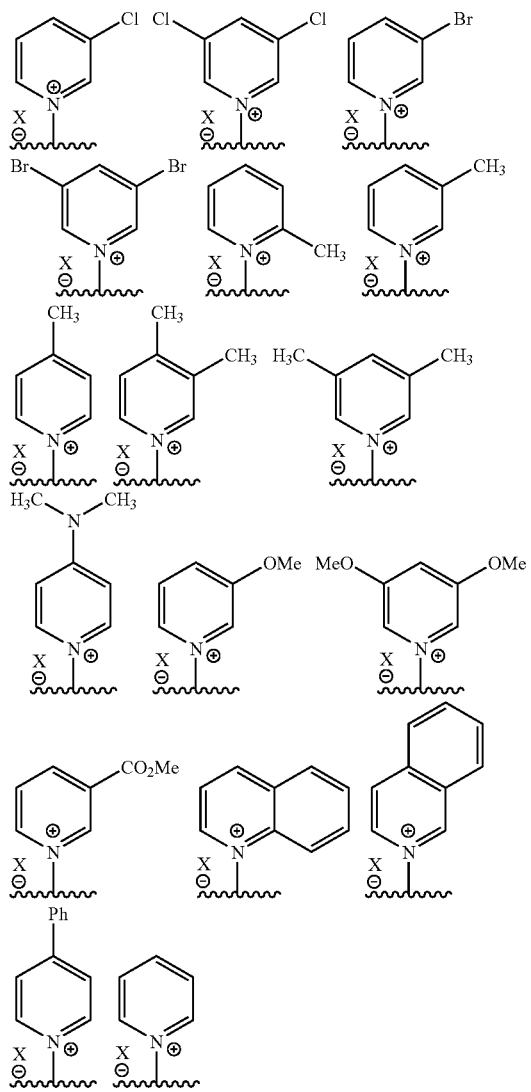

In other particular embodiment, in the compound of formula I, Y is an organic residue selected from

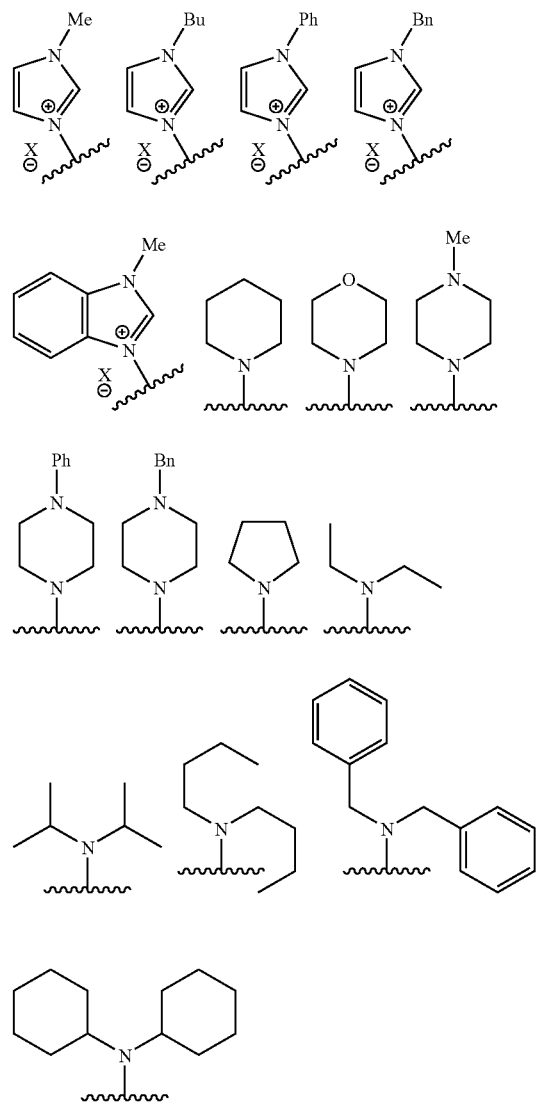

According to a particular embodiment, the compound of formula I is a substantially pure compound of formula I'a

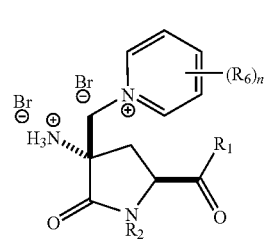

I'a wherein $R_1$, $R_2$, $R_6$ and n are those previously defined.

According to a particular embodiment of the invention, said compound of formula I is a substantially pure compound of formula I'b I'b

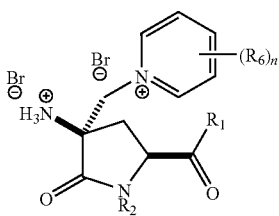

wherein $R_1$, $R_2$, $R_6$ and n are those previously defined.

According to a particular embodiment of the invention, said compound of formula I is a substantially pure compound of formula I'c, I'c

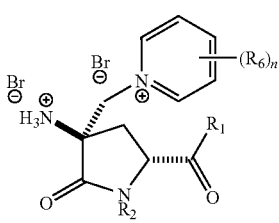

wherein $R_1$, $R_2$, $R_6$ and n are those previously defined.

According to a particular embodiment of the invention, said compound of formula I is a substantially pure compound of formula I'd I'd

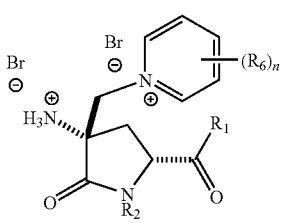

wherein $R_1$, $R_2$, $R_6$ and n are those previously defined.

According to a particular embodiment of the invention, a mixture comprising two or more compounds of formula I'a, I'b, I'c and/or I'd is provided, in equimolar ratios or not; e.g., a mixture comprising compounds of formula I'a and I'b, or comprising compounds of formula I'a and I'c, or comprising compounds of formula I'a and I'd, or comprising compounds of formula I'b and I'c, or comprising compounds of formula I'b and I'd, or comprising compounds of formula I'c and I'd, or comprising compounds of formula I'a, I'b and I'c, or comprising compounds of formula I'a, I'b and I'd, or comprising compounds of formula I'b, I'c and I'd, or comprising compounds of formula I'a, I'b, I'c and I'd.

According to a particular embodiment of the invention, the compound of formula I is selected from the group consisting of:
3S,5S-1-(3-amino-5-carboxy-2-oxopyrrolidin-3-ylmethyl) pyridinium bromide hydrobromide;
3R,5S-1-(3-amino-5-carboxy-2-oxopyrrolidin-3-ylmethyl) pyridinium bromide hydrobromide;
3R,5R-1-(3-amino-5-carboxy-2-oxopyrrolidin-3-ylmethyl) pyridinium bromide hydrobromide; and
3S,5R-1-(3-amino-5-carboxy-2-oxopyrrolidin-3-ylmethyl) pyridinium bromide hydrobromide.

The invention further provides a composition comprising a mixture of said compounds of formula Ia, Ib, Ic and/or Id, in equimolar ratios or not, wherein said mixture does not contain simultaneously all four stereoisomers of the following compounds
(i) 1-(3-amino-5-carboxy-2-oxopyrrolidin-3-ylmethyl)pyridinium chloride hydrochloride, or
(ii) 1-(1-acetyl-3-amino-5-carboxy-2-oxopyrrolidin-3-ylmethyl)pyridinium chloride hydrochloride.

Compound of Formula II

Although some compounds of formula II, namely 1-(3-amino-5-carboxy-2-oxopyrrolidin-3-ylmethyl)pyridinium acetate, 1-(1-acetyl-3-amino-5-carboxy-2-oxopyrrolidin-3-ylmethyl)pyridinium acetate, 1-(1-acetyl-3-acetylamino-5-carboxy-2-oxo-pyrrolidin-3-ylmethyl)pyridinium acetate or 1-(1-acetyl-3-acetylamino-5-carboxy-2-oxo-pyrrolidin-3-ylmethyl)pyridinium hydrochloride have been described as mixtures of all four possible stereoisomers thereof, no synthesis of their substantially pure stereoisomers has been achieved up to the date.

Thus, in another aspect, the invention relates to a substantially pure compound of formula II or mixtures thereof.

In a particular embodiment, the invention relates to a substantially pure compound of formula IIa, IIb, IIc and IId.

In a particular embodiment, the invention relates to a mixture of the above mentioned compounds of formula IIa, IIb, IIc and/or IId, in any molar ratio, wherein said mixture does not contain simultaneously all four stereoisomers of the following compounds:
1-(3-amino-5-carboxy-2-oxopyrrolidin-3-ylmethyl)pyridinium acetate;
1-(1-acetyl-3-amino-5-carboxy-2-oxopyrrolidin-3-ylmethyl)pyridinium acetate;
1-(1-acetyl-3-acetylamino-5-carboxy-2-oxo-pyrrolidin-3-ylmethyl)pyridinium acetate; or
1-(1-acetyl-3-acetylamino-5-carboxy-2-oxo-pyrrolidin-3-ylmethyl)pyridinium hydrochloride.

In another particular embodiment, the substantially pure stereoisomer of a compound of formula II, or mixtures thereof, is a compound wherein $R_1$ is —ORa, preferably wherein Ra is an alkyl group.

In another particular embodiment, the substantially pure stereoisomer of a compound of formula II, or mixtures thereof, is a compound wherein $R_2$ is —(O=)C—O—Ra, preferably the BOC group.

In another particular embodiment, the substantially pure stereoisomer of a compound of formula II, or mixtures thereof, is a compound wherein $R_4$ is —(O=)S(=O)—Ra, preferably tosyl.

In another particular embodiment, the substantially pure stereoisomer of a compound of formula II, or mixtures thereof, is a compound wherein $R_1$ is —ORa, preferably wherein Ra is an alkyl group; $R_2$ is —(O=)C—O—Ra, preferably the BOC group; and $R_4$ is —(O=)S(=O)—Ra, preferably tosyl.

According to another embodiment of the invention, the substantially pure stereoisomer of a compound of formula II, or mixtures thereof, is a compound wherein $R_2$, $R_4$ and $R_5$, are, independently, hydrogen.

According to another embodiment of the invention, the substantially pure stereoisomer of a compound of formula II, or mixtures thereof, is a compound wherein $R_1$ is —OH.

According to another embodiment of the invention, the substantially pure stereoisomer of a compound of formula II, or mixtures thereof, is a compound wherein $R_5$ is a negative charge.

The invention also relates to a composition comprising a compound selected from the group consisting of the above mentioned compounds of formula IIa, IIb, IIc, IId and mixtures thereof, in any molar ratio, wherein said mixture does not contain simultaneously all four stereoisomers of the following compounds:

1-(3-amino-5-carboxy-2-oxopyrrolidin-3-ylmethyl)pyridinium acetate;
1-(1-acetyl-3-amino-5-carboxy-2-oxopyrrolidin-3-ylmethyl)pyridinium acetate;
1-(1-acetyl-3-acetylamino-5-carboxy-2-oxo-pyrrolidin-3-ylmethyl)pyridinium acetate; or
1-(1-acetyl-3-acetylamino-5-carboxy-2-oxo-pyrrolidin-3-ylmethyl)pyridinium hydrochloride.

The substantially pure stereoisomer of a compound of formula II or mixtures thereof can be obtained, as mentioned above, by means of a process which comprises reacting a substantially pure stereoisomer of a compound of formula III or mixtures thereof, with
a compound of formula VIIIa, or alternatively with,
a compound of formula VIIIb, and, if desired, with a compound of formula X, or alternatively with,
a compound of formula VIIIa and with a compound of formula X.

Said process constitutes a further aspect of the present invention and makes possible the synthesis of substantially pure stereoisomers of the compound of formula II or mixtures thereof.

Compound of Formula III

In another aspect, the invention relates to a substantially pure stereoisomer of a compound of formula III or mixtures thereof. Said compound of formula III has two chiral centers; therefore, it can be in the form of any of the substantially pure stereoisomer or a mixture thereof.

In a particular embodiment, the compound of formula III is selected from the group consisting of the compounds of formula IIIa, IIIb, IIIc, IIId and any mixture thereof.

In another particular embodiment, the invention relates to a mixture comprising two or more compounds of formula IIIa, IIIb, IIIc and IIId. Illustrative, non-limiting examples of said mixtures include mixtures of two of those compounds (e.g., mixtures of IIIa and IIIb, IIIa and IIIc, IIIa and IIId, IIIb and IIIc, IIIb and IIId or IIIc and IIId), or mixtures of three of said compounds (e.g., mixtures of IIIa, IIIb and IIIc, IIIa, IIIb and IIId, or IIIb, IIIc and IIId), or mixtures of said four compounds (e.g., a mixture of IIIa, IIIb, IIIc and IIId). Each particular compound (IIIa to IIId) may be present in said mixture in any proportion or ratio, e.g., in equimolar proportions or ratios or in different proportions or ratios wherein one or more of said compounds are in excess with respect to the other(s).

In another particular embodiment, the substantially pure stereoisomer of a compound of formula III, or mixtures thereof, is a compound wherein $R_1$ is —ORa, preferably wherein Ra is an alkyl group.

According to another particular embodiment, the substantially pure stereoisomer of a compound of formula III, or mixtures thereof, is a compound wherein $R_2$ is —(O=)C—O—Ra, preferably the BOC group.

According to another particular embodiment, the substantially pure stereoisomer of a compound of formula III, or mixtures thereof, is a compound wherein $R_4$ is —(O=)S(=O)—Ra, preferably tosyl.

According to another particular embodiment, the substantially pure stereoisomer of a compound of formula III, or mixtures thereof, is a compound wherein $R_1$ is —ORa, preferably wherein Ra is an alkyl group; $R_2$ is —(O=)C—O—Ra, preferably the BOC group; and $R_4$ is —(O=)S(=O)—Ra, preferably tosyl.

According to another particular embodiment, the substantially pure stereoisomer of a compound of formula III, or mixtures thereof, is a compound wherein $R_2$, $R_4$ and $R_5$, are, independently, hydrogen.

The substantially pure stereoisomer of a compound of formula III or mixtures thereof, can be obtained, as mentioned above, by means of a process which comprises reacting a compound of formula IV, either in an enantiomerically pure form or in the form of a mixtures of enantiomers, with a compound of formula V. Said process constitutes a further aspect of the present invention. By means of said process, it is also possible to obtain substantially pure stereoisomers of a compound of formula III or mixtures thereof.

Uses of the Compound of Formula I and Pharmaceutical Compositions

The substantially pure stereoisomers of a compound of formula I, or mixtures thereof, may be used as active ingredients of medicaments for the treatment and/or prophylaxis of some conditions in a subject, e.g., tumours, immunodeficiencies, infections, etc.

Illustrative, non-limitative, examples of conditions susceptible of being treated with the substantially pure stereoisomer of a compound of formula I or mixtures thereof, include:

A) Cancer- or tumour-related conditions: comprising practically all cancer and tumour types, including Acute Lymphoblastic Leukemia, Adult Acute Lymphoblastic Leukemia, Childhood Acute Myeloid Leukemia, Adult Acute Myeloid Leukemia, Adrenocortical Carcinoma, Acquired Immunodeficiency Syndrome (AIDS)-Related Cancers, Anal Cancer, Astrocytoma, Childhood Cerebellar Astrocytoma, Basal Cali Carcinoma, Bile Duct Cancer, Extrahepatic Bladder Cancer, Bladder Cancer, Bone Cancer, Osteosarcoma/Malignant Fibrous Histiocytoma, Brain Stem Glioma, Brain Tumor, Malignant Glioma, Ependymoma, Medulloblastoma, Supratentorial Primitiva Neuroectodermal Tumors, Visual Pathway and Hypothalamic Glioma, Breast Cancer, Mate Bronchial Adenomas/Carcinoids, Childhood Burkitt's Lymphoma, Carcinoid Tumor, Gastrointestinal Carcinoma of Unknown Primary, Central Nervous System Lymphoma, Primary Cerebellar Astrocytoma, Cerebral Astrocytoma/Malignant Glioma, Cervical Cancer, Childhood Cancers, Chronic Lymphocytic Leukemia, Chronic Myelogenous Leukemia, Chronic Myeloproliferative Disorders, Colon Cancer, Colorectal Cancer, Cutaneous T-Cell Lymphoma, Endometrial Cancer, Esophageal Cancer, Childhood Ewing's Family of Tumors, Extracranial Germ Cell Tumor, Extragonadal Germ Cell Tumor, Extrahepatic Bile Duct Cancer, Eye Cancer, Intraocular Melanoma Eye Cancer, Retinoblastoma, Gallbladder Cancer, Gastric (Stomach) Cancer, Gastrointestinal Carcinoid Tumor, Germ Cell Tumor, Ovarian Gestational Trophoblastic Tumor Glioma, Adult Glioma, Brain Stem Glioma, Cerebral Astrocytoma Glioma, Hairy Cell Leukemia, Head and Neck Cancer, Hepatocellular (Liver) Cancer, Adult (Primary) Hepatocellular (Liver) Cancer, Childhood (Primary) Hodgkin's Lymphoma, Adult Hodgkin's Lymphoma, Hypopharyngeal Cancer, Intraocular Melanoma, Islet Cell Carcinoma (Endocrine Pancreas), Kaposi's Sarcoma, Kidney (Renal Cell) Cancer, Kidney Cancer, Laryngeal Cancer, Chronic Lymphocytic Leukemia, Chronic Myelogenous Leukemia, Hairy Cell, Lip and Oral Cavity Cancer, Childhood (Primary) Lung Cancer, Non-Small Cell Lung Cancer, Small Cell Lymphoma, AIDS-Related Lymphoma, Burkitt's Lymphoma, Cutaneous T-Cell, Hodgkin's Adult Lymphoma, Hodgkin's Childhood Lymphoma, Non- Hodgkin's Adult Lymphoma, Non-Hodgkin's Childhood Lymphoma, Primary Central Nervous System, Macroglobulinemia, WaldenstrOm's Malignant Fibrous Histiocytoma of Bone/Osteosarcoma, Medulloblastoma, Melanoma, Intraocular (Eye) Merkel Cell Carcinoma, Mesothelioma, Adult Malignant Mesothelioma, Childhood Metastatic Squamous Neck Cancer with Occult Primary, Multiple Endocrine Neoplasia Syndrome, Childhood Multiple Myeloma/Plasma Cell Neoplasm Mycosis Fungoides Myelodysplastic Syndromes, Myelodysplastic/Myeloproliferative Diseases Myelogenous Leukemia, Chronic Myeloid Leukemia, Adult Acute Myeloid Leukemia, Childhood Acute Myeloma, Multiple Myeloproliferative Disorders, Chronic Nasal Cavity and Paranasal Sinus Cancer Nasopharyngeal Cancer, Nasopharyngeal Cancer, Childhood Neuroblastoma, Oral Cancer, Childhood Oral Cavity Cancer, Lip and Oropharyngeal Cancer, Osteosarcoma/Malignant Fibrous Histiocytoma of Bone Ovarian Cancer, Childhood Ovarian Epithelial Cancer, Ovarian Germ Cell Tumor, Ovarian Low Malignant Potential Tumor, Pancreatic Cancer Pancreatic Cancer, Childhood Pancreatic Cancer, Islet Cell Paranasal Sinus and Nasal Cavity Cancer, Parathyroid Cancer, Penile Cancer, Pheochromocytoma, Pineoblastoma and Supratentorial Primitive Neuroectodermal Tumors, Childhood Pituitary Tumor, Plasma Cell Neoplasm/Multiple Myeloma, Pleuropulmonary Blastoma, Primary Central Nervous System Lymphoma, Prostate Cancer, Rectal Cancer, Renal Cell (Kidney) Cancer, Renal Cell (Kidney) Cancer, Childhood Renal Pelvis and Ureter, Transitional Cell Cancer Retinoblastoma, Rhabdomyosarcoma, Childhood Salivary Gland Cancer, Salivary Gland Cancer, Childhood Sarcoma, Ewing's Family of Tumors, Sarcoma, Kaposi's, Sarcoma, Soft Tissue, Adult Sarcoma, Soft Tissue, Childhood Sarcoma, Uterine Sezary Syndrome, Skin Cancer (non-Melanoma), Childhood Skin Cancer (Melanoma), Skin Carcinoma, Merkel Cell Small Cell Lung Cancer Small Intestine Cancer Soft Tissue Sarcoma, Adult Soft Tissue Sarcoma, Childhood Squamous Cell Carcinoma, Squamous Neck Cancer with Occult Primary, Metastatic, Stomach (Gastric) Cancer, Childhood Supratentorial Primitive Neuroectodermal Tumors, Childhood T-Cell Lymphoma, Testicular Cancer, Thymoma, Childhood Thymoma and Thymic Carcinoma Thyroid Cancer, Thyroid Cancer, Childhood Transitional Cell Cancer of the Renal Pelvis and Ureter Trophoblastic Tumor, Gestational Unknown Primary Site, Transitional Cell Cancer, Urethral Cancer, Uterine Cancer, Endometrial Uterine Sarcoma, Vaginal Cancer, Visual Pathway and Hypothalamic Glioma, Childhood Vulvar Cancer, Waldenstróm's Macroglobulinemia Wilms' Tumor, etc.;

B) Infections: comprising practically all type of infections, such as infections of bacterial, fungal, and viral origin; or C) Autoimmune diseases: comprising practically all autoimmune diseases mentioned in the web site of the "American Autoimmune Related Diseases Association" [http://www.aarda.org], including multiple sclerosis (MS), Crohn's disease, rheumatoid arthritis, type 1 diabetes mellitus, psoriasis, lupus, ulcerous colitis, vitiligo, coeliac disease, vasculitis, dermatomyositis, polymyositis, thyroiditis (Hashimoto, Graves), myasthenia gravis, Guillain-Barre syndrome, uveitis, flat lichen, temporal arteritis, sarcoidosis, dry syndrome (Sjoegren), bronchial asthma, pemphigus, ankylosing spondilitis, sclerodermia, fibromyalgia, rheumatic fever, etc.

Thus, according to a further aspect, the invention relates to a pharmaceutical composition, hereinafter referred to as the pharmaceutical composition of the invention, comprising a compound of formula I, its substantially pure stereoisomers Ia, Ib, Ic or Id, or mixtures thereof in equimolar ratios or not, wherein said mixture does not contain simultaneously all four stereoisomers of the following compounds: (i) 1-(3-amino-5-carboxy-2-oxopyrrolidin-3-ylmethyl)pyridinium chloride hydrochloride, or (ii) 1-(1-acetyl-3-amino-5-carboxy-2-oxopyrrolidin-3-ylmethyl)pyridinium chloride hydro-chloride, and a pharmaceutically acceptable carrier.

In a particular embodiment, the pharmaceutical composition of the invention comprises, as active ingredient, at least one substantially pure stereoisomer of a compound of formula I, i.e. Ia, Ib, Ic or Id, or mixtures thereof in equimolar ratios or not, wherein said mixture does not contain simultaneously all four stereoisomers of the above mentioned compounds (i) or (ii), in a therapeutically effective amount. In the sense used in this description, the expression "therapeutically effective amount" refers to the quantity of active ingredient calculated to produce the desired effect and will generally be determined, among other reasons, by the own features of the active ingredient used and the therapeutic effect to be obtained. In a particular embodiment, the dose of active ingredient administered to a subject in need of treatment for the treatment and/or prophylaxis of the above mentioned conditions is within the range of $10^{-10}$ to $10^{10}$ mg/kg of body weight, typically between $10^{-3}$ and $10^3$ mg/kg of body weight.

The term "carrier" refers to a diluent, adjuvant, excipient, or vehicle with which the active ingredient is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. Further, the term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

For its administration to a subject, such as a mammal, e.g., a human, in need of treatment, the pharmaceutical composition of the invention may be administered by any appropriate route (via), such as, oral (e.g., oral, sublingual, etc.), parenteral (e.g., subcutaneous, intramuscular, intravenous, intramuscular, etc.), vaginal, rectal, nasal, topical, ophtalmic, etc.

The pharmaceutical composition of the invention, obtained by mixing the active ingredient(s) with the suitable pharmaceutically aceptable carrier(s) may be administered in a plurality of pharmaceutical forms of administration, e.g., solid, liquid, etc. Illustrative, non-limitative examples of said pharmaceutical forms of administration of the pharmaceutical composition of the invention include oral drops (solution, suspension, emulsion, etc.); oral formulations (liquid, solution, suspension, emulsion, gel, paste, powder, etc.); oral lyophilisate; oral gum; powder for oral solution or suspension; granules; gastro-resistant granules; prolonged-release granules; modified-release granules; granules for oral suspension; powder and solvent for oral solution or suspension; syrup; powder for syrup; granules for syrup; tablets (e.g., soluble tablet, dispersible tablet, coated tablet, film-coated tablet, effervescent tablet, orodispersible tablet, gastro-resistant tablet, prolonged-release tablet, modified-release tablet, buccal tablet, chewable tablet, etc.); herbal tea; instant herbal tea; effervescent powder or granules; sachet, capsule (e.g., hard, soft, gastro-resistant hard or soft capsule, prolonged-release hard or soft capsule, modified-release hard or soft capsule, etc.); pillules; continuous-release intraruminal devise; pulsatile-release intraruminal devise; lick blok; pre-mix for medicated feeding staff; pellets, gargle; concentrate for gargle; gargle (powder or tablet for solution); oromucosal solution, suspension, drops, spray, gel, paste, capsule, etc.; sublingual spray, tablet, etc.; mouth wash; gingival solution, gel, paste, etc.; lozenge; compressed lozenge; pastille; dental gel, stick, insert, powder, solution, suspension, emulsion, etc.; toothpaste; cream; gel; ointment; cutaneous paste, foam, spray, solution, suspension, powder, liquid, solution, concentrate for cutaneous solution, suspensión, emulsion, stick, sponge, etc.; plaster; shampoo; solution for iontophoresis; transdermal match; poultice; dip solution, suspension, emulsion, concentrate for dip solution, suspension or emulsion; pour-on solution, suspension or emulsion; spot-on solution; spot-on suspension; spot-on emulsion; teat dip solution; teat dip suspensión; teat dip emulsion; teat spray solution; eye cream; eye gel; eye ointment; eye drops (solution, suspensión, powder and solvent for solution, powder and solvent for suspension, solvent for reconstitution, lotion, solvent for reconstituting a lotion, etc.); ophthalmic insert; ear cream; ear gel; ear ointment; ear drops (solution, suspension, emulsion, powder, etc.); ear spray (solution, suspension, etc.); ear wash (solution, emulsion, etc.); ear tampon; ear stick; nasal cream; nasal gel; nasal ointment; nasal drops (solution, suspension, emulsion, etc.); nasal powder; nasal spray (solution, suspension, emulsion, etc.); nasal wash, nasal stick; vaginal cream; vaginal gel; vaginal ointment; vaginal foam; vaginal solution; vaginal suspensión; vaginal emulsion; tablet for vaginal solution; vaginal hard or soft capsule; vaginal tablet; effervescent vaginal tablet; vaginal derivery system; rectal cream; rectal gel; rectal ointment; rectal foam; rectal solution; rectal suspension; rectal emulsion; concentrate for rectal solution; powder for rectal solution; powder for rectal suspension; tablet for rectal suspension; suppository; rectal capsule; rectal tamponnebuliser solution; nubuliser suspension; powder for nebuliser suspension; powder for nebuliser solution; nebuliser emulsion; pressurise inhalation (solution, suspension, emulsion, etc.); inhalation powder; inhalation powder (hard capsule); inhalation powder, pre-dispensed; inhalation vapour (powder, capsule, solution, tablet, ointment, liquid, etc.); inhalation gas; gel for injection; solution for injection; suspension for injection; emulsion for injection; powder for solution for injection; powder for suspension for injection; powder and solvent for solution for injection; powder and solvent for suspension for injection; concentrate for solution for injection; solution for infusion; emulsion for infusion; powder for solution for infusion; concentrate for solution for infusion; powder and solvent for solution for infusion; implantation tablet; solution for peritoneal dialysis; solution for haemofiltration; solution for haemodiafiltration; solution for haemodialysis; concentrate for haemodialysis solution; solution for intravesical use; bladder irrigation; powder bladder irrigation; urethral gel; urethral stick; endotracheopulmonary instillation (solution); endotracheopulmonary instillation (powder for solution); endotracheopulmonary instillation (uspension); endotracheopulmonary instillation (powder and solvent for solution); endocervical gel; powder and solvent for endocervical gel; intramammary solution; intramammary suspension; intramammary emulsion; intramammary ointment; teat stick; intrauterine delivery system; etc.

The carriers and auxilliary substances necessary to manufacture the desired pharmaceutical form of administration of the pharmaceutical composition of the invention will depend, among other factors, on the elected administration pharmaceutical form. Said pharmaceutical forms of administration of the pharmaceutical composition will be manufactured according to conventional methods known by the skilled person in the art. A review of different active ingredient administration methods, excipients to be used and processes for producing them can be found in "Tratado de Farmacia Galenica", C. Faulí i Trillo, Luzán 5, S. A. de Ediciones, 1993.

In another aspect, the invention relates to the use of a substantially pure stereoisomer of a compound of formula I, i.e. Ia, Ib, Ic or Id, or mixtures thereof in equimolar ratios or not wherein said mixture does not contain simultaneously all four stereoisomers of the following compounds: (i) 1-(3-amino-5-carboxy-2-oxopyrrolidin-3-ylmethyl)pyridinium chloride hydrochloride, or (ii) 1-(1-acetyl-3-amino-5-carboxy-2-oxopyrrolidin-3-ylmethyl)pyridinium chloride hydrochloride, for the manufacture of a pharmaceutical composition for enhancing an immuneresponse in a subject, or for the manufacture of an antitumoral pharmaceutical composition, or for the manufacture of a pharmaceutical composition for treating an infection of bacterial, fungal or viral origin, or for the manufacture of a pharmaceutical composition for treating an autoimmune disease.

According to a preferred embodiment, the present invention is directed to said use for the manufacture of a pharmaceutical composition for the treatment and/or prophylaxis of cancer.

According to a further preferred embodiment, the present invention is directed to said use for the manufacture of a pharmaceutical composition for the treatment and/or prophylaxis of a disease or condition selected form the group consisting of colorectal cancer, breast cancer, prostate cancer, melanoma, mastocytoma, lung cancer and renal cancer.

According to a preferred embodiment, the present invention is directed to said use for the manufacture of a pharmaceutical composition for the treatment and/or prophylaxis of AIDS and related diseases.

Illustrative, non-limitative, examples of conditions susceptible of being treated with the pharmaceutical composition provided by the instant invention include those previously mentioned.

The following examples can be used to illustrate the invention and must not be considered to be limiting of the scope thereof.

EXAMPLES

General Procedures. All melting points were measured in capillary tubes and are uncorrected. IR spectra were determined on KBr disks using a Nicolet Impact 410 spectrometer. 1H NMR spectra were obtained at 300 to 500 MHz on VARIAN UNITY and UNITYPLUS apparatus. Chemical shifts (6) were determined using TMS as internal standard, and multiplicity (s, singlet; d, doublet; dd, double-doublet; t, triplet; q, quartet; m, multiplet) is indicated for every signal. HPLC-MS analyses were performed on an Agilent 1100 apparatus. A chromatographic column Luna C18 (150×4 6 mm) 5 μm Phenomenex was used, with a mobile phase formed by a triple gradient of 4% aq. formic acid (A), water (B) and acetonitrile (C). The gradient started as A (2.5%), B (93%) and C (4.5%) and, in 30 minutes reached A (2.5%), B (4.5%) and (93%). In the Mass detector, the fragmenter operated at 70 eV. Elemental analysis was performed on a LECO CHNS-932 instrument. All yields correspond to isolated pure compounds.

Example 1 relates to the synthesis of (2R-4-methylene-5-oxopyrrolidine-1,2-dicarboxylic acid 1-tertbutyl ester 2-ethyl ester), a starting material of the process of the invention (compound of formula IV).

Example 2 relates to the synthesis of the compound of formula V, a starting material of the process of the invention.

Examples 3 and 4 relate to the synthesis of (3R,5R), (3S,5S), (3R,5S) and (3S,5R)-1-(3-amino-5-carboxy-2-oxopyrrolidin-3-ylmethyl)pyridinium bromide hydro-bromide, which are compounds of formula I, using a one-pot sequence.

Example 5 relates to the one-pot synthesis of 3S,5S-1-(3-amino-5-carboxy-2-oxopyrrolidin-3-ylmethyl)pyridinium bromide hydrobromide following a step-wise synthesis.

Example 6 analyzes the effect of the different isomers of a compound of formula I on tumour growth (tumour assayed: RENCA).

Example 1

Synthesis of a compound of formula IV: (R)-5(2R-4-methylene-5-oxopyrrolidine-1,2-dicarboxylic acid 1-tertbutyl ester 2-ethyl ester)

The synthesis of the title compound is shown in Scheme 1.

1.1 Synthesis of compound 2:
2S-5-oxopyrrolidine-2-carboxylic acid ethyl ester

A 10 L reactor was charged with D-glutamic acid 1 (1 kg, 6.80 mol) in absolute ethanol (5.0 L), cooled to −10° C. and through a dropping-funnel, thionyl chloride (2.0 kg, 14.9 mol) was added slowly over 2 h. After the addition was complete, the mixture was stirred at room temperature for 1 h and then heated to 80° C. for one more hour. The resulting solution was concentrated to dryness (CARE: HCl and $SO_2$ vapours evolved). The residue was diluted with ethanol (2.5 L) and neutralized to pH=7 with addition of a solution of potassium hydroxide in ethanol (10% wt, ca. 2.0 L). The formed solid was removed by filtration and the solution concentrated to give the diethyl ester of 1 as a waxy solid.

The residue was then distilled in vacuo (90° C., 3.1 mbar) for 2 h and the remainder was further heated to 150° C. at 5.2 mbar for 2 h. At room temperature, the residue solidified. Recrystallisation from MTBE/hexane (2:1) gave the desired product 2 as a brownish solid (960 g, 90%). m.p. 49-51° C.

1H-NMR (CDCl3, 300 MHz): 6.82 (bs, 1H); 4.29-4.23 (m, 1H); 4.21 (q, 2H, J=7.3 Hz); 2.48-2.17 (m, 4H); 1.28 (t, 3H, J=7.3 Hz) ppm.

1.2 Synthesis of 3:
2R-5-oxopyrrolidine-1,2-dicarboxylic acid 1-tertbutyl ester 2-ethyl ester To a stirred solution of ethyl pyroglutamate 2 (900 g, 5.73 mol) in dichloromethane (8.0 L) in a reactor, di-tert-butyldicarbonate (2.5 kg, 11.5 mol), triethylamine (800 mL, 5.73 mol) and DMAP (700 g, 5.73 mol) were added, and the reaction stirred for 2 h. The red-brown solution was concentrated to dryness, diluted in ethyl acetate (10.0 L) and washed with aq. HCl 3N (4×2.5 L). The combined organic layers were washed with water (6×2.5 L) and brine (1.0 L), and dried over sodium sulphate. The reaction mixture was concentrated to dryness, cooled in ice and triturated with MTBE and hexane (1:1) to give a brown solid (390 g). Concentration of mother liquors gave an oil (600 g) which, after chromatography ($SiO_2$, hexane/ethyl acetate 3:1) gave a colourless solid (386 g) 3. Total yield (776 g, 54%). m.p. 48-49° C.

1H-NMR (CDCl3, 300 MHz): 4.57 (dd, 1H, J=9.5 Hz, J=3.3 Hz); 4.20 (q, 2H, J=7.3 Hz); 2.72-1.77 (m, 4H); 1.46 (s, 9H); 1.26 (t, 3H, J=7.3 Hz) ppm.

1.3 Synthesis of 4: Mixture of cis- and trans-2R-4-dimethylamino-5-oxopyrrolidine-1,2-dicarboxylic acid 1-tertbutyl ester 2-ethyl ester To a stirred solution of LiHMDS in THF (1M, 0.24 L, 0.24 mol) at −78° C. a solution of 3 (30 g, 0.12 mol) in dry THF (1.0 L) was added slowly. After stirring for 40 min at −78° C., Eschenmoser's salt (45.5 g, 0.24 mol) was added, and stirring continued for a further 20 min. The reaction mixture was allowed to warm to room temperature and stirred for 16 more hours. The mixture was concentrated and the residue partitioned between ethyl acetate (300 mL) and water (300 mL). The aqueous layer was again extracted with ethyl acetate (2×300 mL). The combined organic extract were washed with aqueous HCl 1M (3×150 mL). The acidic layer was immediately neutralized with sodium bicarbonate and extracted with ethyl acetate (3×300 mL). The organic phase was washed with water (300 mL), brine (50 mL), dried over sodium sulphate and concentrated to dryness to give the desired product 4 as a pale brown oil (26.9 g, 72%), which was used directly in the next step.

1H-NMR (CDCl3, 300 MHz): 4.62 (dd, 1H, J=9.4 Hz, J=3.3 Hz); 4.21 (q, 2H, J=7.3 Hz); 4.18-4.07 (m, 1H); 2.57-2.20 (m, 3H); 2.22 (s, 3H); 2.17 (s, 3H); 1.47 (s, 9H); 1.24 (t, 3H, J=7.3 Hz) ppm.

1.4 Synthesis of (R)-5: 2R-4-methylene-5-oxopyrrolidine-1,2-dicarboxylic acid 1-tertbutyl ester 2-ethyl ester An autoclave (4 L) was charged with a solution of 4 (244.9 g, 0.74 mol) in MeOH (2.5 L) and iodomethane (138.2 mL, 2.22 mol). The reaction mixture was stirred at room temperature for 48 h. The solvent was removed and the residue partitioned between ethyl acetate (2 L) and $NaHCO_3$ 10% (1 L). The aqueous phase was again extracted with ethyl acetate (3×500 mL). The combined organic layers were dried over sodium sulphate, filtered and concentrated to dryness. The residue was purified by flash chromatography (hexane/ethyl acetate 4:1-+Ethyl acetate) to obtain (R)-5 as a colourless oil (55.1 g, 27%).

¹H-NMR (CDCl3, 300 MHz): 6.23 (t, 1H, J=2.7 Hz); 5.51 (t, 1H, J=2.2 Hz); 4.61 (dd, 1H, J=10.3 Hz, J=3.3 Hz); 4.22 (q, 2H, J=7.1 Hz); 3.17-3.05 (m, 1H); 2.75-2.64 (m, 1H); 1.47 (s, 9H); 1.23 (t, 3H, J=7.1 Hz) ppm.

Example 2

Synthesis of a compound of formula IV: (R)-5(2R-4-methylene-5-oxopyrrolidine-1,2-dicarboxylic acid 1-tertbutyl ester 2-ethyl ester)

The synthesis of the title compound is shown in Scheme 4 below and includes the three variants for the synthesis of the compound of formula 5 disclosed in the description.

35

Scheme 4

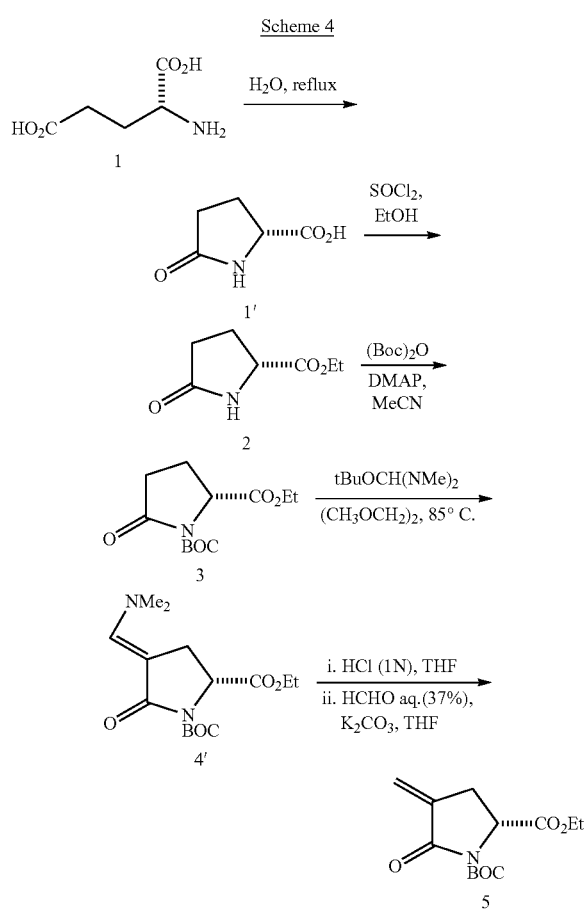

2.1 Synthesis of (2R)-pyroglutamic acid (2')

Method described in Lennox, J. R.; Turner, S. C.; Rapoport, H. *J. Org. Chem.* 2001, 66, 7078-7083

D-Glutamic acid (1) (100 g, 679.7 mmol) in water (400 mL) was heated to reflux while stirring for 72 hours. The resulting clear solution was passed through a Dowex 50wX8 resin column (ion exchange resin in acidic form, 135 g) and washed with water until the eluate is no longer acidic. The combined aqueous eluates were concentrated at 50° C. until 300 mL of distillate has been collected. Methanol (500 mL) was added to assist the removal of the remaining water and to avoid clumping of the solid. The resulting solid was dried in vacuo to afford compound 2' as a white solid (74.63 g, 85%).
m.p. 157° C., $[\alpha]_D^{22}$ +10.5° (c 2.0, $H_2O$),

2.2 Synthesis of ethyl (2R)-pyroglutamate (2)

To a stirred suspension of (2R)-pyroglutamic acid 2' (1 equiv., 2.017 g, 15.62 mmol) in EtOH (2 mL/mmol, 8 mL), $SOCl_2$ (0.1 equiv., 115 μL, 1.56 mmol) was added. The resulting solution was stirred at room temperature for 16 hours. The reaction mixture was neutralized with aqueous 1M $HCO_3Na$. The solvent was concentrated in vacuo and the residue was extracted with AcOEt (3×25 mL). The organic phase was dried over anhydrous $Na_2SO_4$ and concentrated in vacuo. Compound 2 was obtained as a colourless oil which was used in the next step without further purification (79%).

2.3 Synthesis of ethyl (2R)—N-(tert-butoxycarbonyl)pyroglutamate (3)

To a cold (5-10° C.) stirred solution of the ester 2 (1 equiv, 78.6 g, 0.50 mol) and 4-dimethylaminopyridine (DMAP) (0.1

36 equiv., 6.10 g, 50 mmol) in MeCN (0.3 mL/mmol, 180 mL), t-Butyl Dicarbonate $(Boc)_2O$ (1.2 equiv., 131 g, 0.60 mol) was added portionwise (30 minutes). The resulting red solution was stirred at room temperature for 3 hours. Then, the mixture was concentrated in vacuo and the residue was purified by flash chromatography ($EtOAc:CH_2Cl_2$, 1:4) to afford 3 as a yellowish solid (95%). m.p. 48-49° C.

2.4 Synthesis of enaminone (4')

Method described in Dieterich, P.; Young, D. W. *Org. Biomol. Chem.* 2006, 4, 1492-1496

To a solution of pyroglutamate 3 (1 equiv., 83.1 g, 0.32 mol) in 1,2-dimethoxyethane (2.3 mL/mmol, 736 mL), $^tBuOCH(NMe_2)_2$ (Bredereck's reagent, 1.5 equiv., 100 mL, 0.48 mol) was added, and the resulting mixture was heated at 85° C. for 15 hours. The reaction mixture was cooled to room temperature and evaporated in vacuo. The resulting crude oil was triturated in the minimum amount of MTBE and the resulting solid was filtered. Compound 4' was obtained as an orange solid (59.48 g, 59%). Mother-liquids were vacuum concentrated again and successive recristalizations increase the total yield to 84% (84.26 g).

2.5 Synthesis of alkene (5)

Method described in WO 2004039314.

To a solution of 4' (59.48 g, 0.19 mol) in THF (1.56 mL/mmol, 300 mL), aqueous 1 M HCl (1.1 equiv., 210 mL) was added. The mixture was stirred at room temperature for 2 hours. The aqueous and the organic layers were separated, the aqueous phase was discarded, and $K_2CO_3$ (1.4 equiv., 37 g, 0.27 mol) and aqueous HCHO (37%) (1 mL/mmol, 190 mL) were added to the organic layer. The resulting mixture was stirred at room temperature for 45 minutes. The two phases separated and the organic layer was collected and concentrated in vacuo. The resulting crude product was dissolved in (MTBE) methyl$^t$butylether (400 mL), washed with water (200 mL), $Na_2SO_3$ (aqueous 20%, 200 mL) and water (200 mL). The organic layer was dried over anhydrous $Na_2SO_4$, filtered and evaporated in vacuo. Compound 5 was obtained after purification by a short flash chromatography as a colourless oil (20.8 g, 40%).

$^1$H-NMR ($CDCl_3$, 300 MHz): 6.23 (t, 1H, J=2.7 Hz); 5.51 (t, 1H, J=2.2 Hz); 4.61 (dd, 1H, J=10.3 Hz, J=3.3 Hz); 4.22 (q, 2H, J=7.1 Hz); 3.17-3.05 (m, 1H); 2.75-2.64 (m, 1H); 1.47 (s, 9H); 1.23 (t, 3H, J=7.1 Hz) ppm.

Example 3

3.1 Synthesis of a Compound of Formula V: N-Tosyliminobenzyliodinane

The synthesis of the title compound is shown in Scheme 5.

Scheme 5

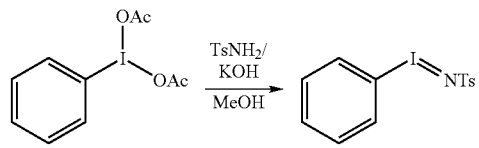

p-Toluensulphonamide (5.13 g), potassium hydroxide (4.20 g) and methanol (120 mL) were stirred in a conical flask in an ice bath, ensuring the reaction mixture was below 10° C. Iodobenzene diacetate (9.60 g) was added to the stirred mixture and the resulting yellow coloured solution was stirred at room temperature for 3.5 hours. The reaction mixture was poured into a large excess of iced water and stirred for 1 hour. A yellow coloured solid precipitated on standing overnight. The light yellow solid was isolated by filtration and dried with a flow of air through the buchner funnel. Several portions of ether, in which the product is insoluble were used to wash away any iodobenzene present. The yellow solid was dissolved in the minimum possible amount of boiling methanol. The solution was placed in a freezer overnight, whereupon an off-white solid was recovered via filtration. (5.1 g, 46%).

3.2 Synthesis of a Compound of Formula V: N-Tosyliminobenzyliodinane

KOH (2.5 equiv, 393 g, 7.00 mol) was added to a solution of p-toluenesulfonamide (1 equiv., 480 g, 2.80 mol) in MeOH (11 L) and the mixture was stirred at room temperature until complete dissolution. The mixture was cooled to 0° C. and Iodobenzene diacetate (1 equiv., 903 g, 2.80 mol) was added and stirred at 0° C. for 40 minutes. The reaction was slowly warmed to 22° C. and stirred overnight. The solid formed was filtered, washed with $Et_2O$ (250 mL) and dried under vacuum at room temperature (285 g). Additonal fractions were obtained when the mother liquids were cooled to 0° C. and a mixture of $H_2O$/ice (5 L) was added slowly. The resulting mixture was stored at 5° C. overnight. Then, the precipitate was filtered, washed with $Et_2O$ (250 mL) and dried under vacuum at room temperature (479 g, 73% combined yield).

Example 4

Synthesis of (3R,5R-1-(3-amino-5-carboxy-2-oxopyrrolidin-3-ylmethyl)pyridinium bromide hydrobromide) 9c and (3S,5R-1-(3-amino-5-carboxy-2-oxopyrrolidin-3-ylmethyl)pyridinium bromide hydrobromide) 9d The synthesis of the title compounds (9c and 9d) is shown in Scheme 6.

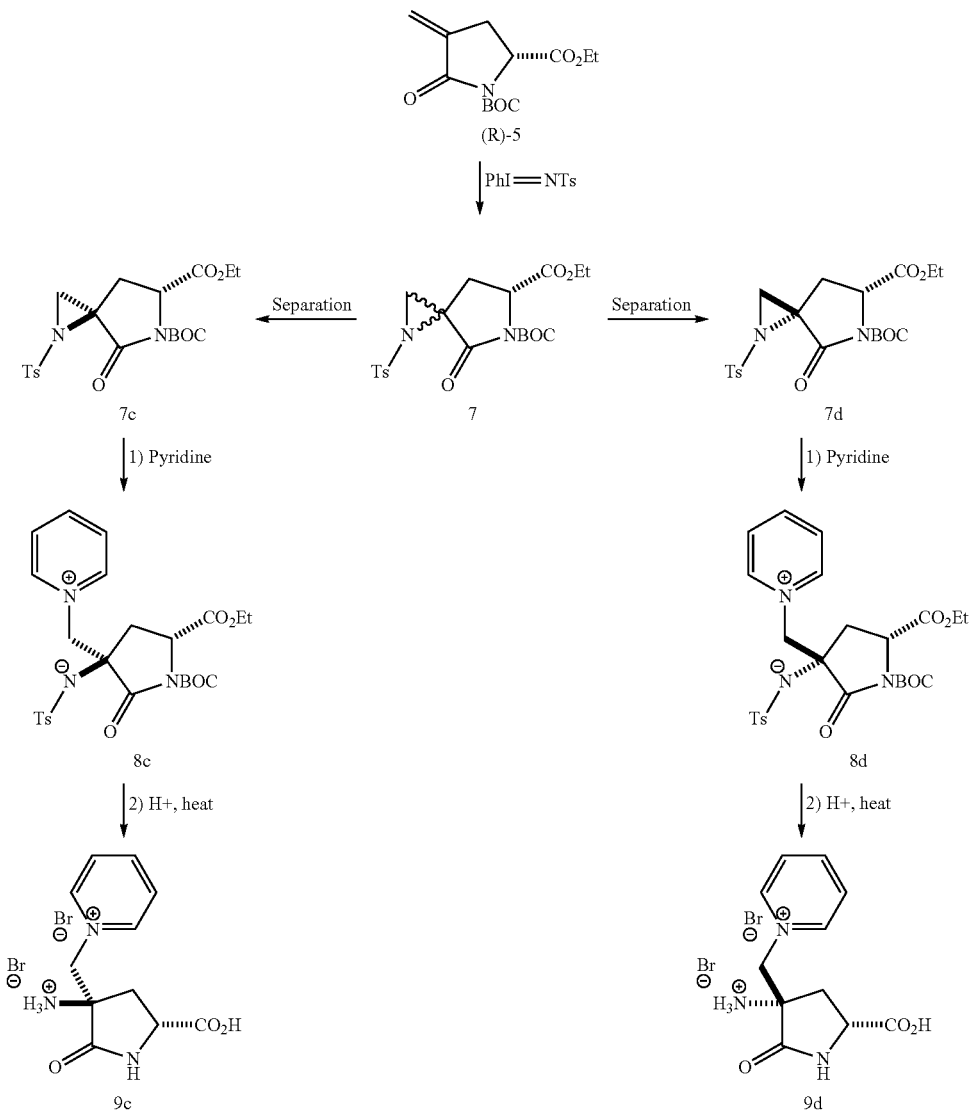

4.1.1 Synthesis of 3R,6R-4-oxo-1-(4-toluenesulfonyl)-1,5-diazaspiro[2,4]heptane-5,6-dicarboxylic acid 5-tertbutylester 6-ethyl ester 7c and 3S,6R-4-oxo-1-(4-toluenesulfonyl)-1,5-diazasiro[2,4]heptane-5,6-dicarboxylic acid 5-tertbutylester 6-ethyl ester 7d To a cold solution (0° C., ice-water bath) of (R)-5 (3.02 g, 11.21 mmol) in dry acetonitrile (12 mL), PhI=NTs (see Example 2) (6.27 g, 16.8 mmol) was added in one portion, followed by Cu(acac)$_2$ (293 mg, 1.12 mmol). The resulting heterogeneous mixture was stirred at 0° C. for 15 minutes, and it was allowed to warm to room temperature and stirred overnight. To the resulting mixture 1M NaOH (50 mL) was added, and the mixture extracted with EtOAc (3×25 mL). The organic layers were then washed with brine (25 mL), dried over anhydrous Na$_2$SO$_4$ and evaporated to dryness. The crude oil was purified by flash chromatography (SiO$_2$, hexanes/EtOAc:2/1) to render the aziridine 7c (730 mg) and 7d (287 mg) as white solids (combined yield: 23%).

7c:
M.p.: 94-95° C.
$[\alpha]_D^{25°\,C.}=+42°$ (0.032, CHCl$_3$)
IR (KBr, cm$^{-1}$): 2977, 2928, 1808, 1746, 1352, 1298, 1251, 1192, 1161, 988, 690.
$^1$H-NMR (CDCl$_3$, 500 MHz) (7c): 7.82 (d, 2H, J=7.3 Hz); 7.31 (d, 2H, J=7.7 Hz); 4.74 (dd, 1H, J=9.7 Hz, J=2.02 Hz); 4.25-4.22 (m, 2H); 3.28 (dd, 1H, J=14.4 Hz, J=9.7 Hz); 2.78 (s, 1H); 2.57 (s, 1H); 2.53 (dd, 1H, J=14.4 Hz, J=2.02 Hz); 2.42 (s, 3H); 1.49 (s, 9H); 1.29 (t, 3H, J=7.0 Hz) ppm.
$^{13}$C (CDCl$_3$, 125 MHz) (7c): 170.5, 166.9, 148.7, 145.1, 135.2, 129.6, 127.9, 84.5, 62.0, 55.5, 47.1, 38.3, 27.7, 25.3, 21.5, 14.0 ppm
MS (ESI+): m/z: 339 (M+1-Boc)

7d:
M.p.: 55-56° C.
$[\alpha]_D^{25°\,C.}=+11°$ (0.036, CHCl$_3$)
IR (KBr, cm$^{-1}$): 2981, 2936, 1799, 1749, 1371, 1330, 1253, 1203, 1156, 1094, 989, 687.
$^1$H-NMR (CDCl$_3$, 500 MHz) (7d): 7.79 (d, 2H, J=8.0 Hz); 7.30 (d, 2H, J=7.7 Hz); 4.70 (dd, 1H, J=9.4 Hz, J=4.3 Hz); 4.30-4.22 (m, 2H); 3.06 (dd, 1H, J=15.1 Hz, J=4.3 Hz); 2.92 (dd, 1H, J=15.4 Hz, J=9.4 Hz); 2.82 (s, 1H); 2.63 (s, 1H); 2.41 (s, 3H); 1.49 (s, 9H); 1.28 (t, 3H, J=7.0 Hz) ppm.
$^{13}$C(CDCl$_3$, 125 MHz) (7d): 169.5, 167.1, 148.9, 145.0, 135.7, 129.6, 127.9, 84.5, 62.1, 56.1, 47.0, 37.1, 27.8, 24.5, 21.6, 14.0 ppm.
MS (ESI+): m/z: 339 (M+1-Boc)

4.1.2 Synthesis of 3S,6R-4-oxo-1-(4-toluenesulfonyl)-1,5-diazaspiro[2,4]heptane-5,6-dicarboxylic acid 5-tertbutylester 6-ethyl ester 7d with improved work-up To a cold solution (0° C., ice-water bath) of (R)-5 (1.84 g, 6.82 mmol) in dry acetonitrile (7 mL) PhI=NTs (3.82 g, 10.2 mmol) was added in one portion, followed by Cu(acac)$_2$ (178 mg, 0.682 mmol). The resulting mixture was stirred at 0° C. for 15 minutes, then it was allowed to warm to room temperature and stirred overnight. The resulting mixture was evaporated in vacuo. The crude oil was purified by flash chromatography (SiO$_2$, CH$_2$Cl$_2$/EtOAc: 9/1) to yield a mixture of aziridines free from p-TsNH$_2$ impurity (determined by HPLC-Ms). The mixture was again cromatographed (SiO$_2$, hexane/EtOAc:2/1) until cis-aziridine 7d was obtained as a pure white foam. (8%).

4.2.1 One-pot synthesis of 3R,5R-1-(3-amino-5-carboxy-2-oxopyrrolidin-3-ylmethyl)pyridinium bromide hydrobromide 9c A mixture of the aziridine 7c (200 mg, 0.46 mmol), montmorillonite MK10 (20% weight, 40 mg) and pyridine (37 μL, 0.46 mmol) was irradiated under microwaves (300 W) at 100° C., and for 10 minutes. The crude mixture was diluted with ethyl acetate [EtOAc] (10 mL), filtered and evaporated under vacuum until HPLC analysis showed no remaining pyridine. The betaine 8c was used in the next step without further purification (93% purity by HPLC). The crude brown oil was dissolved in aqueous 48% HBr (20 mL) and heated under reflux for 18 hours. The mixture was diluted with water and washed with EtOAc (3×10 mL), the aqueous phase was evaporated to dryness. The crude oil was purified by chromatography employing Cellulose powder:SiO$_2$:Cellulose powder:activated charcoal, (1 cm:0.5 cm:0.5 cm:2 cm) as stationary phase, yielding 9c as a solid (51 mg, 28%). M.p.: >200° C.
$[\alpha]_D^{25°\,C.}=+40°$ (0.041, CH$_3$OH)
IR (KBr, cm$^{-1}$): 3434, 3051, 1725, 1633, 1488, 1420, 1384, 1280, 1188, 1145, 1083, 683.
$^1$H-NMR (D$_2$O, 500 MHz) 8.82 (d, 2H, J=5.3 Hz); 8.59 (t, 1H, J=7.8 Hz); 8.09 (t, 2H, J=6.8 Hz); 5.21 (d, 1H, J=14.3 Hz); 4.93 (d, 1H, J=14.3 Hz); 4.24 (t, 1H, J=9.2 Hz); 3.01 (dd, 1H, J=13.9 Hz, J=9.3 Hz); 2.11 (t, 1H, J=7.8 Hz) ppm.
$^{13}$C (D$_2$O, 125 MHz): 173.2, 173.1, 147.1, 145.6, 128.6, 64.4, 64.2, 49.3, 33.0 ppm.
MS (ESI+): m/z: 236 (M+1-2Br).

4.2.2 One-pot synthesis of 3S,5R-1-(3-amino-5-carboxy-2-oxopyrrolidin-3-ylmethyl)pyridinium bromide hydrobromide 9d A mixture of the aziridine 7d (200 mg, 0.46 mmol), montmorillonite MK10 (20% weight, 40 mg) and pyridine (37 μL, 0.46 mmol) was irradiated under microwaves (300 W) at 100° C., and for 10 minutes. The crude mixture was diluted with EtOAc (10 mL), filtered and evaporated under vacuum until HPLC analysis showed no remaining pyridine. The betaine 8d was used in the next step without further purification (93% purity by HPLC). The crude brown oil was dissolved in aqueous 48% HBr (20 mL) and heated under reflux for 18 hours. The mixture was diluted with water and washed with EtOAc (3×10 mL), the aqueous phase was evaporated to dryness. The crude oil was purified by chromatography employing Cellulose powder:SiO$_2$:Cellulose powder:activated charcoal, (1 cm:0.5 cm:0.5 cm:2 cm) as stationary phase, yielding 9d as a solid (52 mg, 28%). M.p.>200° C.
$[\alpha]_D^{25°\,C.}=+40°$ (0.038, CH$_3$OH)
IR (KBr, cm$^{-1}$): 3435, 3051, 1721, 1631, 1509, 1475, 1422, 1384, 1280, 1190, 1144, 683.
$^1$H-NMR (D$_2$O, 500 MHz) 8.76 (d, 2H, J=5.3 Hz); 8.59 (t, 1H, J=7.8 Hz); 8.07 (t, 2H, J=6.8 Hz); 5.19 (d, 1H, J=14.3 Hz); 4.78 (d, 1H, J=14.3 Hz); 4.33 (t, 1H, J=9.2 Hz); 2.90 (dd, 1H, J=13.9 Hz, J=9.3 Hz); 2.46 (t, 1H, J=7.8 Hz) ppm.
$^{13}$C (D$_2$O, 125 MHz): 173.3, 172.4, 147.0, 145.1, 128.5, 65.6, 64.7, 49.3, 33.9 ppm.
MS (ESI+): m/z: 236 (M+1-2Br).

4.2.3 One-pot synthesis of 3S,5R-1-(3-amino-5-carboxy-2-oxopyrrolidin-3-ylmethyl)pyridinium bromide hydrobromide 9d with improved crystallization A mixture of aziridine 7d (100 mg, 0.23 mmol), montmorillonite MK10 (20% weight, 20 mg) and pyridine (18 pt, 0.23 mmol) was heated at 90° C. for 3 hours. The crude mixture was diluted with EtOAc (3 mL), filtered and evaporated under vacuum. The residue was triturated in Et$_2$O, filtered and the betaine 8d was obtained as a brown solid. This compound was dissolved in aqueous 48% HBr (10 mL) and heated under reflux for 18-72 hours. The reaction was monitored by HPLC-Ms analysis. The crude oil was triturated with acetone to yield a brown solid. This solid was dissolved in the minimum amount of MeOH (1 mL) and Et$_2$O or acetone were added until precipitation was observed. The solid was then filtered and dried under vacuum (CARE: the product is highly hygroscopic). The process was repeated twice and the purity of the product was determined by HPLC analysis (80% yield).

Example 5

Synthesis of (3S,5S-1-(3-amino-5-carboxy-2-oxopyrrolidin-3-ylmethyl)pyridinium bromide hydrobromide) 9a and (3R,5S-1-(3-amino-5-carboxy-2-oxopyrrolidin-3-ylmethyl)pyridinium bromide hydrobromide) 9b The synthesis of the title compounds (9a and 9b) is shown in Scheme 7.

5.1 Synthesis of 3S,6S-4-oxo-1-(4-toluenesulfonyl)-1,5-diazaspiro[2,4]heptane-5,6-dicarboxylic acid 5-tertbutylester 6-ethyl ester 7a and 3R,6S-4-oxo-1-(4-toluenesulfonyl)-1,5-diazaspiro[2,4]heptane-5,6-dicarboxylic acid 5-tertbutylester 6-ethyl ester 7b To a cold solution (0° C., ice-water bath) of (S)-5 (1.84 g, 6.82 mmol) in dry acetonitrile (7 mL) PhI=NTs (see Example 2) (3.82 g, 10.2 mmol) was added in one portion, followed by Cu(acac)$_2$ (178 mg, 0.682 mmol). The resulting heterogeneous mixture was stirred at 0° C. for 15 minutes, and it was allowed to warm to room temperature and stirred overnight. To the resulting mixture 1M NaOH (20 mL) was added, and the mixture extracted with EtOAc (3×25 mL). The organic layers were then washed with brine (25 mL), dried over anhydrous Na$_2$SO$_4$ and evaporated to dryness. The crude oil was purified by flash chromatography (SiO$_2$, hexanes/EtOAc:2/1) to render aziridine 7a (641 mg) and 7b (478 mg) as white solids (combined yield: 37%).

7a:
M.p.: 95-96° C. $[\alpha]_D^{25°\,C.}=-57°$ (0.029, CHCl$_3$)

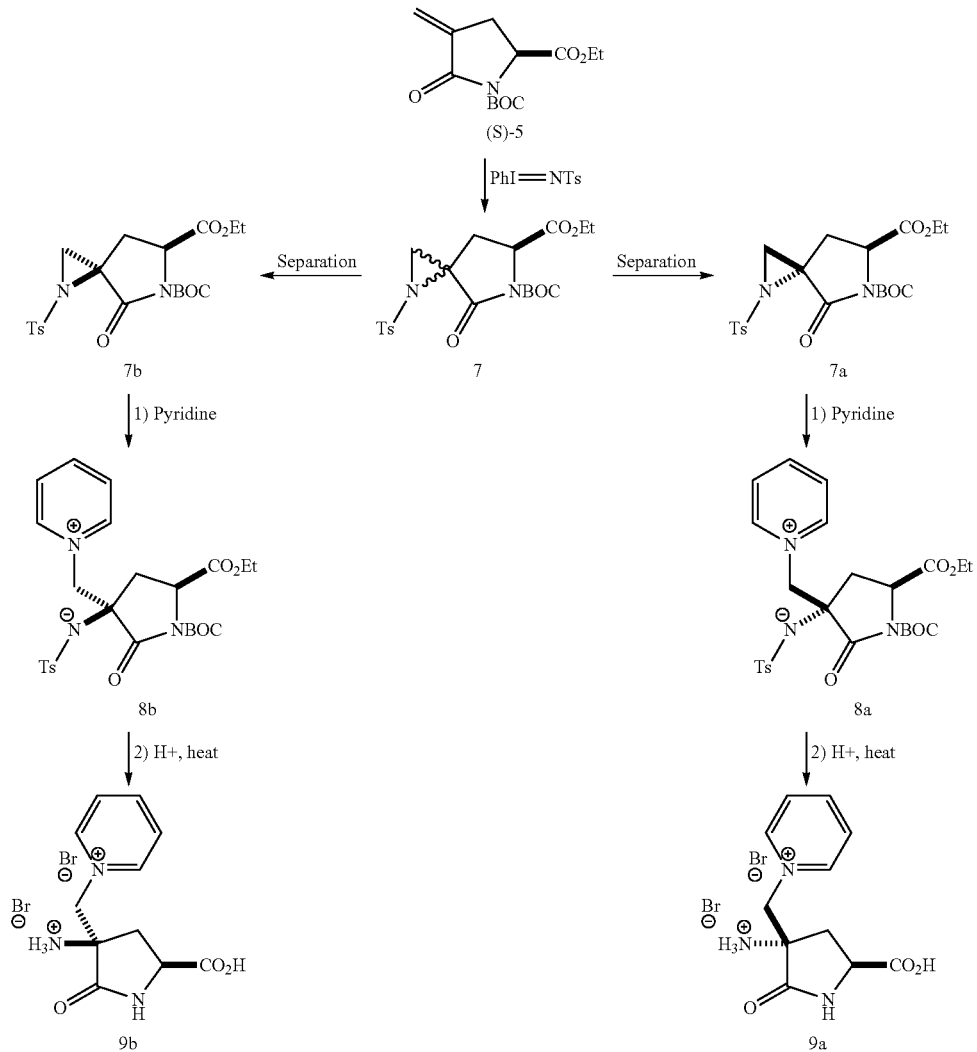

Scheme 7

IR (KBr, cm$^{-1}$): 2977, 2928, 1808, 1746, 1352, 1298, 1251, 1192, 1161, 988, 690.

$^{1}$H-NMR (CDCl$_{3}$, 500 MHz) (7a): 7.77 (d, 2H, J=7.3 Hz); 7.27 (d, 2H, J=7.7 Hz); 4.70 (dd, 1H, J=9.7 Hz, J=2.02 Hz); 4.21-4.17 (m, 2H); 3.22 (dd, 1H, J=14.4 Hz, J=9.7 Hz); 2.75 (s, 1H); 2.51 (s, 1H); 2.49 (dd, 1H, J=14.4 Hz, J=2.02 Hz); 2.37 (s, 3H); 1.45 (s, 9H); 1.27 (t, 3H, J=7.0 Hz) ppm.

$^{13}$C(CDCl$_{3}$, 125 MHz) (7a): 170.5, 166.9, 148.7, 145.1, 135.2, 129.6, 127.9, 84.5, 62.0, 55.5, 47.1, 38.3, 27.7, 25.3, 21.5, 14.0 ppm MS (ESI+): m/z: 339 (M+1-Boc)

7b:

M.p.: 57-58° C.

[α]$_{D}^{25°\ C.}$=−13° (0.068, CHCl$_{3}$)

IR (KBr, cm$^{-1}$): 2982, 2936, 1799, 1749, 1371, 1330, 1252, 1203, 1154, 1093, 989, 687.

$^{1}$H-NMR (CDCl$_{3}$, 500 MHz) (7b): 7.78 (d, 2H, J=8.0 Hz); 7.29 (d, 2H, J=7.7 Hz); 4.70 (dd, 1H, J=9.4 Hz, J=4.3 Hz); 4.29-4.20 (m, 2H); 3.04 (dd, 1H, J=15.1 Hz, J=4.3 Hz); 2.91 (dd, 1H, J=15.4 Hz, J=9.4 Hz); 2.82 (s, 1H); 2.63 (s, 1H); 2.40 (s, 3H); 1.48 (s, 9H); 1.29 (t, 3H, J=7.0 Hz) ppm.

$^{13}$C(CDCl$_{3}$, 125 MHz) (7b): 169.5, 167.1, 148.9, 145.0, 135.7, 129.6, 127.9, 84.5, 62.1, 56.1, 47.0, 37.1, 27.8, 24.5, 21.6, 14.0 ppm.

MS (ESI+): m/z: 339 (M+1-Boc)

5.2.1 One-pot synthesis of 3S,5S-1-(3-amino-5-carboxy-2-oxopyrrolidin-3-ylmethyl)pyridinium bromide hydrobromide 9a A mixture of aziridine 7a (311 mg, 0.71 mmol), montmorillonite MK10 (20% weight, 60 mg) and pyridine (58 µt, 0.71 mmol) was irradiated under microwaves (300 W) at 100° C., and for 10 minutes. The crude mixture was diluted with EtOAc (10 mL), filtered and evaporated under vacuum until HPLC analysis showed no remaining pyridine. The betaine 8a was used in the next step without further purification (93% purity by HPLC).

The crude brown oil was dissolved in aqueous 48% HBr (30 mL) and heated under reflux for 18 hours. The mixture was diluted with water and washed with EtOAc (3×10 mL), the aqueous phase was evaporated to dryness. The crude oil was purified by chromatography employing Cellulose powder:SiO$_{2}$:Cellulose powder:activated charcoal, (1 cm:0.5 cm:0.5 cm:2 cm) as stationary phase, yielding 9a as a solid (110 mg, 40%).

M.p.: >200° C.

[α]$_{D}^{25°\ C.}$=−49° (0.069, CH$_{3}$OH)

IR (KBr, cm$^{-1}$): 3433, 3051, 1724, 1633, 1488, 1420, 1384, 1281, 1188, 1144, 1083, 683.

$^{1}$H-NMR (D$_{2}$O, 500 MHz) 8.82 (d, 2H, J=5.3 Hz); 8.59 (t, 1H, J=7.8 Hz); 8.08 (t, 2H, J=6.8 Hz); 5.23 (d, 1H, J=14.3 Hz); 4.97 (d, 1H, J=14.3 Hz); 4.28 (t, 1H, J=9.2 Hz); 3.06 (dd, 1H, J=13.9 Hz, J=9.3 Hz); 2.13 (t, 1H, J=7.8 Hz) ppm.

$^{13}$C (D$_{2}$O, 125 MHz): 173.1, 172.6, 147.2, 145.6, 128.6, 63.9, 63.7, 49.2, 32.7 ppm.

MS (ESI+): m/z: 236 (M+1-2Br)

5.2.2 One-pot synthesis of 3R,5S-1-(3-amino-5-carboxy-2-oxopyrrolidin-3-ylmethyl)pyridinium bromide hydrobromide 9b A mixture of aziridine 7b (200 mg, 0.46 mmol), montmorillonite MK10 (20% weight, 40 mg) and pyridine (37 µL, 0.46 mmol) was irradiated under microwaves (300 W) at 100° C., and for 10 minutes. The crude mixture was diluted with EtOAc (10 mL), filtered and evaporated under vacuum until HPLC analysis showed no remaining pyridine. The betaine 8b was used in the next step without further purification (93% purity by HPLC). The crude brown oil was dissolved in aqueous 48% HBr (20 mL) and heated under reflux for 18 hours. The mixture was diluted with water and washed with EtOAc (2×10 mL), the aqueous phase was evaporated to dryness. The crude oil was purified by chromatography employing Cellulose powder:SiO$_{2}$:Cellulose powder:activated charcoal, (1 cm:0.5 cm:0.5 cm:2 cm) as stationary phase, yielding 9b as a solid (44 mg, 24%). M.p.>200° C.

[α]$_{D}^{25°\ C.}$=−09° (0.12, CH$_{3}$OH)

IR (KBr, cm$^{-1}$): 3435, 3049, 1724, 1631, 1513, 1475, 1420, 1384, 1280, 1190, 1144, 683.

$^{1}$H-NMR (D$_{2}$O, 500 MHz) 8.82 (d, 2H, J=5.3 Hz); 8.59 (t, 1H, J=7.8 Hz); 8.08 (t, 2H, J=6.8 Hz); 5.23 (d, 1H, J=14.3 Hz); 4.97 (d, 1H, J=14.3 Hz); 4.28 (t, 1H, J=9.2 Hz); 3.06 (dd, 1H, J=13.9 Hz, J=9.3 Hz); 2.13 (t, 1H, J=7.8 Hz) ppm.

$^{13}$C (D$_{2}$O, 125 MHz): 173.4, 172.4, 147.0, 145.0, 128.5, 65.7, 64.8, 49.3, 33.9 ppm.

MS (ESI+): m/z: 236 (M+1-2Br)

Example 6

Stepwise synthesis of 3S,5S-1-(3-amino-5-carboxy-2-oxopyrrolidin-3-ylmethyl)pyridinium bromide hydrobromide

6.1 Synthesis of Betaine 8a

Following the same procedure as in example 5, a mixture of aziridine 7a (311 mg, 0.71 mmol), montmorillonite MK10 (20% weight, 60 mg) and pyridine (58 µL, 0.71 mmol) was irradiated under microwaves (300 W) at 100° C., and for 10 minutes. The crude mixture was diluted with EtOAc (10 mL), filtered and evaporated under vacuum until HPLC analysis showed no remaining pyridine. The betaine 8a was be purified by treatment with diethyl ether, being the product isolated as a white solid.

M.p.: 127-128° C.

IR (KBr, cm$^{-1}$): 3434, 2980, 1786, 1746, 1489, 1370, 1311, 1287, 1199, 1153, 1121, 555.

$^{1}$H-NMR (CDCl$_{3}$, 300 MHz): 9.2 (d, 2H, J=5.6 Hz); 8.3 (t, 1H, J=7.7 Hz); 7.89 (t, 2H, J=6.9 Hz); 7.69 (d, 2H, J=8.0 Hz); 7.10 (d, 2H, J=8.0 Hz); 5.07 (d, 1H, J=13.0 Hz); 4.89 (d, 1H, J=12.6 Hz); 4.27 (t, 2H, J=7.1 Hz); 4.20-4.13 (m, 2H); 2.81 (dd, 1H, J=12.8 Hz, J=7.1 Hz); 2.31 (s, 3H); 2.04-1.98 (m, 1H); 1.38 (s, 9H); 1.25 (t, 3H, J=7.1 Hz) ppm.

MS (ESI+): m/z: 518 (M+1).

Alternatively, the betaine 8a was obtained by heating the same reaction mixture (aziridine 7a (311 mg, 0.71 mmol), montmorillonite MK10 (20% weight, 60 mg) and pyridine (58 µL, 0.71 mmol)) at 90° C. for 7 hours. The crude mixture was diluted with EtOAc (10 mL), filtered and evaporated under vacuum until HPLC analysis showed no remaining pyridine. Yield obtained was similar to the yield obtained using microwaves.

6.2 Synthesis of 3S,5S-1-(3-amino-5-carboxy-2-oxopyrrolidin-3-ylmethyl)pyridinium bromide hydrobromide 9a Pure betaine 8a obtained in the in the previous step was dissolved in aqueous 48% HBr (30 mL) and heated under reflux for 18 hours. The mixture was diluted with water and washed with EtOAc (3×10 mL), the aqueous phase was evaporated to dryness. The crude oil was purified by chromatography employing Cellulose powder:Sift:Cellulose powder:activated charcoal, (1 cm:0.5 cm:0.5 cm:2 cm) as stationary phase, yielding 9a as a solid (110 mg, 40%). M.p.: >200° C.

$[\alpha]_D^{25°\ C.}=-49°$ (0.069, $CH_3OH$)

IR (KBr, $cm^{-1}$): 3433, 3051, 1724, 1633, 1488, 1420, 1384, 1281, 1188, 1144, 1083, 683.

$^1$H-NMR ($D_2O$, 500 MHz) 8.82 (d, 2H, J=5.3 Hz); 8.59 (t, 1H, J=7.8 Hz); 8.08 (t, 2H, J=6.8 Hz); 5.23 (d, 1H, J=14.3 Hz); 4.97 (d, 1H, J=14.3 Hz); 4.28 (t, 1H, J=9.2 Hz); 3.06 (dd, 1H, J=13.9 Hz, J=9.3 Hz); 2.13 (t, 1H, J=7.8 Hz) ppm.

$^{13}$C ($D_2O$, 125 MHz): 173.1, 172.6, 147.2, 145.6, 128.6, 63.9, 63.7, 49.2, 32.7 ppm.

MS (ESI+): m/z: 236 (M+1-2Br).

Example 7

Effect of the Different Isomers (9a, 9b, 9c and 9d) on Tumour Growth

Tumour Assayed: Renca

This assay was made in order to check the effect of each stereoisomer on in vivo tumour growth in mice challenged with Renca cells. Their effect was compared with placebo. The stereoisomers assayed were:

Isomer 1: 3R,5S-1-(3-Amino-5-carboxy-2-oxopyrrolidin-3-ylmethyl)pyridinium bromide hidrobromide (9b)

Isomer 2: 3R,5R-1-(3-Amino-5-carboxy-2-oxopyrrolidin-3-ylmethyl)pyridinium bromide hidrobromide (9c)

Isomer 3: 3S,5S-1-(3-Amino-5-carboxy-2-oxopyrrolidin-3-ylmethyl)pyridinium bromide hidrobromide (9a)

Isomer 4: 3S,5R-1-(3-Amino-5-carboxy-2-oxopyrrolidin-3-ylmethyl)pyridinium bromide hidrobromide (9d)

These isomers can be obtained according to the process disclosed in Examples 4, 5 and 6.

Materials and Methods

Tumor

Renca is a renal cell carcinoma originated in Balb/c mouse strain, and therefore syngeneic in mice with Balb/c genetic background [Melder R J et al., Cancer Immunol. Immunother., 2005, 54:535-547; Felluga B et al., 1969, J. Natl. Cancer Inst. 43:319-333]. Renca is considered a moderate immunogenic tumour and used as suitable model for testing immunointervention approaches [Salup R R, et al., 1992, The Journal of Urology, 147:1120-1123].

Renca cells (CLS, Eppelheim, Germany) were maintained in vitro by serial passages every 3-4 days. Cultures were performed with RPMI medium medium (RPMI, 10% foetal calf serum, 2 mM L-glutamine, non essential amino acids, 1 mM sodium pyruvate, 20 mM HEPES, 80 µg/mL gentamycin; all of them were purchased from Sigma, St. Louis, Mo., USA) by seeding $5 \times 10^6$ cells onto 75 $cm^2$ culture flasks. Tumour cells collected from 48 hour cultures upon trypsinization (Sigma, St. Louis, Mo., USA) were used as source of Renca cells for the studies described below.

Drugs in Study

Active Ingredient

Isomer 1 (9b) at 2.815 mg/mL in sterile physiological saline.

Isomer 2 (9c) at 2.520 mg/mL in sterile physiological saline.

Isomer 3 (9a) at 2.080 mg/mL in sterile physiological saline.

Isomer 4 (9d) at 3.040 mg/mL in sterile physiological saline.

Placebo

Physiological saline (Grifols, Barcelona, Spain)

Mice

| | |
|---|---|
| Animal | Balb/c AnNHsd |
| Justification for the selection | Inbred mouse strain syngeneic with Renca |
| Supplier | CRIFFA - Charles River |
| Number of Study animals | ca. 181 males |
| Age at the start of treatment | 8-10 weeks old |
| Weight | 25-30 g |
| Identification | By means of an ear-punch technique |

Sample Size

According to the previous data the sample size necessary to reach significance was 26 animals per group. This sample size was calculated using Epi-info v6.0 software [Fleiss. Statistical Methods for rates and Proportions. $2^{nd}$ Ed, Wiley, 1981: 38-45] and was estimated for a 0.8 statistical power, with a confidence level of 0.95 for a two-fold decrease in tumour surface and a 1-1 control-case ratio.

Equipment

Laminar flood hood, bath, inverted microscope, counting chamber, $CO_2$ incubator, centrifuge, calliper, balances, adjustable pipettes, nitrogen container, refrigerator/freezer and immunodeficent mice racks.

Reagents

Trypan blue (Sigma, St. Louis, Mo., USA)

Sterile PBS (Sigma, St. Louis, Mo., USA)

Physiological saline (Grifols, Barcelona, Spain)

Dose, Vehicle, Route and Volume Administration

Dose

Each isomer was tested at the dose levels of 260 ng administered on days 6, 7 and 14 after tumour inoculation.

Vehicle

The vehicle in which the isomers were diluted was physiological saline.

Administration Route and Volume

The treatments were given by intraperitoneal route (i.p.). The volume inoculated was 0.2 mL/animal. This route was chosen because it is the one described in the original method [Pérez S, et al., 2003, Clinical Cancer Research. 9:5776-5785].

Study Design

Tumours were established by subcutaneous inoculation in the right hind flank. Mice (Balb/c) were inoculated with 0.2 mL containing $10^5$ viable Renca cells. The day of subcutaneous inoculation will be considered Day 0 of the test.

Balb/c mice inoculated with Renca cells were distributed into 5 experimental groups:

| Group | n | Sex | Treatment | Dose* | Days | Route |
|---|---|---|---|---|---|---|
| (A1) BALB/C | 31 | Male | Placebo (P.S.) | | 6, 7, 14 | i.p. |
| (C1) BALB/C | 30 | Male | isomer 1 | 260 ng | 6, 7, 14 | i.p. |
| (C2) BALB/C | 30 | Male | isomer 2 | 260 ng | 6, 7, 14 | i.p. |
| (C3) BALB/C | 30 | Male | isomer 3 | 260 ng | 6, 7, 14 | i.p. |
| (C4) BALB/C | 30 | Male | isomer 4 | 260 ng | 6, 7, 14 | i.p. |

*Dose per day and mouse

Mice were observed daily and the tumour size recorded twice a week. This was carried out by measuring two perpendicular diameters (L/W) with a calliper. These measures were used to obtain both tumour surface and volume:

Tumour surface=$L \times W(mm^2)$

Tumour volume=$L \times W^2 \times \frac{1}{2}(mm^3)$

Results were expressed as single values and/or as the mean±SD or median from each experimental group.

Statistics

A case-control study was performed with treated and control mice in order to determine whether differences between isomers and administration of placebo were present. The data obtained (tumoral surface and volume) were tested for Normal distribution within the groups—Kolmogorov Smirnov test p<0.05-.A non-parametrical hypothesis test for unpaired samples was performed in order to contrast whether isomers had a deletereouos effect on tumoral growth. The U-test of Mann Withney was chosen for being one of the better known non-parametrical tests, anyway, results for this test are equivalent both to those of Wilcoxon's sum of ranges and Kruskal-Wallis two-groups test.

Due to the high dispersion of data, outlayers (animals beyond percentile 25 or above percentile 75 for tumour surface at day 25) were excluded of the study.

The statistic software used was SPSSv12.0

Results

The Inhibitory Effect of Isomers on Renca Tumour Cell Growth

Thirty mice per group (thirty one from placebo group) were planned to be studied. Two mice from isomer 2 group died for unknown causes the second week after tumour inoculation and were excluded.

Tables 1 and 2 show the results of each experimental group expressed as the median values. These tables summarize the median of surface (Table 1) or volume (Table 2) in isomers or P.S. mice group on each day scored.

TABLE 1

SURFACE ($mm^2$)
Overall values (Median)

| Treatment | Dose ng/mouse | Group | n (first day) | 0 | 11 | 14 | 18 | 21 | 25 |
|---|---|---|---|---|---|---|---|---|---|
| P.S. | — | A1 | 31 | 0 | 0 | 9 | 36 | 64 | 132 |
| isomer 1 | 260 | C1 | 30 | 0 | 0 | 12.5 | 36 | 81 | 160.5 |
| isomer 2 | 260 | C2 | 28 | 0 | 0 | 9 | 42 | 77 | 140 |
| isomer 3 | 260 | C3 | 30 | 0 | 0 | 4 | 18 | 45.5 | 90 |
| isomer 4 | 260 | C4 | 30 | 0 | 0 | 0 | 9 | 25 | 63.5 |

TABLE 2

VOLUME ($mm^3$)
Overall values (Median)

| Treatment | Dose ng/mouse | Group | n (first day) | 0 | 11 | 14 | 18 | 21 | 25 |
|---|---|---|---|---|---|---|---|---|---|
| P.S. | — | A1 | 31 | 0 | 0 | 10 | 108 | 256 | 726 |
| isomer 1 | 260 | C1 | 30 | 0 | 0 | 22.75 | 108 | 329.25 | 907.5 |
| isomer 2 | 260 | C2 | 28 | 0 | 0 | 13.5 | 126 | 278.75 | 613.25 |
| isomer 3 | 260 | C3 | 30 | 0 | 0 | 4 | 36 | 148.75 | 405 |
| isomer 4 | 260 | C4 | 30 | 0 | 0 | 0 | 13.5 | 62.5 | 238.25 |

Tables 3 and 4 show the results of each experimental group expressed as the mean values. These tables summarize the mean of surface (Table 3) or volume (Table 4) in isomers or P.S. mice group on each day scored.

TABLE 3

SURFACE ($mm^2$)
Overall values (Mean)

| Treatment | Dose ng/mouse | Group | n (first day) | 0 | 11 | 14 | 18 | 21 | 25 |
|---|---|---|---|---|---|---|---|---|---|
| P.S. | — | A1 | 31 | 0 | 0.19 | 10.52 | 33.16 | 68.45 | 134.9 |
| isomer 1 | 260 | C1 | 30 | 0 | 1.2 | 14.1 | 44.07 | 86.6 | 149.97 |
| isomer 2 | 260 | C2 | 28 | 0 | 1.6 | 14.46 | 55.14 | 96.86 | 156.53 |
| isomer 3 | 260 | C3 | 30 | 0 | 0.3 | 7.5 | 31 | 64.57 | 106.17 |
| isomer 4 | 260 | C4 | 30 | 0 | 0 | 2.87 | 15.47 | 37.37 | 81.3 |

TABLE 4

VOLUME (mm³)
Overall values (Mean)

| Treatment | Dose ng/mouse | Group | n (first day) | 0 | 11 | 14 | 18 | 21 | 25 |
|---|---|---|---|---|---|---|---|---|---|
| P.S. | — | A1 | 31 | 0 | 0.16 | 24.52 | 106.71 | 312.58 | 816.93 |
| isomer 1 | 260 | C1 | 30 | 0 | 1.73 | 36.88 | 174.37 | 429.07 | 895.58 |
| isomer 2 | 260 | C2 | 28 | 0 | 2.34 | 32.05 | 217.43 | 453.89 | 938.48 |
| isomer 3 | 260 | C3 | 30 | 0 | 0.28 | 14.55 | 101.4 | 278.15 | 557.18 |
| isomer 4 | 260 | C4 | 30 | 0 | 0 | 4.73 | 40.67 | 126.42 | 372.82 |

There were differences in the Renca tumour growth rate among mice receiving isomer 3 vs. placebo. These differences, either in surface or volume, were statistically significant (p<0.05) on days 18th and 25th of tumour development as calculated by Mann-Whitney U test.

There were differences in the Renca tumour growth rate among mice receiving isomer 4 vs. placebo. These differences, either in surface or volume, were statistically significant (p<0.01) all days scored after the day 14th of tumour development as calculated by Mann-Whitney U test.

Figure 2:
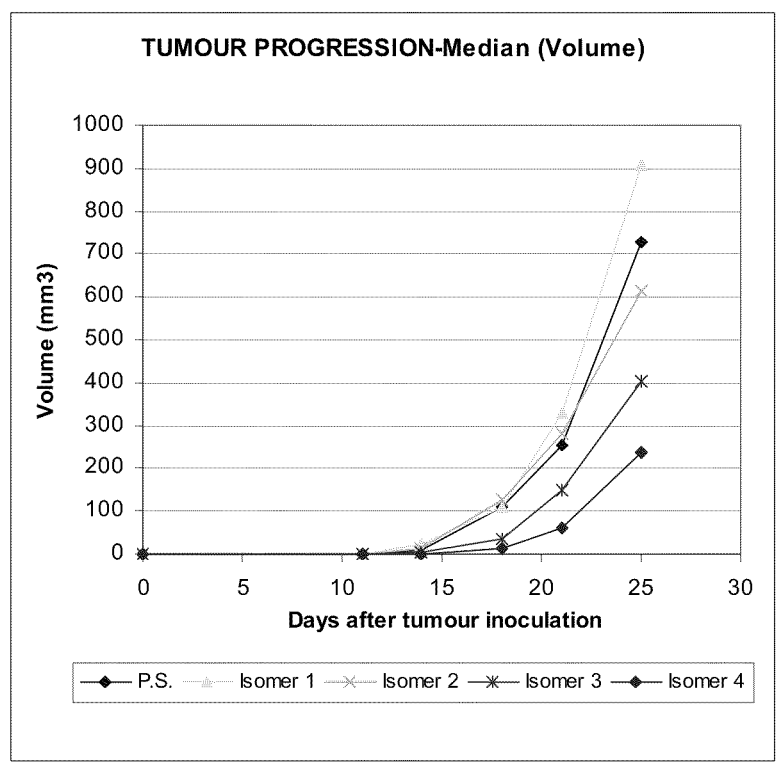
FIG. 2 is a graph showing the inhibitory effect of the isomers (1-4) assayed on Renca tumour cell growth compared to placebo (P.S.) [Example 6], expressed as the median of tumour volumes.

FIG. 1 represents the graph of the median of tumour surfaces (Groups A1, C1, C2, C3, C4) whereas FIG. 2 represents the graph of the median of tumour volumes (Groups A1, C1, C2, C3, C4). As can be seen in these figures there were differences in the Renca tumour growth rate among mice receiving isomer 3 and isomer 4 vs. placebo.

Figure 3:
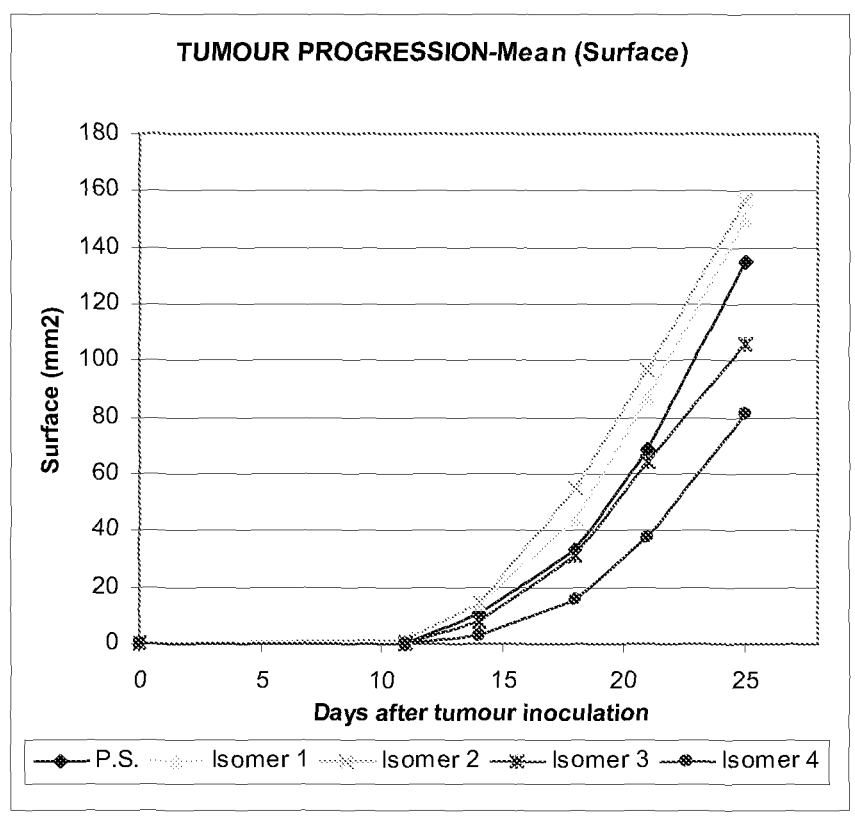
FIG. 3 is a graph showing the inhibitory effect of the isomers (1-4) assayed on Renca tumour cell growth compared to placebo (P.S.) [Example 6], expressed as the mean of tumour surfaces.
Figure 4:
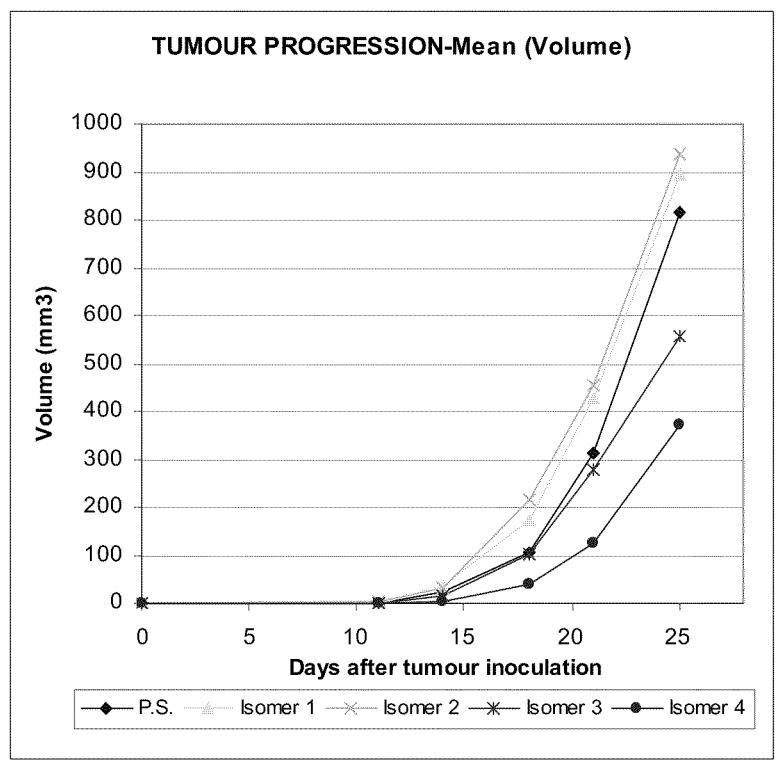
FIG. 4 is a graph showing the inhibitory effect of the isomers (1-4) assayed on Renca tumour cell growth compared to placebo (P.S.) [Example 6], expressed as the mean of tumour volumes.

FIG. 3 represents the graph of mean tumour surfaces (Groups A1, C1, C2, C3, C4) whereas FIG. 4 represents the graph of mean tumour volumes (Groups A1, C1, C2, C3, C4). As can be seen in these figures there were differences in the Renca tumour growth rate among mice receiving isomer 3 and isomer 4 vs. placebo.

The results show that isomer 3 and isomer 4 inhibit the in vivo growth of the renal cell carcinoma (Renca), isomer 4 showing the highest inhibitory effect on Renca tumour growth.

Example 8

Comparison of Tumour Growth Between Different Isomers (9a, 9b, 9c and 9d) and the Mixture of BLAS Tumour Assayed: ASB XIV This assay was made in order to compare the effect of each stereoisomer on in vivo tumour growth in mice with the effect of the mixture of all of them challenged with ASB XIV tumours. The stereoisomers assayed were the same as in example 7 above plus a mixture of all of them (BLAS). The equipment (when needed), reagents, dose, vehicle and route and volume of administration were the same as in example 7.

Materials and Methods

Tumor

ASB XIV is a pulmonary squamous cell carcinoma originated in Balb/c mouse strain, and therefore syngeneic in mice with Balb/c genetic background.

ASB XIV cells (CLS, Eppelheim, Germany) were maintained in vitro by serial passages every 3-4 days. Cultures were performed with RPMI medium medium (RPMI, 10% foetal calf serum, 2 mM L-glutamine, non essential aminoacids, 1 mM sodium pyruvate, 20 mM HEPES, 80 µg/mL gentamycin; all of them were purchased from Sigma, St. Louis, Mo., USA) by seeding $5\times10^6$ cells onto 75 cm² culture flasks. Tumour cells collected from 48 hour cultures upon trypsinization (Sigma, St. Louis, Mo., USA) were used as source of ASB XIV cells in the present example.

Drug in Study

Active Ingredient

BLAS (mixture of isomers 1, 2, 3 and 4) at a concentration of 65 µg/mL in sterile physiological saline. Isomer 1 (9b) at a concentration of 65 µg/mL in sterile physiological saline.

Isomer 2 (9c) at a concentration of 65 µg/mL in sterile physiological saline.

Isomer 3 (9a) at a concentration of 65 µg/mL in sterile physiological saline.

Isomer 4 (9d) at a concentration of 65 µg/mL in sterile physiological saline.

Placebo

Physiologic saline (Grifols, Barcelona, Spain)

Mice

| | |
|---|---|
| Animal | Balb/c AnNHsd |
| Justification for the selection | Inbred mouse strain syngeneic with ASB XIV cells |
| Supplier | CRIFFA - Charles River |
| Number of Study animals | 187 ca. males |
| Age at the start of treatment | 8-10 weeks old |
| Weight | 25-30 g |
| Identification | By means of an ear-punch technique |

Sample Size

According to previous data the sample size necessary to reach significance was 26 animals per group. This sample size was calculated using Epi-info v6.0 software and was estimated for a 0.8 statistical power, with a confidence level of 0.95 for a two-fold decrease in tumour surface and a 1-1 control-case ratio.

Study Design

Tumours were established by subcutaneous inoculation in the right hind flank. Mice (Balb/c) were inoculated with 0.2 mL containing $2\times10^5$ viable ASB XIV cells. The day of subcutaneous inoculation will be considered Day 0 of the test.

Balb/c mice inoculated with ASB XIV cells were distributed into 6 experimental groups:

| Group | n | Sex | Treatment | Dose* | Days | Route |
|---|---|---|---|---|---|---|
| (A1) BALB/C | 32 | Male | Placebo (P.S.) | | 6, 7 and 14 | i.p. |
| | | | | | 6, 7 and 14 | i.p. |
| (B1) BALB/C | 31 | Male | BLAS | 260 ng | 6, 7 and 14 | i.p. |
| | | | | | 6, 7 and 14 | i.p. |
| (C1) BALB/C | 31 | Male | isomer 1 | 260 ng | 6, 7 and 14 | i.p. |
| | | | | | 6, 7 and 14 | i.p. |
| (C2) BALB/C | 31 | Male | isomer 2 | 260 ng | 6, 7 and 14 | i.p. |
| | | | | | 6, 7 and 14 | i.p. |
| (C3) BALB/C | 31 | Male | isomer 3 | 260 ng | 6, 7 and 14 | i.p. |
| | | | | | 6, 7 and 14 | i.p. |
| (C4) BALB/C | 31 | Male | isomer 4 | 260 ng | 6, 7 and 14 | i.p. |

*Dose per day and mouse

Mice were observed daily and the tumour size recorded twice a week. This was carried out by measuring two perpendicular diameters (d1/d2) with a calliper. These measures were used to obtain both tumour surface and volume:

Tumour surface=$d1 \times d2 (mm^2)$

Tumour volume=$d1 \times d2^2 \times \frac{1}{2} (mm^3)$

Results were expressed as single values and/or as the mean±SD or median from each experimental group.

Statistics

A case-control study was performed with treated and control mice in order to determine whether differences between BLAS or each diferent stereoisomer and administration of placebo were present. The data obtained (tumoral surface and volume) were tested for Normal distribution within the groups—Kolmogorov Smirnov test $p<0.05$-.A non-parametrical hypothesis test for unpaired samples was performed in order to contrast whether BLAS had a deletereouos effect on tumoral growth. The U-test of Mann Withney was chosen for being one of the better known non-parametrical tests, anyway, results for this test are equivalent both to those of Wilcoxon's sum of ranges and Kruskal-Wallis two-groups test.

Due to the high dispersion of data, outlayers (animals beyond percentile 10 or above percentile 90 for tumour surface at day 33) were excluded of the study.

The statistic software used was SPSSv12.0

Results

The Inhibitory Effect of BLAS or Each Isomer on ASB XIV Tumour Cell Growth

Thirty one mice per group (thirty two from placebo group) were studied. Two mice from isomer 4 (9d) group died for unknown causes the first week after tumour inoculation and were excluded.

Tables 5 and 6 show the results of each experimental group expressed as the median values. These tables summarize the median of surface or volume in BLAS, isomers or P.S. mice group on each day scored.

TABLE 5

SURFACE ($mm^2$)
Overall values (Median)

| Treatment | Dose ng/mouse | Group | n (first day) | 0 | 8 | 12 | 15 | 19 | 22 | 26 | 29 | 33 |
|---|---|---|---|---|---|---|---|---|---|---|---|---|
| P.S. | — | A1 | 32 | 0 | 0 | 0 | 0 | 16 | 39 | 81 | 120.5 | 161 |
| BLAS | 260 | B1 | 31 | 0 | 0 | 0 | 0 | 9 | 30 | 64 | 81 | 120 |
| Isomer 1 | 260 | C1 | 31 | 0 | 0 | 0 | 0 | 16 | 36 | 72 | 110 | 154 |
| Isomer 2 | 260 | C2 | 31 | 0 | 0 | 0 | 0 | 25 | 56 | 110 | 144 | 210 |
| Isomer 3 | 260 | C3 | 31 | 0 | 0 | 0 | 0 | 9 | 25 | 64 | 99 | 140 |
| Isomer 4 | 260 | C4 | 29 | 0 | 0 | 0 | 0 | 9 | 25 | 49 | 81 | 110 |

TABLE 6

VOLUME ($mm^3$)
Overall values (Median)

| Treatment | Dose ng/mouse | Group | n (first day) | 0 | 8 | 12 | 15 | 19 | 22 | 26 | 29 | 33 |
|---|---|---|---|---|---|---|---|---|---|---|---|---|
| P.S. | — | A1 | 32 | 0 | 0 | 0 | 0 | 32 | 117 | 364.5 | 632.75 | 936 |
| BLAS | 260 | B1 | 31 | 0 | 0 | 0 | 0 | 13.5 | 75 | 245 | 364.5 | 600 |
| Isomer 1 | 260 | C1 | 31 | 0 | 0 | 0 | 0 | 32 | 108 | 288 | 550 | 864 |
| Isomer 2 | 260 | C2 | 31 | 0 | 0 | 0 | 0 | 62.5 | 196 | 550 | 864 | 1436.5 |
| Isomer 3 | 260 | C3 | 31 | 0 | 0 | 0 | 0 | 13.5 | 62.5 | 256 | 445.5 | 700 |
| Isomer 4 | 260 | C4 | 19 | 0 | 0 | 0 | 0 | 13.5 | 62.5 | 171.5 | 364.5 | 550 |

Tables 7 and 8 show the results of each experimental group expressed as the mean values. These tables summarize the mean of surface or volume in BLAS, isomers or P.S. mice group on each day scored.

TABLE 7

SURFACE (mm$^2$)
Overall values (Mean)

| Treatment | Dose ng/mouse | Group | n (first day) | Days after tumour inoculation |  |  |  |  |  |  |  |  |
|---|---|---|---|---|---|---|---|---|---|---|---|---|
|  |  |  |  | 0 | 8 | 12 | 15 | 19 | 22 | 26 | 29 | 33 |
| P.S. | — | A1 | 32 | 0 | 0 | 0.5 | 3.84 | 22.72 | 47.69 | 92.41 | 126.34 | 169.25 |
| BLAS | 260 | B1 | 31 | 0 | 0 | 0.19 | 2.45 | 13.81 | 34.19 | 68.84 | 96.52 | 131.42 |
| Isomer 1 | 260 | C1 | 31 | 0 | 0 | 0.32 | 3.45 | 19.65 | 46.81 | 92.52 | 125.16 | 165.65 |
| Isomer 2 | 260 | C2 | 31 | 0 | 0 | 0.71 | 6.19 | 29.84 | 63.55 | 105.97 | 142.45 | 188.87 |
| Isomer 3 | 260 | C3 | 31 | 0 | 0 | 0.29 | 2.81 | 15.16 | 33.16 | 68.67 | 94.61 | 131.35 |
| Isomer 4 | 260 | C4 | 29 | 0 | 0 | 0.17 | 2.79 | 14.59 | 34.52 | 65.86 | 90.28 | 123.45 |

TABLE 8

VOLUME (mm$^3$)
Overall values (Mean)

| Treatment | Dose ng/mouse | Group | n (first day) | Days after tumour inoculation |  |  |  |  |  |  |  |  |
|---|---|---|---|---|---|---|---|---|---|---|---|---|
|  |  |  |  | 0 | 8 | 12 | 15 | 19 | 22 | 26 | 29 | 33 |
| P.S. | — | A1 | 32 | 0 | 0 | 0.69 | 7.52 | 69.89 | 197.25 | 492.77 | 751.27 | 1165.34 |
| BLAS | 260 | B1 | 31 | 0 | 0 | 0.19 | 4.26 | 34.29 | 116.52 | 322.06 | 511.90 | 806.10 |
| Isomer 1 | 260 | C1 | 31 | 0 | 0 | 0.45 | 5.34 | 53.37 | 179.79 | 474.10 | 733.26 | 1114.37 |
| Isomer 2 | 260 | C2 | 31 | 0 | 0 | 1 | 12.68 | 102.44 | 292.39 | 603.66 | 913.90 | 1377.02 |
| Isomer 3 | 260 | C3 | 31 | 0 | 0 | 0.44 | 6.31 | 44.13 | 116.65 | 337.18 | 529.37 | 848.87 |
| Isomer 4 | 260 | C4 | 29 | 0 | 0 | 0.16 | 5.29 | 36.5 | 118.19 | 297.83 | 451.55 | 700.66 |

There were differences in the ASB XIV tumour growth rate among mice receiving BLAS vs. placebo. These differences, either in surface or volume, were statistically significant ($p<0.05$) all days scored after the day 26th of tumour development as calculated by Mann-Whitney U test.

There were differences in the ASB XIV tumour growth rate among mice receiving Isomer 3 vs. placebo. These differences, either in surface or volume, were statistically significant ($p<0.05$) all days scored after the day 26th of tumour development as calculated by Mann-Whitney U test.

There were differences in the ASB XIV tumour growth rate among mice receiving Isomer 4 vs. placebo. These differences, either in surface or volume, were statistically significant ($p<0.05$) all days scored after the day 26th of tumour development as calculated by Mann-Whitney U test.

BLAS, Isomer 3 and Isomer 4 inhibit the in vivo growth of the lung carcinoma ASB XIV. There were not differences between the inhibitory effect of each one on ASB XIV tumour growth.

Example 9

Comparison of Tumour Growth Between Different Isomers (9a, 9b, 9c and 9d) and the Mixture of BLAS Tumour Assayed: Ehrlich This assay was made in order to compare the effect of each stereoisomer on in vivo tumour growth in mice with the effect of the mixture of all of them challenged with Ehrlich tumours.

The same products, equipment, reagents, doses, vehicle and route of administration as in example 8 were used.

Materials and Methods

Tumor

Mice were inoculated with Ehrlich tumour cells. It was described as a murine mammary adenocarcinoma. Ehrlich tumour is a murine mammary carcinoma originally raised in an outbred mouse, and therefore it belongs to the so-called non-specific tumours (Subiza J L, Viñuela J E, Rodriguez R, Gil J, Figueredo M A, de la Concha. E G. Development of splenic natural suppressor (NS) cells in Ehrlich tumor bearing mice. *Int J Cancer*, 44:307 315; 1989). It may grow across histocompatibility barriers and therefore is not mouse strain specific (Carry P J, Prescott D M, Ogilvie G K. Resistance to Ehrlich ascites tumor in a strain of dystrophic mice. *Cancer Res.*, 39:2139-2140; 1979).

Ehrlich cells were maintained in vitro by serial passages every 3-4 days. Cultures were performed with RPMI medium medium (RPMI, 10% foetal calf serum, 2 mM L-glutamine, non essential aminoacids, 1 mM sodium pyruvate, 20 mM HEPES, 80 µg/mL gentamycin; all of them were purchased from Sigma, St. Louis, Mo., USA) by seeding $5 \times 10^6$ cells onto 75 cm$^2$ culture flasks. Tumour cells collected from 48 hour cultures were used as source of cells for the studies described below.

Mice

| Animal | Balb/c AnNHsd |
|---|---|
| Justification for the selection | Inbred immunocompetent mice strain |
| Supplier | CRIFFA - Charles River |
| Number of Study animals | ca. 96 males |

| | |
|---|---|
| Age at the start of | 8-10 weeks old |
| Weight treatment | 25-30 g |
| Identification | By means of an ear-punch technique |

Study Design

Tumours were established by subcutaneous inoculation in the right hind flank. Mice (Balb/c) were inoculated with 0.2 mL containing $2\times10^5$ viable Ehrlich cells. The day of subcutaneous inoculation will be considered Day 0 of the test.

Balb/c mice inoculated with Ehrlich cells were distributed into 6 experimental groups:

| Group | n | Sex | Treatment | Dose* | Days | Route |
|---|---|---|---|---|---|---|
| (A1) BALB/C | 16 | Male | Placebo (P.S.) | | 6, 7 and 14 6, 7 and 14 | i.p. i.p. |
| (B1) BALB/C | 16 | Male | BLAS | 260 ng | 6, 7 and 14 6, 7 and 14 | i.p. i.p. |
| (C1) BALB/C | 16 | Male | isomer 1 | 260 ng | 6, 7 and 14 6, 7 and 14 | i.p. i.p. |
| (C2) BALB/C | 16 | Male | isomer 2 | 260 ng | 6, 7 and 14 6, 7 and 14 | i.p. i.p. |
| (C3) BALB/C | 16 | Male | isomer 3 | 260 ng | 6, 7 and 14 6, 7 and 14 | i.p. i.p. |
| (C4) BALB/C | 16 | Male | isomer 4 | 260 ng | 6, 7 and 14 6, 7 and 14 | i.p. i.p. |

*Dose per day and mouse

Mice were observed daily and the tumour size recorded twice a week. This was carried out by measuring two perpendicular diameters (L/W) with a calliper. These measures were used to obtain both tumour surface and volume:

Tumour surface=$L \times W$(mm$^2$)

Tumour volume=$L \times W^2 \times \frac{1}{2}$(mm$^3$)

Results were expressed as single values and/or as the mean±SD or median from each experimental group.

Statistics

A case-control study was performed with treated and control mice in order to determine whether differences between BLAS or each diferent stereoisomer and administration of placebo were present. The data obtained (tumoral surface and volume) were tested for Normal distribution within the groups—Kolmogorov Smirnov test p<0.05-.A non-parametrical hypothesis test for unpaired samples was performed in order to contrast whether BLAS had a deletereouos effect on tumoral growth. The U-test of Mann Withney was chosen for being one of the better known non-parametrical tests, anyway, results for this test are equivalent both to those of Wilcoxon's sum of ranges and Kruskal-Wallis two-groups test.

The statistic software used was SPSSv12.0

Results

The Inhibitory Effect of BLAS on Ehrlich Tumour Cell Growth

Sixteen mice per group were planned to be studied.

Tables 9 and 10 show the results of each experimental group expressed as the median values (n (first day) is in all cases 16 and the dosage is 260 ng/mouse). These tables summarize the median of surface or volume in BLAS, isomers or P.S. mice group on each day scored.

TABLE 9

SURFACE (mm$^2$)
Overall values (Median)

| Treatment | Group | Days after tumour inoculation ||||||||||
|---|---|---|---|---|---|---|---|---|---|---|---|
| | | 0 | 8 | 13 | 16 | 20 | 23 | 29 | 31 | 35 | 38 |
| P.S. | A1 | 0 | 10.5 | 25 | 49 | 64 | 84 | 103 | 119 | 138 | 148.5 |
| BLAS | B1 | 0 | 6.5 | 18 | 27.5 | 39 | 49 | 49 | 52.5 | 56 | 64 |
| Isomer 1 | C1 | 0 | 2 | 16 | 20.5 | 27.5 | 39.5 | 39.5 | 46.5 | 52.5 | 53 |
| Isomer 2 | C2 | 0 | 4 | 16 | 20 | 27.5 | 33 | 42 | 45 | 51 | 71 |
| Isomer 3 | C3 | 0 | 0 | 9 | 16 | 20 | 25 | 27.5 | 36 | 43 | 49.5 |
| Isomer 4 | C4 | 0 | 0 | 12.5 | 18 | 27.5 | 39 | 45 | 48.5 | 52.5 | 68 |

TABLE 10

VOLUME (mm$^3$)
Overall values (Median)

| Treatment | Group | Days after tumour inoculation ||||||||||
|---|---|---|---|---|---|---|---|---|---|---|---|
| | | 0 | 8 | 13 | 16 | 20 | 23 | 29 | 31 | 35 | 38 |
| P.S. | A1 | 0 | 15.75 | 62.5 | 171.5 | 256 | 336 | 455.25 | 575 | 675 | 815 |
| BLAS | B1 | 0 | 8.75 | 36 | 68.75 | 117 | 171.5 | 171.5 | 183.75 | 198 | 232 |
| Isomer 1 | C1 | 0 | 2 | 32 | 47.25 | 68.75 | 123.25 | 123.25 | 147.75 | 173.25 | 191 |
| Isomer 2 | C2 | 0 | 4 | 32 | 40 | 68.75 | 91.5 | 126 | 135 | 153 | 266.5 |
| Isomer 3 | C3 | 0 | 0 | 13.5 | 32 | 40 | 62.5 | 68.75 | 100.5 | 135.5 | 164.25 |
| Isomer 4 | C4 | 0 | 0 | 22.75 | 36 | 68.75 | 117 | 135 | 157.75 | 183.75 | 272 |

Tables 11 and 12 show the results of each experimental group expressed as the mean values (n (first day) is in all cases 16 and the dosage is 260 ng/mouse). These tables summarize the mean of surface or volume in BLAS, isomers or P.S. mice group on each day scored.

TABLE 11

SURFACE (mm²)
Overall values (Mean)

| Treatment | Group | Days after tumour inoculation | | | | | | | | | |
|---|---|---|---|---|---|---|---|---|---|---|---|
| | | 0 | 8 | 13 | 16 | 20 | 23 | 29 | 31 | 35 | 38 |
| P.S. | A1 | 0 | 9.19 | 27.5 | 44 | 64.19 | 80.31 | 98.25 | 111.5 | 125.87 | 147.62 |
| BLAS | B1 | 0 | 6.81 | 19.81 | 30.31 | 41.75 | 51.5 | 59.87 | 65 | 74.19 | 87.81 |
| Isomer 1 | C1 | 0 | 5.69 | 13.69 | 20.875 | 32.37 | 42.12 | 50 | 57 | 68.87 | 78.81 |
| Isomer 2 | C2 | 0 | 6.69 | 14.81 | 20.37 | 28.37 | 35.75 | 46.12 | 50.06 | 60.25 | 75.37 |
| Isomer 3 | C3 | 0 | 3.62 | 10.94 | 16.5 | 24.12 | 32.25 | 42.94 | 53.37 | 66 | 79.37 |
| Isomer 4 | C4 | 0 | 3.37 | 12.44 | 20.19 | 31.31 | 43.06 | 52.94 | 63.12 | 76.31 | 91.56 |

TABLE 12

VOLUME (mm³)
Overall values (Mean)

| Treatment | Group | Days after tumour inoculation | | | | | | | | | |
|---|---|---|---|---|---|---|---|---|---|---|---|
| | | 0 | 8 | 13 | 16 | 20 | 23 | 29 | 31 | 35 | 38 |
| P.S. | A1 | 0 | 17.34 | 73.56 | 149.75 | 263.09 | 356.34 | 470.81 | 571.25 | 691.75 | 899.12 |
| BLAS | B1 | 0 | 11.91 | 46.22 | 86.53 | 140.81 | 191.94 | 237.31 | 274.87 | 339.66 | 437.41 |
| Isomer 1 | C1 | 0 | 9.91 | 31.34 | 53.12 | 105.19 | 160.5 | 202.19 | 249.06 | 342.94 | 425.91 |
| Isomer 2 | C2 | 0 | 10.97 | 32.16 | 51.87 | 81.81 | 113.75 | 167 | 191.91 | 258.06 | 372.5 |
| Isomer 3 | C3 | 0 | 6 | 23.53 | 37.12 | 65.12 | 100.44 | 156.34 | 213.31 | 293.87 | 387.69 |
| Isomer 4 | C4 | 0 | 5.94 | 26.91 | 50.34 | 95.59 | 156.53 | 214.91 | 274.94 | 379.72 | 504.22 |

There were differences in the Ehrlich tumour growth rate among mice receiving BLAS vs. placebo. These differences, either in surface or volume, were statistically significant ($p<0.05$) all days scored after the day 16th of tumour development as calculated by Mann-Whitney U test. On days 35th and 38th a tendency was observed in surface ($p=0.056$ and $p=0.08$, respectively). On days $13^{th}$, $16^{th}$, 20th and 38th a tendency was observed in volume ($p=0.08$, $p=0.056$ $p=0.051$ and $p=0.067$, respectively).

There were differences in the Ehrlich tumour growth rate among mice receiving isomer 1 vs. placebo. These differences, either in surface or volume, were statistically significant ($p<0.05$) all days scored after the day 13th of tumour development as calculated by Mann-Whitney U test.

There were differences in the Ehrlich tumour growth rate among mice receiving isomer 2 vs. placebo. These differences, either in surface or volume, were statistically significant ($p<0.05$) all days scored after the day 13th of tumour development as calculated by Mann-Whitney U test.

There were differences in the Ehrlich tumour growth rate among mice receiving isomer 3 vs. placebo. These differences, either in surface or volume, were statistically significant ($p<0.05$) all days scored after the day 8th of tumour development as calculated by Mann-Whitney U test.

There were differences in the Ehrlich tumour growth rate among mice receiving isomer 4 vs. placebo. These differences, either in surface or volume, were statistically significant ($p<0.05$) all days scored after the day 8th of tumour development as calculated by Mann-Whitney U test. A tendency was observed 35th and 38th, either in surface and volume ($p=0.061$ and $p=0.08$, respectively; $p=0.102$, both of them).

There were differences in the Ehrlich tumour growth rate among mice receiving BLAS vs. isomer 3. These differences, either in surface or volume, were statistically significant ($p<0.05$) on days 13th, 16th, 20th and 23th of tumour development as calculated by Mann-Whitney U test.

BLAS, isomer 1, isomer 2, isomer 3 and isomer 4 inhibit the in vivo growth of Ehrlich tumour cells. Isomer 3 shows the highest inhibitory effect on Ehrlich tumour growth.

Example 10

Effect of Isomer 4 (9d) on Growth of Different Tumours

The following assays were made in order to check the effect of isomer 4 (9d) on different tumours following methods and materials analogous to those used in examples 8 and 9, In all cases sterile physiologic saline (Grifols, Barcelona, Spain) was used as placebo. Isomer 4 (9d) was tested at the dose levels indicated in Table 13 on days 6, 7 and 14 after tumour inoculation. In all cases the vehicle was physiologic saline and the treatments were given by intraperitoneal route. The volume inoculated was 0.2 mL/animal. Results are shown in Table 13.

TABLE 13

| Tumour | Mice (size sample) | Dose (ng/mice) | Tumour growth inhibition? |
|---|---|---|---|
| CT26.wt (high dose colon carcinoma) | Balbc/cByl (40 c.a. males) | 250 | YES |
| CT26.CL25 (Low dose colon carcinoma) | Balbc/cByl (40 c.a. males) | 250 | YES |
| Mm5MT (Breast tumour) | C3H/HeN (42 males) | 250 | YES |
| KLN 205 (high dose lung carcinoma) | DBA/2NCrI (62 c.a. males) | 260 | YES |
| ASB XIV (high dose lung carcinoma) | Balb/cAnNCrI (61 males) | 260 | YES |

TABLE 13-continued

| Tumour | Mice (size sample) | Dose (ng/mice) | Tumour growth inhibition? |
|---|---|---|---|
| ASB XIV (low dose lung carcinoma) | Balb/cAnNCrI (62 males) | 260 | YES |
| Lewis (low dose lung carcinoma) | C57BL/6NCrI (62 males) | 260 | YES |
| P-815 (Mastocytoma) | DBA/2NCrI (42 males) | 250 | YES |

Examples 11, 12 and 13

Effect of Isomer 4 (9d) vs Placebo and Combinations of 9d+Cisplatin

Tumours Assayed: KLN 205 and Lewis Lung Cell

This assay was made in order to compare the effect of isomer 4 (9d) on in vivo tumour growth in mice with the effect of the mixture of isomer 4 (9d)+Cisplatin challenged with KLN 205 tumours and Lewis lung cells. The same equipment, reagents, vehicle, and route and volume of administration was used as those used in example 7.

Drugs in Study

In examples 11, 12 and 13 the following drugs where in study:

Active Ingredient

Cisplatin (Sigma, St. Louis, Mo., USA) in sterile physiological saline.

Isomer (9d) (3S,5R-1-(3-Amino-5-carboxy-2-oxopyrrolidin-3-ylmethyl)pyridinium bromide hidrobromide) in sterile physiological saline.

Placebo

Physiologic saline (Grifols, Barcelona, Spain)

In Examples 11, 12 and 13 Mice were observed daily and the tumour size recorded twice a week. This was carried out by measuring two perpendicular diameters (d1/d2) with a calliper. These measures were used to obtain both tumour surface and volume:

Tumour surface=$d1 \times d2$(mm$^2$)

Tumour volume=$d1 \times d2^2 \times \frac{1}{2}$(mm$^3$)

Results were expressed as single values and/or as the mean±SD or median from each experimental group.

Example 11

Effect of 9d in Combination with Cisplatin on Tumour Growth

Tumor Assayed: KLN 205

This assay was made in order to check the effect on in vivo tumour growth in mice challenged with KLN 205 cells. Their effect was compared with the combination of Cisplatin plus 9d and/or placebo.

Materials and Methods

Tumor

KLN 205 is a lung cell carcinoma originated in DBA/2 mouse strain, and therefore syngeneic in mice with DBA/2 genetic background (Kaneko T and LePage G A. Growth characteristics and drug responses of a murine lung carcinoma in vitro and in vivo. *Cancer Res.* 38: 2084-2090; 1978).

KLN 205 cells (CLS, Eppelheim, Germany) were maintained in vitro by serial passages every 3-4 days. Cultures were performed with RPMI medium (RPMI, 10% foetal calf serum, 2 mM L-glutamine, non essential aminoacids, 1 mM sodium pyruvate, 20 mM HEPES, 80 μg/mL gentamycin; all of them were purchased from Sigma, St. Louis, Mo., USA) by seeding $5 \times 10^6$ cells onto 75 cm$^2$ culture flasks. Subcultures were carried out by collecting detached cells after treatment with trypsin-EDTA (Sigma, St. Louis, Mo., USA). Tumour cells, collected from 48 hour cultures, were used as source of KLN 205 cells for the studies described below.

Mice

| Animal | DBA/2NCrI |
|---|---|
| Justification for the selection | Inbred mouse strain syngeneic with KLN 205 cells |
| Supplier | CRIFFA - Charles River |
| Number of Study animals | ca. 62 males |
| Age at the start of treatment | 8-10 weeks old |
| Weight | 25-30 g |
| Identification | By means of an ear-punch technique |

Dose

Cisplatin was tested at the dose levels of 65 μg administrated twice a week for three weeks after tumour inoculation.

Isomer 4 (9d) was tested at the dose levels of 250 ng administrated twice a week for three weeks after tumour inoculation.

Study Design

Tumours were established by subcutaneous inoculation in the right hind flank. Mice (DBA/2) were inoculated with 0.2 mL containing $2 \times 10^5$ viable KLN 205 cells. The day of subcutaneous inoculation will be considered Day 0 of the test.

DBA/2 mice inoculated with KLN 205 cells were distributed into 6 experimental groups:

| Group | n | Sex | Treatment | Dose* | Days | Route |
|---|---|---|---|---|---|---|
| (A1) DBA/2 | 16 | Male | Placebo (P.S.) | — | 3, 6, 10, 13, 17, 20 | ip. |
| (B1) DBA/2 | 16 | Male | 9d | 250 ng | | |
| (C1) DBA/2 | 15 | Male | Cisplatin | 65 μg | | |
| (D1) DBA/2 | 15 | Male | 9d | 250 ng | | |
| | | | Cisplatin | 65 μg | | |

*Dose per day and mouse

Statistics

A case-control study was performed with treated and control mice in order to determine whether differences between placebo, 9d, Cisplatin or 9d+Cisplatin were present. The data obtained (tumoral surface and volume) were tested for Normal distribution within the groups—Kolmogorov Smirnov test $p<0.05$-. A parametrical hypothesis test for unpaired samples was performed in order to contrast whether 9d and/or cisplatin had a sinergic effect on tumoral growth. The t-test was chosen for being one of the better known parametrical tests.

The statistic software used was SPSSv12.0

Results

The Inhibitory Effect of 9d and/or Ciplatin on KLN 205 Tumour Cell Growth

Sixteen or fifteen mice per group were planned to be studied.

Tables 14 and 15 show the results of each experimental group expressed as the median values. These tables summarize the median of surface or volume in 9d, Cisplatin, 9d+Cisplatin or P.S. mice group on each day scored.

TABLE 14

SURFACE (mm²)
Overall values (Median)

| Treatment | Dose | Group | n (first day) | \multicolumn{10}{c}{Days after tumour inoculation} |
|---|---|---|---|---|---|---|---|---|---|---|---|---|---|

| Treatment | Dose | Group | n (first day) | 0 | 10 | 13 | 17 | 20 | 24 | 27 | 31 | 34 | 38 |
|---|---|---|---|---|---|---|---|---|---|---|---|---|---|
| P.S. | — | A1 | 16 | 0 | 0.5 | 12.5 | 30.5 | 49 | 80.5 | 114.5 | 174 | 210 | 270.5 |
| 9d | 250 ng | B1 | 16 | 0 | 4 | 16 | 25 | 36 | 64 | 105.5 | 132.5 | 170.5 | 227.5 |
| Cisplatin | 65 µg | C1 | 15 | 0 | 4 | 16 | 20 | 36 | 72 | 99 | 120 | 150 | 198 |
| 9d + Cisplatin | 250 ng + 65 µg | D1 | 15 | 0 | 4 | 9 | 16 | 25 | 42 | 63 | 81 | 100 | 132 |

TABLE 15

VOLUME (mm³)
Overall values (Median)

| Treatment | Dose | Group | n (first day) | 0 | 10 | 13 | 17 | 20 | 24 | 27 | 31 | 34 | 38 |
|---|---|---|---|---|---|---|---|---|---|---|---|---|---|
| P.S. | — | A1 | 16 | 0 | 0.25 | 22.75 | 85.25 | 171.5 | 342.25 | 582.75 | 1044 | 1477.5 | 2007 |
| 9d | 250 ng | B1 | 16 | 0 | 4 | 32 | 62.5 | 108 | 256 | 446.75 | 628.75 | 937.75 | 1478.8 |
| Cisplatin | 65 µg | C1 | 15 | 0 | 4 | 32 | 40 | 108 | 288 | 445.5 | 600 | 800 | 1089 |
| 9d + Cisplatin | 250 ng + 65 µg | D1 | 15 | 0 | 4 | 13.5 | 32 | 62.5 | 126 | 220.5 | 364.5 | 500 | 700 |

Tables 16 and 17 show the results of each experimental group expressed as the mean values. These tables summarize the mean of surface or volume in 9d, Cisplatin, 9d+Cisplatin or P.S. mice group on each day scored.

TABLE 16

SURFACE (mm²)
Overall values (Mean)

| Treatment | Dose | Group | n (first day) | 0 | 10 | 13 | 17 | 20 | 24 | 27 | 31 | 34 | 38 |
|---|---|---|---|---|---|---|---|---|---|---|---|---|---|
| P.S. | — | A1 | 16 | 0 | 3.63 | 17.44 | 40.81 | 70.56 | 104.69 | 141.75 | 187.25 | 221.69 | 275.31 |
| 9d | 250 ng | B1 | 16 | 0 | 5.38 | 17.25 | 29.88 | 57.06 | 81.38 | 113.5 | 135.31 | 168.81 | 214.44 |
| Cisplatin | 65 µg | C1 | 15 | 0 | 4.07 | 14.87 | 23.93 | 39.07 | 72.2 | 97.07 | 124.67 | 147.93 | 185.33 |
| 9d + Cisplatin | 250 ng + 65 µg | D1 | 15 | 0 | 3.2 | 10.6 | 18.47 | 31.07 | 47.2 | 65.8 | 85.73 | 105.73 | 136.87 |

TABLE 17

VOLUME (mm³)
Overall values (Mean)

| Treatment | Dose | Group | n (first day) | 0 | 10 | 13 | 17 | 20 | 24 | 27 | 31 | 34 | 38 |
|---|---|---|---|---|---|---|---|---|---|---|---|---|---|
| P.S. | — | A1 | 16 | 0 | 7.12 | 48.41 | 151.16 | 324.47 | 539.84 | 813.44 | 1213.9 | 1584.0 | 2166.8 |
| 9d | 250 ng | B1 | 16 | 0 | 8.81 | 43.38 | 94.56 | 246.03 | 393.25 | 611.75 | 777.53 | 1068.3 | 1504.7 |
| Cisplatin | 65 µg | C1 | 15 | 0 | 5.1 | 31.77 | 59.1 | 119.07 | 285.43 | 445.8 | 637.07 | 809.03 | 1129.9 |
| 9d + Cisplatin | 250 ng + 65 µg | D1 | 15 | 0 | 3.73 | 19.77 | 42.17 | 93.4 | 170.07 | 267.57 | 377.67 | 514 | 740.3 |

There were differences in KLN 205 tumour growth rate among mice receiving 9d+Cisplatin vs. placebo. These differences, either in surface or volume, were statistically significant ($p<0.05$) all days scored after the day 17th of tumour development as calculated by t-test.

There were differences in KLN 205 tumour growth rate among mice receiving Cisplatin vs. placebo. These differences, either in surface or volume, were statistically significant ($p<0.05$) all days scored after day 20th of tumour development as calculated by t-test.

There were not differences in KLN 205 tumour growth rate among mice receiving 9d vs. placebo. There was a significant tendency, either in surface or volume, all days scored after day 31th of tumour development as calculated by t-test.

Thus, cisplatin and 9d or Cisplatin inhibit the in vivo growth of KLN 205 cell. 9d and Cisplatin have a sinergic effect.

Example 12

Effect of Isomer (9d) in Combination with Cisplatin on Tumour Growth Through Subcutaneous, Intradermal or Intramuscular Inoculation Tumor Assayed: KLN 205

This assay was made in order to check the effect on in vivo tumour growth in mice challenged with KLN 205 cells. Tumours where established by subcutaneous, intradermal or intramuscular inoculation.

The effect of the combination of cisplatin and/or Isomer (9d) was compared with placebo in mice challenged intradermally. Moreover, the effect of 9d on in vivo tumour growth in mice challenged by intramuscular or subcutaneous route was compared with placebo.

Materials and Methods

Tumor

KLN 205 is a lung cell carcinoma originated in DBA/2 mouse strain, and therefore syngeneic in mice with DBA/2 genetic background (Kaneko T and LePage G A. Growth characteristics and drug responses of a murine lung carcinoma in vitro and in vivo. *Cancer Research*. 38: 2084-2090; 1978).

KLN 205 cells (CLS, Eppelheim, Germany) were maintained in vitro by serial passages every 3-4 days. Cultures were performed with RPMI medium (RPMI, 10% foetal calf serum, 2 mM L-glutamine, non essential aminoacids, 1 mM sodium pyruvate, 20 mM HEPES, 80 µg/mL gentamycin; all of them were purchased from Sigma, St. Louis, Mo., USA) by seeding $5 \times 10^6$ cells onto 75 cm$^2$ culture flasks. Subcultures were carried out by collecting detached cells after treatment with trypsin-EDTA (Sigma, St. Louis, Mo., USA). Tumour cells, collected from 48 hour cultures, were used as source of KLN 205 cells for the studies described below.

Mice

| | |
|---|---|
| Animal | DBA/2NCrI |
| Justification for the selection | Inbred mouse strain syngeneic with KLN 205 cells |
| Supplier | CRIFFA - Charles River |
| Number of Study animals | ca. 80 males |
| Age at the start of treatment | 8-10 weeks old |
| Weight | 25-30 g |
| Identification | By means of an ear-punch technique |

Dose

Cisplatin was tested at the dose levels of 65 µg administrated on days 7, 11, 14, 18, 21, 25 and 28 after tumour inoculation.

Isomer (9d) was tested at the dose levels of 250 ng administrated on days 7, 11, 14, 18, 21, and 28 after tumour inoculation.

Study Design

Tumours were established by subcutaneous and intradermal inoculation in the right hind flank, and intramuscular in the right hind leg. Mice (DBA/2) were inoculated with 0.05 mL containing $2 \times 10^5$ viable KLN 205 cells. The day of subcutaneous, intradermal and intramuscular inoculation will be considered Day 0 of the test.

DBA/2 mice inoculated with KLN 205 cells were distributed into 8 experimental groups:

| Group | n | Sex | Inoculation route | Treatment | Dose* | Days** | Route |
|---|---|---|---|---|---|---|---|
| (A1) DBA/2 | 10 | Male | subcutaneous | Placebo (P.S.) | — | 7, 11, 14, 18, 21, 25 and 28 | ip. |
| (A2) DBA/2 | 10 | Male | subcutaneous | 9d | 250 ng | | |
| (B1) DBA/2 | 10 | Male | intradermal | Placebo (P.S.) | — | | |
| (B2) DBA/2 | 10 | Male | intradermal | 9d | 250 ng | | |
| (B3) DBA/2 | 10 | Male | intradermal | Cisplatin | 65 µg | | |
| (B4) DBA/2 | 10 | Male | intradermal | 9d Cisplatin | 250 ng 65 µg | | |
| (C1) DBA/2 | 10 | Male | intramuscular | Placebo (P.S.) | — | | |
| (C2) DBA/2 | 10 | Male | intramuscular | 9d | 250 ng | | |

*Dose per day and mouse
**At intramuscular inoculation, as well as those days, mice were treated on days 32 and 35.

Statistics

A case-control study was performed with treated and control mice in order to determine whether differences between placebo, 9d, Cisplatin or 9d+Cisplatin were present. The data obtained (tumour surface and volume) were tested for Normal distribution within the groups (Kolmogorov Smirnov test p<0.05). A non-parametrical hypothesis test for unpaired samples was performed in order to contrast whether 9d, Cisplatin or 9d+Cisplatin had a deletereous effect on tumoral growth. The U-test of Mann Withney was chosen for being one of the better known non-parametrical tests, anyway, results for this test are equivalent both to those of Wilcoxon's sum of ranges and Kruskal-Wallis two-groups test.

All statistical analysis were performed with SPSS (Statistical Package for Social Sciences) v13.0.

Results

The Inhibitory Effect of Isomer 4 (9d) on KLN 205 Tumour Cell Growth

Ten mice per group were planned to be studied.

Tables 18 and 19 show the results of each experimental group expressed as the median values. These tables summarize the median of surface or volume on each day scored.

TABLE 18

SURFACE (mm$^2$)
Overall values (Median)

| Treatment | Dose ng/mouse | Group | n (first day) | 0 | 10 | 13 | 17 | 20 | 24 | 27 | 31 | 34 | 38 |
|---|---|---|---|---|---|---|---|---|---|---|---|---|---|
| P.S. | — | A1 | 10 | 0 | 18 | 32.5 | 61.5 | 100 | 156.5 | 206.5 | 268 | | |
| 9d | 250 | A2 | 10 | 0 | 12.5 | 30 | 45 | 70 | 118.5 | 159 | 186 | | |
| P.S. | — | B1 | 10 | 0 | 12.5 | 25 | 54 | 89.5 | 142 | 186 | 221 | | |
| 9d | 250 ng | B2 | 10 | 0 | 12.5 | 25 | 42 | 63.5 | 95 | 128 | 162.5 | | |
| Cisplatin | 65 μg | B3 | 10 | 0 | 6.5 | 20 | 33 | 56 | 96 | 129 | 155 | | |
| 9d + Cisplatin | 250 ng + 65 μg | B4 | 10 | 0 | 6.5 | 18 | 30 | 56 | 88 | 120 | 143 | | |
| P.S. | — | C1 | 10 | 0 | 0 | 0.23 | 0.4 | 0.63 | 2.8 | 6.5 | 12.25 | 19.89 | 34.68 |
| 9d | 250 | C2 | 10 | 0 | 0.03 | 0.17 | 0.315 | 0.93 | 1.83 | 6.94 | 12.26 | 24.34 | 37.56 |

TABLE 19

VOLUME (mm$^3$)
Overall values (Median)

| Treatment | Dose ng/mouse | Group | n (first day) | 0 | 10 | 13 | 17 | 20 | 24 | 27 | 31 |
|---|---|---|---|---|---|---|---|---|---|---|---|
| P.S. | — | A1 | 10 | 0 | 36 | 81.25 | 208.25 | 400 | 793.25 | 1217 | 1860.5 |
| 9d | 250 | A2 | 10 | 0 | 22.75 | 75 | 135 | 245 | 506.25 | 800 | 1058.75 |
| P.S. | — | B1 | 10 | 0 | 22.75 | 62.5 | 166.75 | 336 | 748.5 | 1116 | 1436.5 |
| 9d | 250 ng | B2 | 10 | 0 | 22.75 | 62.5 | 126 | 232.75 | 425.25 | 608.5 | 885.75 |
| Cisplatin | 65 μg | B3 | 10 | 0 | 8.75 | 40 | 91.5 | 196 | 384 | 646.5 | 775 |
| 9d + Cisplatin | 250 ng + 65 μg | B4 | 10 | 0 | 8.75 | 36 | 75 | 196 | 352 | 600 | 786.5 |

Tables 20 and 21 show the results of each experimental group expressed as the mean values. These tables summarize the mean of surface or volume on each day scored.

TABLE 20

SURFACE (mm$^2$)
Overall values (Mean)

| Treatment | Dose ng/mouse | Group | n (first day) | 0 | 10 | 13 | 17 | 20 | 24 | 27 | 31 | 34 | 38 |
|---|---|---|---|---|---|---|---|---|---|---|---|---|---|
| P.S. | — | A1 | 10 | 0 | 17.8 | 33.3 | 67.9 | 112.5 | 163.9 | 214 | 270.7 | | |
| 9d | 250 | A2 | 10 | 0 | 11.4 | 27.4 | 49 | 74.4 | 117.4 | 149.3 | 179.2 | | |
| P.S. | — | B1 | 10 | 0 | 13.9 | 30.6 | 63.4 | 97.9 | 141.9 | 185.3 | 231.6 | | |
| 9d | 250 ng | B2 | 10 | 0 | 14.3 | 27.9 | 46.3 | 71.2 | 107.8 | 141.7 | 177.1 | | |
| Cisplatin | 65 μg | B3 | 10 | 0 | 7.3 | 20 | 38.3 | 62.2 | 93.7 | 124.1 | 151.3 | | |
| 9d + Cisplatin | 250 ng + 65 μg | B4 | 10 | 0 | 6.8 | 17 | 31.3 | 54.6 | 82.6 | 115 | 143.6 | | |
| P.S. | — | C1 | 10 | 0 | 0.04 | 0.25 | 0.36 | 0.69 | 2.64 | 6.81 | 12.48 | 20.78 | 34.38 |
| 9d | 250 | C2 | 10 | 0 | 0.06 | 0.18 | 0.37 | 0.89 | 2.48 | 6.7 | 13.61 | 29.17 | 41.53 |

TABLE 21

| | | | n | Days after tumour inoculation | | | | | | | |
|---|---|---|---|---|---|---|---|---|---|---|---|
| Treatment | Dose ng/mouse | Group | (first day) | 0 | 10 | 13 | 17 | 20 | 24 | 27 | 31 |
| P.S. | — | A1 | 10 | 0 | 41.3 | 93.05 | 257.35 | 534.45 | 887.35 | 1315 | 1879.85 |
| 9d | 250 | A2 | 10 | 0 | 22 | 75.5 | 171.6 | 304.2 | 554.9 | 765.05 | 1020 |
| P.S. | — | B1 | 10 | 0 | 27.65 | 85.5 | 229.1 | 447.75 | 777.15 | 1155.45 | 1595.8 |
| 9d | 250 ng | B2 | 10 | 0 | 28.85 | 74.95 | 150.05 | 280.6 | 496.8 | 744.75 | 1029.35 |
| Cisplatin | 65 μg | B3 | 10 | 0 | 11.05 | 43.6 | 115.95 | 233.5 | 408.05 | 642.55 | 848.95 |
| 9d + Cisplatin | 250 ng + 65 μg | B4 | 10 | 0 | 10.3 | 37.7 | 91.15 | 201.6 | 350.8 | 592.9 | 835.8 |

VOLUME (mm$^3$) Overall values (Mean)

There were differences in subcutaneous KLN 205 tumour growth rate among mice receiving 9d vs. placebo. These differences, either in surface or volume, were statistically significant (p<0.05) all days scored after the day 20$^{th}$ of tumour development as calculated by Mann-Whitney U test.

There were not differences in intradermal KLN 205 tumour growth rate among mice receiving 9d vs. placebo. There was a significant tendency, either in surface or volume, all days scored after day 17$^{th}$ of tumour development as calculated by Mann-Whitney U test.

There were differences in intradermal KLN 205 tumour growth rate among mice receiving Cisplatin vs. placebo. These differences, either in surface or volume, were statistically significant (p<0.05) on days 17$^{th}$, 20$^{th}$ and 31$^{th}$ of tumour development as calculated by Mann-Whitney U test.

There were differences in intradermal KLN 205 tumour growth rate among mice receiving 9d+Cisplatin vs. placebo. These differences, either in surface or volume, were statistically significant (p<0.05) all days scored after the day 13$^{th}$ of tumour development as calculated by Mann-Whitney U test.

There were not differences in intramuscular KLN 205 tumour growth rate among mice receiving 9d vs. placebo as calculated by Mann-Whitney U test.

Isomer 4 (9d) inhibit the in vivo growth of subcutaneous KLN 205 cells. 9d+Cisplatin or Cisplatin inhibit the in vivo growth of intradermal KLN 205 cells.

Example 13

Effect of 9d in Combination with Cisplatin on Tumour Growth

Tumor Assayed: Lewis

This assay was made in order to check the effect on in vivo tumour growth in mice challenged with Lewis lung cells. Their effect will be compared with the combination of chemotherapeutic agents plus 9d and/or placebo.

Materials and Methods

Tumor

Lewis Lung is a lung cell carcinoma originated in C57BL/6J mice strain, and therefore syngeneic in mice with C57BL/6J genetic background (Rodrigo Garzón M, Tirapu Fernández de la Cuesta I, Arina Iraeta A, Noel Centelles Llorente M and Zulueta Francés J. Use of Gene Therapy in a Subcutaneous Murine Model of Lung Cancer. *Arch Bronconeumology*. 42: 526-532; 2006).

Lewis lung cells (CLS, Eppelheim, Germany) were maintained in vitro by serial passages every 3-4 days. Cultures were performed with RPMI medium (RPMI, 10% foetal calf serum, 2 mM L-glutamine, non essential aminoacids, 1 mM sodium pyruvate, 20 mM HEPES, 80 μg/mL gentamycin; all of them were purchased from Sigma, St. Louis, Mo., USA) by seeding 5×10$^6$ cells onto 75 cm$^2$ culture flasks. Subcultures were carried out by collecting detached cells after treatment with trypsin-EDTA (Sigma, St. Louis, Mo., USA). Tumour cells, collected from 48 hour cultures, were used as source of Lewis Lung cells for the studies described below.

Mice

| Animal | C57BL/6NCrI |
|---|---|
| Justification for the selection | Inbred mouse strain syngeneic with Lewis lung cells |
| Supplier | Charles River Laboratories |
| Number of Study animals | ca. 60 males |
| Age at the start of treatment | 8-10 weeks old |
| Weight | 20-25 g |
| Identification | By means of an ear-punch technique |

Dose

Cisplatin was tested at the dose levels of 65 μg administrated on days 7, 11, 14, 18, 21, 24 and 27 after tumour inoculation.

Isomer 4 (9d) was tested at the dose levels of 250 ng administrated on days 7, 11, 14, 18, 21, 24 and 27 after tumour inoculation.

Study Design

Tumours were established by subcutaneous inoculation in the right hind flank. Mice were inoculated with 0.2 mL containing 2×10$^5$ viable cells. The day of subcutaneous inoculation will be considered Day 0 of the test.

Mice were distributed into 4 experimental groups:

| Group & strain | n | Sex | Treatment | Dose* | Days | Route |
|---|---|---|---|---|---|---|
| (A1) C57BL/6J | 15 | Male | Placebo (P.S.) | — | 7, 11, 14, 18, 21, 25, 28 | ip. |
| (B1) C57BL/6J | 15 | Male | 9d | 250 ng | | |
| (C1) C57BL/6J | 15 | Male | Cisplatin | 65 μg | | |
| (D1) C57BL/6J | 15 | Male | 9d Cisplatin | 250 ng 65 μg | | |

*Dose per day and mouse

Mice were observed daily and the tumour size recorded twice a week. This was carried out by measuring two perpendicular diameters (d1/d2) with a calliper. These measures were used to obtain both tumour surface and volume:

Tumour surface=$d1 \times d2 (mm^2)$

Tumour volume=$d1 \times d2^2 \times \frac{1}{2} (mm^3)$

Results were expressed as single values and/or as the mean±SD or median from each experimental group.

Statistics

A case-control study was performed with treated and control mice in order to determine whether differences between placebo, 9d, Cisplatin or 9d+Cisplatin were present. The data obtained (tumour surface and volume) were tested for Normal distribution within the groups (Kolmogorov Smirnov test $p<0.05$). A non-parametrical hypothesis test for unpaired samples was performed in order to contrast whether 9d, Cisplatin or 9d+Cisplatin had a deletereous effect on tumoral growth. The U-test of Mann Withney was chosen for being one of the better known non-parametrical tests, anyway, results for this test are equivalent both to those of Wilcoxon's sum of ranges and Kruskal-Wallis two-groups test.

We excluded of the study animals that have undetectable or unscored tumour on 31th day after tumour inoculation. Due to the high dispersion of data, outlayers were excluded of the study.

All statistical analysis were performed with SPSS (Statistical Package for Social Sciences) v13.0.

Results

The Effect of Isomer 4 (9d) on Lewis Lung Tumour Growth

Fifhteen mice per group were planned to be studied. One mice from placebo group died for unknown causes the second week after tumour inoculation and was excluded.

Tables 22 and 23 show the results of each experimental group expressed as the median values. These tables summarize the median of surface or volume in P.S, 9d, Cisplatin or 9d+Cisplatin mice group on each day scored.

TABLE 22

SURFACE ($mm^2$)
Overall values (Median)

| Treatment | Dose | Group | n (first day) | 0 | 10 | 13 | 17 | 20 | 24 | 27 | 31 |
|---|---|---|---|---|---|---|---|---|---|---|---|
| P.S. | — | A1 | 15 | 0 | 4 | 16 | 36 | 61.5 | 104 | 154.5 | 217 |
| 9d | 250 ng | B1 | 15 | 0 | 0 | 4 | 24 | 36 | 80 | 88 | 130 |
| Cisplatin | 65 µg | C1 | 15 | 0 | 0 | 4 | 25 | 49 | 90 | 120 | 169 |
| 9d + Cisplatin | 250 ng + 65 µg | D1 | 15 | 0 | 1 | 9 | 25 | 49 | 90 | 130 | 165 |

TABLE 23

VOLUME ($mm^3$)
Overall values (Median)

| Treatment | Dose | Group | n (first day) | 0 | 10 | 13 | 17 | 20 | 24 | 27 | 31 |
|---|---|---|---|---|---|---|---|---|---|---|---|
| P.S. | — | A1 | 15 | 0 | 4 | 32 | 108 | 208.25 | 493 | 885.75 | 1519 |
| 9d | 250 ng | B1 | 15 | 0 | 0 | 4 | 48 | 108 | 320 | 364.5 | 665.5 |
| Cisplatin | 65 µg | C1 | 15 | 0 | 0 | 4 | 56 | 171.5 | 405 | 600 | 1080 |
| 9d + Cisplatin | 250 ng + 65 µg | D1 | 15 | 0 | 0.5 | 13.5 | 62.5 | 162 | 384 | 650 | 936 |

Tables 24 and 25 show the results of each experimental group expressed as the mean values. These tables summarize the mean of surface or volume in P.S, 9d, Cisplatin or 9d+Cisplatin mice group on each day scored.

TABLE 24

SURFACE ($mm^2$)
Overall values (Mean)

| Treatment | Dose | Group | n (first day) | 0 | 10 | 13 | 17 | 20 | 24 | 27 | 31 |
|---|---|---|---|---|---|---|---|---|---|---|---|
| P.S. | — | A1 | 15 | 0 | 4.53 | 13.87 | 33.6 | 56.5 | 97.79 | 151.86 | 223.93 |
| 9d | 250 ng | B1 | 15 | 0 | 2 | 6.47 | 20.13 | 34.33 | 60.6 | 104.8 | 141.8 |
| Cisplatin | 65 µg | C1 | 15 | 0 | 2.4 | 6.73 | 20.73 | 58.33 | 106.07 | 160.07 | 204.93 |
| 9d + Cisplatin | 250 ng + 65 µg | D1 | 15 | 0 | 2.47 | 9 | 21.87 | 46.67 | 85.8 | 132.27 | 176.53 |

TABLE 25

VOLUME (mm³)
Overall values (Mean)

| Treatment | Dose | Group | n (first day) | Days after tumour inoculation | | | | | | | |
|---|---|---|---|---|---|---|---|---|---|---|---|
| | | | | 0 | 10 | 13 | 17 | 20 | 24 | 27 | 31 |
| P.S. | — | A1 | 15 | 0 | 6.47 | 31.27 | 99.07 | 214.11 | 477.04 | 902.71 | 1630.89 |
| 9d | 250 ng | B1 | 15 | 0 | 2.27 | 12.5 | 52.73 | 112.3 | 253.77 | 557.13 | 887.17 |
| Cisplatin | 65 µg | C1 | 15 | 0 | 3.27 | 11.23 | 49.97 | 269.1 | 619.43 | 1076.9 | 1530.4 |
| 9d + Cisplatin | 250 ng + 65 µg | D1 | 15 | 0 | 2.97 | 15.83 | 52.67 | 159.47 | 383.37 | 718.87 | 1112.53 |

There were differences in the Lewis Lung tumour growth rate among mice receiving 9d vs. placebo. These differences, either in surface or volume, were statistically significant ($p<0.05$) all days scored after the day 13th of tumour development as calculated by Mann-Whitney U test.

There were differences in the Lewis Lung tumour growth rate among mice receiving Cisplatin vs. placebo. These differences, either in surface or volume, were statistically significant ($p<0.05$) on days 10th, 13th and 17 th of tumour development as calculated by Mann-Whitney U test.

There were differences in the Lewis Lung tumour growth rate among mice receiving 9d+Cisplatin vs. placebo. These differences, either in surface or volume, were statistically significant ($p<0.05$) all days scored after the day 17th of tumour development as calculated by Mann-Whitney U test.

9d, Cisplatin and 9d+Cisplatin inhibit the in vivo growth of Lewis lung tumour growth in inbred mice.

Example 14

Toxicity

This assay was made in order to check the tolerance (lethality/toxicity) of BLAS and IL-2 treatments in mice.

Materials and Methods

Drugs in Study
BLAS (equimolar mixture of isomers 1, 2, 3 and 4) 1.25 mg/mL in sterile physiological saline.
Human recombinant IL-2, at $18 \times 10^6$ IU/mL (Proleukin; Chiron Iberia, Madrid, Spain)
Mice

| Animal | Balb/c AnNHsd |
|---|---|
| Justification for the selection | Inbred mouse strain |
| Supplier | Harlan Iberica |
| Number of Study animals | ca. 50 males |
| Age at the start of treatment | 12 weeks old |
| Weight | 25-30 g |
| Identification | By means of an ear-punch technique |

Dose, Vehicle, Route and Volume Administration
Dose

| Group | Product | Dose tested* | Reference dose | Days |
|---|---|---|---|---|
| A1 | BLAS | 1 µg | 260 ng | 0, 1, 4 and 5 |
| A2 | | 25 µg | | |
| A3 | | 250 µg | | |

-continued

| Group | Product | Dose tested* | Reference dose | Days |
|---|---|---|---|---|
| B1 | IL-2 | 900,000 IU | 300,000 IU | |
| B2 | | 1,800,000 IU | | |

*Dose per mouse and day, using a constant volume of 0.2 mL

Vehicle

The vehicle in which BLAS and IL-2 were diluted was sterile physiological saline for injection (Grifols, Barcelona, Spain) and sterile distilled water for injection (Grifols, Barcelona, Spain)

Administration Route

The treatments were given i.p.

Study Design

Every mouse was observed daily during 30 days.

Two measures were performed:

1. Lethality. This was expressed as percentage of survival.
2. Toxicity. This was checked on alive mice for the following parameters and score criteria:

| Parameter | | Score |
|---|---|---|
| General aspect: | Normal | 0 |
| | Coat affected | 1 |
| | Coat affected plus ocular/nasal secretions | 2 |
| | Abnormal position | 3 |
| Abnormal behaviour: | Absence | 0 |
| | Presence | 3 |

Results

Lethality and Toxicity Associated with BLAS and IL-2 Treatment

Table 26 shows the lethality observed with either treatment. Results are expressed as percentage of survival. As can be seen in this table, two mice from Group B2, receiving the highest dose of IL-2, died on day 6 and 7 after the first dose. No more death were observed in any other group of mice, whether treated with IL-2 (lower dose) or BLAS at any dose used.

TABLE 26

LETHALITY

| Treatment | Dose (mouse) | Group | \multicolumn{12}{c}{Days after the beginning of the treatment} |
|---|---|---|---|---|---|---|---|---|---|---|---|---|---|---|
| | | | 0 | 1 | 2 | 3 | 4 | 5 | 6 | 7 | 8 | 9 | 30 | 31 |
| BLAS | 1 μg | A1 | 100 | 100 | 100 | 100 | 100 | 100 | 100 | 100 | 100 | 100 | 100 | 100 |
| BLAS | 25 μg | A2 | 100 | 100 | 100 | 100 | 100 | 100 | 100 | 100 | 100 | 100 | 100 | 100 |
| BLAS | 250 μg | A3 | 100 | 100 | 100 | 100 | 100 | 100 | 100 | 100 | 100 | 100 | 100 | 100 |
| IL-2 | $9 \times 10^5$ UI | B1 | 100 | 100 | 100 | 100 | 100 | 100 | 100 | 100 | 100 | 100 | 100 | 100 |
| IL-2 | $1.8 \times 10^6$ UI | B2 | 100 | 100 | 100 | 100 | 100 | 100 | 90 | 80 | 80 | 80 | 80 | 80 |

Table 27 shows the toxicity observed in mice with either treatment as scored with the criteria described above. Results are expressed as the toxic score accumulated per group of treatment.

TABLE 27

TOXICITY SCORE

| Treatment | Dose (mouse) | Group | \multicolumn{17}{c}{Days after the beginning of the treatment} |
|---|---|---|---|---|---|---|---|---|---|---|---|---|---|---|---|---|---|---|---|
| | | | 0 | 1 | 2 | 3 | 4 | 5 | 6 | 7 | 8 | 9 | 10 | 11 | 12 | 13 | 14 | 15 | 16 | 30 | 31 |
| BLAS | 1 μg | A1 | 0 | 0 | 0 | 0 | 0 | 0 | 0 | 0 | 0 | 0 | 0 | 0 | 0 | 0 | 0 | 0 | 0 | 0 | 0 |
| BLAS | 25 μg | A2 | 0 | 0 | 0 | 0 | 0 | 0 | 0 | 0 | 0 | 0 | 0 | 0 | 0 | 0 | 0 | 0 | 0 | 0 | 0 |
| BLAS | 250 μg | A3 | 0 | 0 | 0 | 0 | 0 | 0 | 0 | 0 | 0 | 0 | 0 | 0 | 0 | 0 | 0 | 0 | 0 | 0 | 0 |
| IL-2 | $9 \times 10^5$ UI | B1 | 0 | 0 | 1 | 1 | 4 | 10 | 10 | 10 | 9 | 9 | 5 | 1 | 1 | 0 | 0 | 0 | 0 | 0 | 0 |
| IL-2 | $1.8 \times 10^6$ UI | B2 | 0 | 0 | 1 | 7 | 25 | 45 | 35 | 32 | 32 | 26 | 24 | 26 | 18 | 18 | 10 | 3 | 0 | 0 | 0 |

As can bee seen in this table, toxicity was only observed in IL-2 treated mice (Groups B1&B2) Group B2 (highest IL-2 dose) showed the more marked adverse effects but mice from Group B1 (lower dose) also was cored although with a lower extent. Adverse effects were seen during and after IL2-treatment (from day 2 to day 15) As could be expected, later on these effects disappeared since IL-2 was discontinued six days after the initial dose. It should be noted BLAS was apparently not toxic at all, and no point could be scored in any mouse during the follow-up. This is remarkable, as the dose used in this study exceeded 1,000-fold the therapeutic dose used in most of the examples above.

BLAS in contrast to IL-2 is well tolerated by mice even a doses that greatly exceed its therapeutic range.

Example 15

Toxicity of Isomer 4 (9d)

This assay was made in order to perform a preliminary study to address the toxic effect of Isomer 4 (9d) used at a high dose on healthy mice. Its eventual toxicity will be compared with placebo.

Materials and Methods

Drug in Study
Active Substance
Isomer 4 (9d) at 0.7 mg/mL in sterile physiological saline.
Placebo
Sterile physiological saline for injection (Grifols, Barcelona, Spain)
Mice

| Animal | C57BL/6NCrI |
|---|---|
| Supplier | CRIFFA - Charles River |
| Number of Study animals | ca. 10 males |

-continued

| Age at the start of | 24 weeks old |
|---|---|
| Weight treatment | 23-29 g |
| Identification | By means of an ear-punch technique |
| Animal | Swiss |
| Supplier | CRIFFA - Charles River |
| Number of Study animals | ca. 10 females |
| Age at the start of | 24 weeks old |
| Weight treatment | 25-30 g |
| Identification | By means of an ear-punch technique |

Dose, Vehicle, Route and Volume Administration
Dose

| Group | Product | Dose tested* | Reference dose | Mice strain | Day of administration |
|---|---|---|---|---|---|
| A1 | Isomer 4 | 1.25 mg (i.p.) | 260 ng | C57BL/6NCrI | 0 |
| B1 | Placebo | — | — | | |
| C1 | Isomer 4 | 140 μg (s.c.) | 260 ng | Swiss | |
| D1 | Placebo | — | — | | |

*Dose per mouse and day, using a constant volume of 1.8 mL (A1, B1) or 0.2 mL (C1, D1)

Vehicle

The vehicle in which Isomer 4 was diluted was sterile physiological saline for injection (Grifols, Barcelona, Spain) and sterile distilled water for injection (Grifols, Barcelona, Spain)

Administration Route

The treatments were given i.p. or s.c.

Study Design

Every mouse was observed daily during 10 days.

Three measures were performed:

3. Weight. This was measured and expressed in grammes.
4. Lethality. This was expressed as percentage of survival.
5. Toxicity. This was checked on alive mice for the following parameters and score criteria:

| Parameter | | Score |
|---|---|---|
| Systemic Toxicity | | |
| General aspect: | Normal | 0 |
| | Coat affected | 1 |
| | Coat affected plus ocular/nasal secretions | 2 |
| | Abnormal position | 3 |
| | Abnormal position plus immobility | 4 |
| Abnormal behaviour: | Absence | 0 |
| | Presence | 3 |
| Local Toxicity | | |
| | Normal | 0 |
| | Erythema at the inoculation site | 1 |
| | Erythema plus irritation/wheal | 2 |

| Parameter | Score |
|---|---|
| Erythema plus irritation/wheal plus coat affected | 3 |
| Necrosis at the inoculation site | 4 |

Statistics

A case-control study was performed with treated and control mice in order to determine whether differences between Isomer 4 and administration of placebo were present. The U-test of Mann Withney was chosen for being one of the better known non-parametrical tests, anyway, results for this test are equivalent both to those of Wilcoxon's sum of ranges and Kruskal-Wallis two-groups test.

The statistic software used was SPSSv12.0

Results

Lethality and Toxicity Associated with Isomer 4 Treatment

Tables 28 and 29 show the weight of each C57BL/6 mice every day scored as well as mean, standard deviation and median. No differences on weight between groups were observed as detected by Mann-Whitney U test ($p>0.05$)

TABLE 28

WEIGHT LOSS
Group A1 (Isomer 4)

| Animal | | Days after the beginning of the treatment | | | | | | | | | | |
|---|---|---|---|---|---|---|---|---|---|---|---|---|
| n° | code | 0 | 1 | 2 | 3 | 4 | 5 | 6 | 7 | 8 | 9 | 10 |
| 1 | 1 | 23 | 22 | 22 | 22 | 21 | 20 | 20 | 20 | 20 | 20 | 19 |
| 2 | 2 | 29 | 28 | 28 | 29 | 29 | 27 | 28 | 28 | 28 | 28 | 28 |
| 3 | 3 | 27 | 26 | 26 | 26 | 26 | 26 | 26 | 26 | 26 | 26 | 25 |
| 4 | 4 | 27 | 26 | 26 | 27 | 27 | 26 | 26 | 26 | 26 | 26 | 26 |
| 5 | 5 | 26 | 25 | 25 | 26 | 26 | 25 | 25 | 25 | 26 | 25 | 26 |
| MEAN | | 26.4 | 25.4 | 25.4 | 26 | 25.8 | 24.8 | 25 | 25 | 25.2 | 25 | 24.8 |
| SD | | 2.19 | 2.19 | 2.19 | 2.55 | 2.95 | 2.77 | 3 | 3 | 3.03 | 3 | 3.420526 |
| MEDIAN | | 27 | 26 | 26 | 26 | 26 | 26 | 26 | 26 | 26 | 26 | 26 |
| n | | 5 | 5 | 5 | 5 | 5 | 5 | 5 | 5 | 5 | 5 | 5 |

TABLE 29

WEIGHT LOSS
Group B1 (Placebo)

| Animal | | Days after the beginning of the treatment | | | | | | | | | | |
|---|---|---|---|---|---|---|---|---|---|---|---|---|
| n° | code | 0 | 1 | 2 | 3 | 4 | 5 | 6 | 7 | 8 | 9 | 10 |
| 1 | 1 | 27 | 27 | 26 | 27 | 27 | 27 | 27 | 27 | 27 | 27 | 27 |
| 2 | 2 | 26 | 26 | 25 | 25 | 26 | 26 | 26 | 25 | 26 | 26 | 26 |
| 3 | 3 | 25 | 25 | 25 | 25 | 25 | 25 | 25 | 25 | 25 | 25 | 25 |
| 4 | 4 | 27 | 27 | 26 | 26 | 26 | 25 | 25 | 26 | 26 | 26 | 26 |
| 5 | 5 | 28 | 28 | 27 | 27 | 27 | 27 | 27 | 26 | 27 | 27 | 28 |
| MEAN | | 26.6 | 26.6 | 25.8 | 26 | 26.2 | 26 | 26 | 25.8 | 26.2 | 26.2 | 26.4 |
| SD | | 1.14 | 1.14 | 0.84 | 1 | 0.84 | 1 | 1 | 0.84 | 0.84 | 0.84 | 1.140175 |
| MEDIAN | | 27 | 27 | 26 | 26 | 26 | 26 | 26 | 26 | 26 | 26 | 26 |
| n | | 5 | 5 | 5 | 5 | 5 | 5 | 5 | 5 | 5 | 5 | 5 |

No deaths or toxicity were observed in any group of mice, treated with Isomer 4 (Group A1) or physiologic saline (Group B1). It is of note that the dose used for systemic toxicity exceeded 50,000-fold the total amount of the therapeutic dose.

Local toxicity was neither observed in Isomer 4 (Group C1) or placebo (Group D1) treated mice. It is of note that the dose used for local toxicity in this study exceeded 500-fold the normal concentration of the therapeutic dose.

Thus, isomer 4 is well tolerated by mice even a doses that greatly exceed its therapeutic range. Local toxicity at the inoculation site is not observed in any mouse challenged.

Example 16

Phenotype Leukocyte Analysis

This Example was carried out with the aim at assessing eventual differences in the leukocyte population percentage among the treated mice by flow cytometry. The counts were carried out by using a flow cytometer after labelling membrane proteins (CD11B and Ly6G) with specific antibodies to said proteins. CD11B (also known as Mac-1) marker is expressed in monocyte populations whereas Ly6G (also known as GR-1) is expressed in granulocyte populations. Both markers (CD11b and Ly6G) are expressed in neutrophile populations. This assay shows that the assayed compound increases white blood cell populations, particularly from the myeloid cell lineage, what is important in cases which require enhancing the immuneresponse in a subject, such as, for example, in patients suffering AIDS.

Materials and Methods

Drug in Study
Isomer 4 (compound 9d) at 65 μg/mL in sterile physiological saline.
Placebo
Physiologic saline (Grifols, Barcelona, Spain).
Mice

| Animal | Balb/cByJ |
|---|---|
| Justification for the selection | Inbred mouse strain syngeneic with Renca tumour cells |
| Supplier | CRIFFA - Charles River |
| Number of Study animals | 10 ca. males |
| Age at the start of treatment | 10-12 weeks old |
| Weight | 25-30 g |
| Identification | By means of an ear-punch technique |

Equipment
Laminar flood hood, Flow cytometer, Adjustable pipettes, Sterile syringes, Sterile needles, EDTA stelile tubes, Plastic tubes.
Reagents
    Anaesthetic solution
    Sterile PBS (Sigma, St. Louis, Mo., USA)
    Physiological saline (Grifols, Barcelona, Spain)
    Rat anti-mouse CD11b-PE (Beckman Coulter, Fullerton, Calif., USA)
    Rat anti-mouse Ly6G-FITC (Beckman Coulter, Fullerton, Calif., USA)
    Optylise C (Beckman Coulter, Fullerton, Calif., USA)
Dose, Vehicle, Route and Volume Administration
Dose
Isomer 4 (compound 9d) was tested at the dose levels of 250 ng administered on days 0, and 7.

Vehicle
The vehicle in which Isomer 4 was diluted is physiological saline.
Administration Route and Volume
The treatments were given by intraperitoneal route. The volume inoculated was 200 μl/animal.
Study Design
Balb/c mice were distributed into 2 experimental groups:

| Group | n | Sex | Treatment | Dose* | Days | Route |
|---|---|---|---|---|---|---|
| (A1) BALB/C | 5 | Male | Placebo (P.S.) |  | 0 and 7 | i.p. |
| (B1) BALB/C | 5 | Male | Isomer 4 | 250 ng |  |  |

*Dose per day and mouse

Three days after the last dose of the treatment, murine blood was isolated. It was obtained directly from intracardiac punction. Previously, mice were anesthetized intramuscularly.

Blood was mixed with the monoclonal antibodies described above.

After 20 minutes of incubation, Optylise C solution was added into the samples to lise erythrocytes population.

Finally, samples were diluted ½ with 1× sterile PBS and checked by flow cytometry.

Percentages of each population analyzed were expressed as single values and as the mean±SD from each experimental group.

| | ID | Control (n = 5) % | Compound 9d (n = 4) % |
|---|---|---|---|
| CD11b+ | 1 | 21.6 | 44 |
| | 2 | 22.4 | 35.4 |
| | 3 | 18.4 | — |
| | 4 | 11.2 | 32.9 |
| | 5 | 9.74 | 35.5 |
| | Media | 16.668 | 36.95 |
| | Standard deviation | 5.875297439 | 4.851460261 |
| Ly6G+ | 1 | 16.9 | 27 |
| | 2 | 22.1 | 37.6 |
| | 3 | 28.9 | — |
| | 4 | 23.7 | 33.3 |
| | 5 | 10.7 | 41.2 |
| | Media | 20.46 | 34.775 |
| | Standard deviation | 6.934551175 | 6.107031467 |
| CD11b+Ly6G+ | 1 | 16.1 | 29.7 |
| | 2 | 20.4 | 32.3 |
| | 3 | 13.7 | — |
| | 4 | 7.78 | 28.5 |
| | 5 | 8.02 | 33.7 |
| | Media | 13.2 | 31.05 |
| | Standard deviation | 5.401592358 | 2.37416652 |

RESULTS
Flow cytometry screening
PBL (Peripheral Blood)

According to these results mice (Balb/C) treated with two doses (once per week) of compound 9d show an increment of CD11b, Ly6G and CD11b+Ly6G positive cells in peripheral blood, compared with control mice (physiological saline). These cells were checked by flow cytometry three days after the last dose of the treatment.

The invention claimed is:
1. A substantially pure stereoisomer of formula

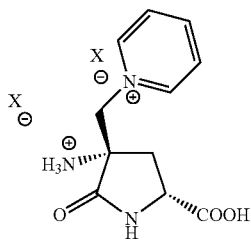

wherein X is a pharmaceutically acceptable anion.

2. The substantially pure stereoisomer according to claim 1, which is 3S,5R-1-(3-amino-5-carboxy-2-oxopyrrolidin-3-ylmethyl)pyridinium bromide hydrobromide.

3. A pharmaceutical composition comprising a substantially pure stereoisomer as defined in claim 1 and a pharmaceutically acceptable carrier.

4. A method for the treatment of a disease or condition selected from the group consisting of renal cancer, lung cancer, breast cancer, colorectal cancer, prostate cancer, melanoma, and mastocytoma, in a subject in need thereof, said method comprising administering to said subject a therapeutically effective amount of a substantially pure stereoisomer as defined in claim 1.

5. The method according to claim 4, wherein said substantially pure stereoisomer is 3S,5R-1-(3-amino-5-carboxy-2-oxopyrrolidin-3-ylmethyl)pyridinium bromide hydrobromide.

* * * * *